(12) United States Patent
Fabbri et al.

(10) Patent No.: US 9,000,265 B2
(45) Date of Patent: Apr. 7, 2015

(54) CORN PLANTS AND SEED ENHANCED FOR ASPARAGINE AND PROTEIN

(75) Inventors: Brandon J. Fabbri, Chesterfield, MO (US); Bo-Xing Qui, Chesterfield, MO (US); Steven E. Screen, Raleigh, NC (US); Scott Andersen, Manchester, MO (US); James Crowley, Manchester, MO (US)

(73) Assignee: Monsanto Technology LLC, St. Louis, MO (US)

( * ) Notice: Subject to any disclaimer, the term of this patent is extended or adjusted under 35 U.S.C. 154(b) by 8 days.

(21) Appl. No.: 13/338,101

(22) Filed: Dec. 27, 2011

(65) Prior Publication Data

US 2012/0291154 A1 Nov. 15, 2012

Related U.S. Application Data

(60) Continuation of application No. 12/694,152, filed on Jan. 26, 2010, now abandoned, which is a division of application No. 11/434,566, filed on May 15, 2006, now abandoned, and a continuation-in-part of application No. 11/978,677, filed on Oct. 30, 2007, now abandoned, which is a continuation-in-part of application No. 10/425,114, filed on Apr. 28, 2003, now abandoned, which is a continuation-in-part of application No. 09/826,019, filed on Apr. 5, 2001, now abandoned, which is a continuation-in-part of application No. 09/773,370, filed on Feb. 1, 2001, now abandoned, said application No. 10/425,114 is a continuation-in-part of application No. 10/219,999, filed on Aug. 15, 2002, now abandoned, and a continuation-in-part of application No. 09/666,355, filed on Sep. 20, 2000, now abandoned, and a continuation-in-part of application No. 09/985,678, filed on Nov. 5, 2001, now abandoned, which is a continuation of application No. 09/304,517, filed on May 6, 1999, now abandoned, and a continuation-in-part of application No. 09/849,529, filed on May 7, 2001, now abandoned, and a continuation-in-part of application No. 09/804,730, filed on Mar. 13, 2001, now abandoned, and a continuation-in-part of application No. 09/850,147, filed on May 8, 2001, now abandoned.

(60) Provisional application No. 60/681,348, filed on May 16, 2005, provisional application No. 60/179,730, filed on Feb. 2, 2000, provisional application No. 60/324,109, filed on Sep. 21, 2001, provisional application No. 60/312,544, filed on Aug. 15, 2001, provisional application No. 60/196,868, filed on May 9, 2000, provisional application No. 60/189,657, filed on Mar. 15, 2000, provisional application No. 60/202,213, filed on May 8, 2000.

(51) Int. Cl.

| | |
|---|---|
| A01H 5/00 | (2006.01) |
| C12N 15/82 | (2006.01) |
| C12N 9/00 | (2006.01) |
| A01H 1/00 | (2006.01) |
| C07H 21/04 | (2006.01) |
| C07K 14/415 | (2006.01) |
| C12N 15/00 | (2006.01) |
| C12N 15/63 | (2006.01) |
| C12N 15/29 | (2006.01) |
| C12N 15/52 | (2006.01) |

(52) U.S. Cl.
CPC .............. *C12N 15/8251* (2013.01); *C12N 9/93* (2013.01)

(58) Field of Classification Search
USPC .............. 435/6.1, 468, 412, 419, 183, 320.1; 530/370; 536/23.1, 23.2, 24.1; 800/320.1, 260, 278, 295
See application file for complete search history.

(56) References Cited

U.S. PATENT DOCUMENTS

| | | | |
|---|---|---|---|
| 5,508,468 A | 4/1996 | Lundquist et al. | 800/300.1 |
| 5,545,545 A | 8/1996 | Gengenbach et al. | 435/172.3 |
| 5,641,876 A | 6/1997 | McElroy et al. | 536/24.1 |
| 5,824,857 A | 10/1998 | Beachy et al. | 800/287 |
| 5,955,651 A | 9/1999 | Coruzzi et al. | 800/298 |
| 6,160,208 A | 12/2000 | Lundquist et al. | 800/320.1 |
| 6,326,527 B1 | 12/2001 | Kirihara et al. | 800/278 |
| 6,846,969 B2 | 1/2005 | Donn et al. | 800/288 |
| 8,357,833 B2 | 1/2013 | Andersen | |
| 2004/0034888 A1 | 2/2004 | Liu et al. | 800/289 |

(Continued)

FOREIGN PATENT DOCUMENTS

| | | |
|---|---|---|
| WO | WO 99/53050 | 10/1999 |
| WO | WO 03/000898 | 1/2003 |

(Continued)

OTHER PUBLICATIONS

Hughes et al., "Molecular cloning and expression of two cDNAs encoding asparagine synthetase in soybean", *Plant Molecular Biology* 33:301-311, 1997.
U.S. Appl. No. 13/042,433, filed Mar. 7, 2011, Andersen et al.
Chevalier et al., "Metabolic regulation of asparagine synthetase gene expression in maize (*Zea mays* L.) root tips," *Plant J.*, 9(1):1-11, 1996.
Database UniProt, "Metabolic regulation of asparagine synthetase gene expression in maize (*Zea mays* L.) root tips," Database Accession No. P49094, 1996.

(Continued)

*Primary Examiner* — Phuong Bui
(74) *Attorney, Agent, or Firm* — Dentons US LLP; Chunping Li, Esq.

(57) ABSTRACT

The present invention relates to a corn plant and seed with enhanced levels of protein and amino acids. The invention also relates to DNA constructs that provide expression in transgenic corn cells of an asparagine synthetase enzyme. The DNA constructs are used in a method to produce transgenic corn plants and seeds and to select for plants and seeds with enhanced levels of protein and amino acids.

8 Claims, 6 Drawing Sheets

(56) References Cited

U.S. PATENT DOCUMENTS

| | | |
|---|---|---|
| 2004/0133947 A1 | 7/2004 | Kisaka et al. |
| 2006/0075515 A1 | 4/2006 | Luethy et al. ............ 800/278 |
| 2007/0006338 A1 | 1/2007 | Fabbri |
| 2009/0081353 A1 | 3/2009 | Andersen et al. ......... 800/278 |
| 2011/0020526 A1 | 1/2011 | Fabbri et al. ............. 800/278 |
| 2011/0293815 A1 | 12/2011 | Andersen et al. ......... 800/278 |

FOREIGN PATENT DOCUMENTS

| | | |
|---|---|---|
| WO | WO 2005/033319 | 4/2005 |
| WO | WO 2006/124678 | 11/2006 |

OTHER PUBLICATIONS

Database UniProt, "Molecular cloning and expression of two cDNAs encoding asparagine synthetase in soybean," Database Accession No. P93167, 1997.

GenPept Accession No. CAA58052, dated Apr. 18, 2005.

GenBank Accession No. ADX46896, dated Feb. 14, 2011.

GenBank Accession No. ADX68119, dated May 17, 2011.

Ishida et al., "High efficiency transformation of maize (*Zea mays* L.) mediated by agrobacterium tumefaciens," *Nature Biotechnology*, 14:745-750, 1996.

Lam et al., "Overexpression of the ASN1 Gene enhances nitrogen status in seeds of arabidopsis," *Plant Physiology*, 132:926-935, 2003.

Lam et al., "Reciprocal regulation of distinct asparagine synthetase genes by light and metabolites in arabidopsis thaliana," *The Plant J.*, 16(3):345-353, 1998.

Matsuoka et al., "Tissue-specific light-regulated expression directed by the promoter of a C4 gene, maize pyruvate, orthophosphate dikinase, in a C3 plant, rice," *Proc. Natl. Acad. Sci. USA*, 90:9586-9590, 1993.

Schaefer et al., "Asparagine amide metabolism in developing cotyledons of soybean," *Proc. Natl. Acad. Sci. USA*, 78(10):5978-5982, 1981.

Schoenbeck et al., Decreased NADH glutamate synthase activity in nodules and flowers of alfalfa (*Medicago sativa* L.) transformed with an antisense glutamate synthase transgene, *Journal of Experimental Botany*, 51(342):29-39, 2000.

Seebauer et al., "Amino acid metabolism in maize earshoots. Implications for assimilate preconditioning and nitrogen signaling," *Plant Physiology*, 136:4326-4334, 2004.

Smith et al., "Gene expression—total silencing by intron-spliced hairpin RNAs," *Nature*, 407:319-320, 2000.

Todd et al., "Identification and characterization of four distinct asparagine synthetase (AsnS) genes in maize (*Zea mays* L.)," *Plant Sci.*, 175:799-808, 2008.

Waterhouse et al., "Virus resistance and gene silencing in plants can be induced by simultaneous expression of sense and antisense RNA," *Proc. Natl. Acad. Sci. USA*, 95:13959-13964, 1998.

Wesley et al., "Construct design for efficient, effective and high-throughput gene silencing in plants," *The Plant J.*, 27(6):581-590, 2001.

Wu et al., "Quantitative nature of the Prolamin-box, ACGT and AACA motifs in a rice glutelin gene promoter: minimal cis-element requirements for endosperm-specific gene expression," *The Plant J.*, 23(3):415-421, 2000.

Yamagata et al., "Molecular cloning and characterization of a cDNA encoding asparagine synthetase from soybean (*Glycine max* L.) cell cultures," *Biosci. Biotechnol Biochem.*, 62(1):148-150, 1998.

Zhu et al., "A T-DNA insertion knockout of the bifunctional lysine-ketoglutarate reductase/saccharopine dehydrogenase gene elevates lysine levels in arabidopsis seeds," *Plant Physiology*, 126:1539-1545, 2001.

Database GenSeq Accession No. ADX50548, dated Apr. 21, 2005.

Database GenSeq Accession No. ADX94117, dated Apr. 21, 2005.

Wong et al., "Correlation of ASN2 Gene Expression with Ammonium Metabolism in Arabidopsis," *Plant Physiol* 134(1):332-338, 2004.

Brears et al., "Ectopic Overexpression of Asparagine Synthetase in Transgenic Tobacco," *Plant Physiol.* 103(4):1285-1290, 1993.

SEQUENCE LISTING

<160> NUMBER OF SEQ ID NOS: 49

<210> SEQ ID NO 1
<211> LENGTH: 1869
<212> TYPE: DNA
<213> ORGANISM: Zea mays

<400> SEQUENCE: 1

| | |
|---|---:|
| atgatttgtg acaaatgcag cctcgtgcgg agcttttttg taggtagacc gcgggatatc | 60 |
| acaagtttgt acaaaaaagc aggctcctgc aggaccatgt gcggcatcct cgctgtcctc | 120 |
| ggcgtcgctg aggtctccct cgccaagcgc tcccgcatca ttgagctctc gcgcaggtta | 180 |
| cggcaccgag ggcctgattg gagtggtttg cactgtcatg aggattgtta ccttgcacac | 240 |
| cagcggttgg ctattatcga tcctacatct ggagaccagc ctttgtacaa tgaggataaa | 300 |
| acagttgttg taacggtgaa cggagagatc tataaccatg aagaattgaa agctaagttg | 360 |
| aaaactcatg agttccaaac tggcagtgat tgtgaagtta tagcccatct ttacgaagaa | 420 |
| tatggcgaag aatttgtgga tatgttggat ggaatgttct cctttgttct tcttgataca | 480 |
| cgtgataaaa gcttcatcgc agctcgtgat gctattggca tctgcccttt atacatggga | 540 |
| tggggtcttg atggatcagt ctggttttct tcagagatga aggcattgag tgatgattgt | 600 |
| gaacgcttca taacatttcc cccagggcat ctctactcca gcaagacagg tggtctaagg | 660 |
| agatggtaca acccaccatg gttttcagag acggtccctt caaccccta caatgctctc | 720 |
| ttcctccggg agatgtttga gaaggctgtt attaagaggc tgatgactga tgtgccattt | 780 |
| ggtgtgcttt tatctggtgg actcgactct tctttggttg catctgttgc ttcgcggcac | 840 |
| ttaaacgaaa caaggttgca caggcagtgg ggaaataaat tgcatacttt ctgtataggc | 900 |
| ttgaagggtt ctcctgatct taaagctgct agagaagttg ctgattacct cagcactgta | 960 |
| catcatgagt tccacttcac agtgcaggag ggcattgatg ccttggaaga agtcatctac | 1020 |
| catattgaga catatgatgt tacaacaatc agagcaagta ccccaatgtt tttgatgtca | 1080 |
| cgcaaaatca aatctttggg tgtgaagatg gttattctg gcgaaggttc agatgaaatt | 1140 |
| tttggtggtt accttttattt tcacaaggca ccaaacaaga agaattcca tgaggaaaca | 1200 |
| tgtcggaaga taaaagcact acatctgtat gactgcttga gagctaacaa agcaacttct | 1260 |
| gcctggggtg ttgaggctcg tgttccattc cttgacaaaa gtttcatcag tgtagcaatg | 1320 |
| gacattgatc ctgaatggaa gatgataaaa cgtgacctcg gtcgaattga gaaatgggtt | 1380 |
| atccgtaatg catttgatga tgatgagagg ccctatttac ctaagcacat tctctacagg | 1440 |
| caaaaggaac agttcagtga tggtgttggg tatagttgga tcgatggatt gaaggaccat | 1500 |
| gccagccaac atgtctccga ttccatgatg atgaatgctg gctttgttta cccagagaac | 1560 |
| acacccacaa caaagaagg gtactactac agaatgatat cgagaaatt ctttcccaag | 1620 |
| cctgcagcaa ggtcaactgt tcctggaggt cctagtgtgg cctgcagcac tgccaaagct | 1680 |
| gttgaatggg acgcatcctg gtccaagaac cttgatcctt ctggccgtgc tgctttgggt | 1740 |
| gttcacgatg ctgcgtatga agacactgca gggaaaactc ctgcctctgc tgatcctgtc | 1800 |
| tcagacaagg gccttcgtcc agctattggc gaaagcctag gacacccgt tgcttcagcc | 1860 |
| acagctgtc | 1869 |

<210> SEQ ID NO 2
<211> LENGTH: 623
<212> TYPE: PRT
<213> ORGANISM: Zea mays

<400> SEQUENCE: 2

Met Ile Cys Asp Lys Cys Ser Leu Val Arg Ser Phe Phe Val Gly Arg
1               5                   10                  15

Pro Arg Asp Ile Thr Ser Leu Tyr Lys Lys Ala Gly Ser Cys Arg Thr
            20                  25                  30

Met Cys Gly Ile Leu Ala Val Leu Gly Val Ala Glu Val Ser Leu Ala

```
            35                  40                  45
Lys Arg Ser Arg Ile Ile Glu Leu Ser Arg Arg Leu Arg His Arg Gly
 50                  55                  60

Pro Asp Trp Ser Gly Leu His Cys His Glu Asp Cys Tyr Leu Ala His
 65                  70                  75                  80

Gln Arg Leu Ala Ile Ile Asp Pro Thr Ser Gly Asp Gln Pro Leu Tyr
                     85                  90                  95

Asn Glu Asp Lys Thr Val Val Thr Val Asn Gly Glu Ile Tyr Asn
                100                 105                 110

His Glu Glu Leu Lys Ala Lys Leu Lys Thr His Glu Phe Gln Thr Gly
                115                 120                 125

Ser Asp Cys Glu Val Ile Ala His Leu Tyr Glu Glu Tyr Gly Glu Glu
                130                 135                 140

Phe Val Asp Met Leu Asp Gly Met Phe Ser Phe Val Leu Leu Asp Thr
145                 150                 155                 160

Arg Asp Lys Ser Phe Ile Ala Ala Arg Asp Ala Ile Gly Ile Cys Pro
                    165                 170                 175

Leu Tyr Met Gly Trp Gly Leu Asp Gly Ser Val Trp Phe Ser Ser Glu
                180                 185                 190

Met Lys Ala Leu Ser Asp Asp Cys Glu Arg Phe Ile Thr Phe Pro Pro
                195                 200                 205

Gly His Leu Tyr Ser Ser Lys Thr Gly Gly Leu Arg Arg Trp Tyr Asn
210                 215                 220

Pro Pro Trp Phe Ser Glu Thr Val Pro Ser Thr Pro Tyr Asn Ala Leu
225                 230                 235                 240

Phe Leu Arg Glu Met Phe Glu Lys Ala Val Ile Lys Arg Leu Met Thr
                    245                 250                 255

Asp Val Pro Phe Gly Val Leu Leu Ser Gly Gly Leu Asp Ser Ser Leu
                260                 265                 270

Val Ala Ser Val Ala Ser Arg His Leu Asn Glu Thr Lys Val Asp Arg
                275                 280                 285

Gln Trp Gly Asn Lys Leu His Thr Phe Cys Ile Gly Leu Lys Gly Ser
290                 295                 300

Pro Asp Leu Lys Ala Ala Arg Glu Val Ala Asp Tyr Leu Ser Thr Val
305                 310                 315                 320

His His Glu Phe His Phe Thr Val Gln Glu Gly Ile Asp Ala Leu Glu
                    325                 330                 335

Glu Val Ile Tyr His Ile Glu Thr Tyr Asp Val Thr Thr Ile Arg Ala
                340                 345                 350

Ser Thr Pro Met Phe Leu Met Ser Arg Lys Ile Lys Ser Leu Gly Val
                355                 360                 365

Lys Met Val Ile Ser Gly Glu Gly Ser Asp Glu Ile Phe Gly Gly Tyr
                370                 375                 380

Leu Tyr Phe His Lys Ala Pro Asn Lys Lys Glu Phe His Glu Glu Thr
385                 390                 395                 400

Cys Arg Lys Ile Lys Ala Leu His Leu Tyr Asp Cys Leu Arg Ala Asn
                    405                 410                 415

Lys Ala Thr Ser Ala Trp Gly Val Glu Ala Arg Val Pro Phe Leu Asp
                420                 425                 430

Lys Ser Phe Ile Ser Val Ala Met Asp Ile Asp Pro Glu Trp Lys Met
                435                 440                 445

Ile Lys Arg Asp Leu Gly Arg Ile Glu Lys Trp Val Ile Arg Asn Ala
450                 455                 460
```

```
Phe Asp Asp Asp Glu Arg Pro Tyr Leu Pro Lys His Ile Leu Tyr Arg
465                 470                 475                 480

Gln Lys Glu Gln Phe Ser Asp Gly Val Gly Tyr Ser Trp Ile Asp Gly
            485                 490                 495

Leu Lys Asp His Ala Ser Gln His Val Ser Asp Ser Met Met Met Asn
        500                 505                 510

Ala Gly Phe Val Tyr Pro Glu Asn Thr Pro Thr Lys Glu Gly Tyr
        515                 520                 525

Tyr Tyr Arg Met Ile Phe Glu Lys Phe Phe Pro Lys Pro Ala Ala Arg
530                 535                 540

Ser Thr Val Pro Gly Gly Pro Ser Val Ala Cys Ser Thr Ala Lys Ala
545                 550                 555                 560

Val Glu Trp Asp Ala Ser Trp Ser Lys Asn Leu Asp Pro Ser Gly Arg
            565                 570                 575

Ala Ala Leu Gly Val His Asp Ala Ala Tyr Glu Asp Thr Ala Gly Lys
            580                 585                 590

Thr Pro Ala Ser Ala Asp Pro Val Ser Asp Lys Gly Leu Arg Pro Ala
        595                 600                 605

Ile Gly Glu Ser Leu Gly Thr Pro Val Ala Ser Ala Thr Ala Val
        610                 615                 620

<210> SEQ ID NO 3
<211> LENGTH: 1818
<212> TYPE: DNA
<213> ORGANISM: Zea mays

<400> SEQUENCE: 3
atgtgcggca tacttgctgt gctcgggtgc gccgacgagg ccaagggcag cagcaagagg      60
tcccgggtgc tggagctgtc gcggcggctg aagaccggg gccccgactg gagcggcctc     120
cggcaggtgg gcgactgcta cctctctcac cagcgcctcg ccatcatcga cccggcctct     180
ggcgaccagc ccctctacaa cgaggaccag tcggtggtcg tcgccgtcaa cggcgagatc     240
tacaaccacc tggacctcag gagccgcctc gccggcgcag ccacagctt caggaccggc     300 agcgactgcg aggtcatcgc gcacctgtac gaggagcatg gagaagagtt cgtggacatg     360
ctggacggcg tcttctcctt cgtgctgctg gacactcgcc atggcgaccg gcgggcagc     420 agcttcttca tggctgctcg cgacgccatc ggtgtgacgc cctctacat cggatgggga     480 gtcgatgggt cggtgtggat ttcgtcggag atgaaggccc tgcacgacga gtgtgagcac     540
ttcgagatct ccctccggg gcatctctac tccagcaaca ccggcggatt cagcaggtgg     600
tacaaccctc cttggtacga cgacgacgac gacgaggagg ccgtcgtcac ccctccgtc     660 ccctacgacc cgctggcgct aaggaaggcg ttcgagaagg ccgtggtgaa gcggctgatg     720
acagacgtcc cgttcggcgt cctgctctcc ggcgggctgg actcgtcgct ggtggcgacc     780
gtcgccgtgc gccacctcgc ccggacagag gccgccaggc gctggggcac caagctccac     840
tccttctgcg tgggcctgga ggggtcccct gacctcaagg cggccaggga ggtggcggag     900
tacctgggca ccctgcacca tgagttccac ttcactgttc aggacggcat cgacgccatc     960
gaggacgtga tctaccacac ggagacgtac gacgtcacca cgatcagggc gagcacgccc    1020
atgttcctca tgtcgcgcaa gatcaagtcg ctcggggtca gatggtcat ctccggcgag    1080 ggctccgacg agctcttcgg aggctacctc tacttccaca aggcgcccaa caaggaggag    1140
ttgcaccgag agacgtgtag gaaggttaag gctctgcatc agtacgactg cctgagagcc    1200
```

```
aacaaggcga catcagcttg gggcctggag gctcgcgtcc cgttcctgga caaggagttc    1260
atcaatgcgg ccatgagcat cgatcctgag tggaagatgg tccagcctga tcttggaagg    1320
attgagaagt gggtgctgag gaaggcattc gacgacgagg agcagccatt cctgcccaag    1380
catatcctct acagacagaa ggagcagttc agtgacggcg ttgggtacag ctggatcgat    1440
ggcctgaagg ctcatgcaac atcaaatgtg actgacaaga tgctgtcaaa tgcaaagttc    1500
atcttcccac acaacactcc gaccaccaag gaggcctact actacaggat ggtcttcgag    1560
aggttcttcc cacagaaatc tgctatcctg acggtacctg gtgggccaag tgtggcgtgc    1620
agcacagcca aagccatcga gtgggacgca caatggtcag gaaatctgga ccccctcggga   1680 agggcggcac tgggcgtcca tctcgccgcc tacgaacacc aacatgatcc cgagcatgtc    1740
ccggcggcca ttgcagcagg aagcggcaag aagccaagga cgattagggt ggcaccgcct    1800
ggcgttgcca tcgaggga                                                  1818

<210> SEQ ID NO 4
<211> LENGTH: 606
<212> TYPE: PRT
<213> ORGANISM: Zea mays

<400> SEQUENCE: 4

Met Cys Gly Ile Leu Ala Val Leu Gly Cys Ala Asp Glu Ala Lys Gly
1               5                   10                  15

Ser Ser Lys Arg Ser Arg Val Leu Glu Leu Ser Arg Arg Leu Lys His
            20                  25                  30

Arg Gly Pro Asp Trp Ser Gly Leu Arg Gln Val Gly Asp Cys Tyr Leu
        35                  40                  45

Ser His Gln Arg Leu Ala Ile Ile Asp Pro Ala Ser Gly Asp Gln Pro
    50                  55                  60

Leu Tyr Asn Glu Asp Gln Ser Val Val Val Ala Val Asn Gly Glu Ile
65                  70                  75                  80

Tyr Asn His Leu Asp Leu Arg Ser Arg Leu Ala Gly Ala Gly His Ser
                85                  90                  95

Phe Arg Thr Gly Ser Asp Cys Glu Val Ile Ala His Leu Tyr Glu Glu
            100                 105                 110

His Gly Glu Glu Phe Val Asp Met Leu Asp Gly Val Phe Ser Phe Val
        115                 120                 125

Leu Leu Asp Thr Arg His Gly Asp Arg Ala Gly Ser Ser Phe Phe Met
    130                 135                 140

Ala Ala Arg Asp Ala Ile Gly Val Thr Pro Leu Tyr Ile Gly Trp Gly
145                 150                 155                 160

Val Asp Gly Ser Val Trp Ile Ser Ser Glu Met Lys Ala Leu His Asp
                165                 170                 175

Glu Cys Glu His Phe Glu Ile Phe Pro Pro Gly His Leu Tyr Ser Ser
            180                 185                 190

Asn Thr Gly Gly Phe Ser Arg Trp Tyr Asn Pro Pro Trp Tyr Asp Asp
        195                 200                 205

Asp Asp Asp Glu Glu Ala Val Val Thr Pro Ser Val Pro Tyr Asp Pro
    210                 215                 220

Leu Ala Leu Arg Lys Ala Phe Glu Lys Ala Val Lys Arg Leu Met
225                 230                 235                 240

Thr Asp Val Pro Phe Gly Val Leu Leu Ser Gly Gly Leu Asp Ser Ser
                245                 250                 255

Leu Val Ala Thr Val Ala Val Arg His Leu Ala Arg Thr Glu Ala Ala
```

```
                260                 265                 270
Arg Arg Trp Gly Thr Lys Leu His Ser Phe Cys Val Gly Leu Glu Gly
            275                 280                 285

Ser Pro Asp Leu Lys Ala Ala Arg Glu Val Ala Glu Tyr Leu Gly Thr
        290                 295                 300

Leu His His Glu Phe His Phe Thr Val Gln Asp Gly Ile Asp Ala Ile
305                 310                 315                 320

Glu Asp Val Ile Tyr His Thr Glu Thr Tyr Asp Val Thr Thr Ile Arg
                325                 330                 335

Ala Ser Thr Pro Met Phe Leu Met Ser Arg Lys Ile Lys Ser Leu Gly
            340                 345                 350

Val Lys Met Val Ile Ser Gly Glu Gly Ser Asp Glu Leu Phe Gly Gly
        355                 360                 365

Tyr Leu Tyr Phe His Lys Ala Pro Asn Lys Glu Leu His Arg Glu
    370                 375                 380

Thr Cys Arg Lys Val Lys Ala Leu His Gln Tyr Asp Cys Leu Arg Ala
385                 390                 395                 400

Asn Lys Ala Thr Ser Ala Trp Gly Leu Glu Ala Arg Val Pro Phe Leu
                405                 410                 415

Asp Lys Glu Phe Ile Asn Ala Ala Met Ser Ile Asp Pro Glu Trp Lys
            420                 425                 430

Met Val Gln Pro Asp Leu Gly Arg Ile Glu Lys Trp Val Leu Arg Lys
        435                 440                 445

Ala Phe Asp Asp Glu Glu Gln Pro Phe Leu Pro Lys His Ile Leu Tyr
    450                 455                 460

Arg Gln Lys Glu Gln Phe Ser Asp Gly Val Gly Tyr Ser Trp Ile Asp
465                 470                 475                 480

Gly Leu Lys Ala His Ala Thr Ser Asn Val Thr Asp Lys Met Leu Ser
                485                 490                 495

Asn Ala Lys Phe Ile Phe Pro His Asn Thr Pro Thr Thr Lys Glu Ala
            500                 505                 510

Tyr Tyr Tyr Arg Met Val Phe Glu Arg Phe Phe Pro Gln Lys Ser Ala
        515                 520                 525

Ile Leu Thr Val Pro Gly Gly Pro Ser Val Ala Cys Ser Thr Ala Lys
    530                 535                 540

Ala Ile Glu Trp Asp Ala Gln Trp Ser Gly Asn Leu Asp Pro Ser Gly
545                 550                 555                 560

Arg Ala Ala Leu Gly Val His Leu Ala Ala Tyr Glu His Gln His Asp
                565                 570                 575

Pro Glu His Val Pro Ala Ala Ile Ala Ala Gly Ser Gly Lys Lys Pro
            580                 585                 590

Arg Thr Ile Arg Val Ala Pro Pro Gly Val Ala Ile Glu Gly
        595                 600                 605

<210> SEQ ID NO 5
<211> LENGTH: 1764
<212> TYPE: DNA
<213> ORGANISM: Zea mays

<400> SEQUENCE: 5
atgtgtggca tcttagccgt gctcggttgc tccgactggt ctcaggcaaa gagggctcgc        60
atcctcgcct gctccagaag gttgaagcac aggggcccg actggtcggg cctttaccag       120
cacgagggca acttcctggc gcagcagcgg ctcgccgtcg tctccccgct gtccggcgac       180
```

```
cagccgctgt tcaacgagga ccgcaccgtc gtggtggtgg ccaatggaga gatctacaac    240
cacaagaacg tccggaagca gttcaccggc acacacaact tcagcacggg cagtgactgc    300
gaggtcatca tgcccctgta cgagaagtac ggcgagaact tcgtggacat gctggacggg    360
gtgttcgcgt tcgtgctcta cgacaccgc gacaggacct acgtggcggc gcgcgacgcc    420
atcggcgtca accgctcta catcggctgg ggcagtgacg gttccgtctg gatcgcgtcc    480
gagatgaagg cgctgaacga ggactgcgtg cgcttcgaga tcttcccgcc gggccacctc    540
tactccagcg ccggcggcgg gttccggcgg tggtacaccc cgcactggtt ccaggagcag    600
gtgccccgga cgccgtacca gccgctcgtc ctcagagagg ccttcgagaa ggcggtcatc    660
aagaggctca tgactgacgt cccgttcggg gtcctcctct ccggcggcct cgactcctcg    720
ctagtcgcct ccgtcaccaa gcgccacctc gtcgagaccg aggccgccga aagttcggc    780 accgagctcc actcctttgt cgtcggcctc gagggctccc ctgacctgaa ggccgcacga    840
gaggtcgctg actacctcgg aaccatccat cacgagttcc acttcaccgt acaggacggc    900
atcgacgcga tcgaggaggt gatctaccac gacgagacgt acgacgtgac gacgatccgg    960
gccagcacgc ccatgttcct gatggctcgc aagatcaagt cgctgggcgt gaagatggtg   1020
ctgtccgggg agggctccga cgagctcctg ggcggctacc tctacttcca cttcgccccc   1080
aacaaggagg agttccacag ggagacctgc cgcaaggtga agccctgca ccagtacgac   1140 tgcctgcgcg ccaacaaggc cacgtcggcg tggggcctgg aggtccgcgt gccgttcctc   1200
gacaaggagt tcatcaacgt cgccatgggc atggaccccg aatggaaaat gtacgacaag   1260
aacctgggcc gcatcgagaa gtgggtcatg aggaaggcgt cgacgacga cgagcaccct   1320 tacctgccca agcatattct ctaccggcag aaagaacagt tcagtgacgg cgttggctac   1380
aactggatcg atggccttaa atccttcact gaacagcagg tgacggatga gatgatgaac   1440
aacgccgccc agatgttccc ctacaacacg cccgtcaaca aggaggccta ctactaccgg   1500
atgatattcg agaggctctt ccctcaggac tcggcgaggg agacggtgcc gtggggcccg   1560
agcatcgcct gcagcacgcc cgcggccatc gagtgggtgg agcagtggaa ggcctccaac   1620
gacccctccg ccgccttcat ctcctcccac gactccgccg ccaccgacca caccggcggt   1680
aagccggcgg tggccaacgg cggcggccac ggcgcggcga acggcacggt caacggcaag   1740
gacgtcgcag tcgcgatcgc ggtc                                          1764
```

<210> SEQ ID NO 6
<211> LENGTH: 588
<212> TYPE: PRT
<213> ORGANISM: Zea mays

<400> SEQUENCE: 6

```
Met Cys Gly Ile Leu Ala Val Leu Gly Cys Ser Asp Trp Ser Gln Ala
1               5                   10                  15

Lys Arg Ala Arg Ile Leu Ala Cys Ser Arg Arg Leu Lys His Arg Gly
            20                  25                  30

Pro Asp Trp Ser Gly Leu Tyr Gln His Glu Gly Asn Phe Leu Ala Gln
        35                  40                  45

Gln Arg Leu Ala Val Val Ser Pro Leu Ser Gly Asp Gln Pro Leu Phe
    50                  55                  60

Asn Glu Asp Arg Thr Val Val Val Ala Asn Gly Glu Ile Tyr Asn
65                  70                  75                  80

His Lys Asn Val Arg Lys Gln Phe Thr Gly Thr His Asn Phe Ser Thr
                85                  90                  95
```

```
Gly Ser Asp Cys Glu Val Ile Met Pro Leu Tyr Glu Lys Tyr Gly Glu
            100                 105                 110

Asn Phe Val Asp Met Leu Asp Gly Val Phe Ala Phe Val Leu Tyr Asp
        115                 120                 125

Thr Arg Asp Arg Thr Tyr Val Ala Ala Arg Asp Ala Ile Gly Val Asn
130                 135                 140

Pro Leu Tyr Ile Gly Trp Gly Ser Asp Gly Ser Val Trp Ile Ala Ser
145                 150                 155                 160

Glu Met Lys Ala Leu Asn Glu Asp Cys Val Arg Phe Glu Ile Phe Pro
                165                 170                 175

Pro Gly His Leu Tyr Ser Ser Ala Gly Gly Phe Arg Arg Trp Tyr
            180                 185                 190

Thr Pro His Trp Phe Gln Glu Gln Val Pro Arg Thr Pro Tyr Gln Pro
        195                 200                 205

Leu Val Leu Arg Glu Ala Phe Glu Lys Ala Val Ile Lys Arg Leu Met
    210                 215                 220

Thr Asp Val Pro Phe Gly Val Leu Leu Ser Gly Leu Asp Ser Ser
225                 230                 235                 240

Leu Val Ala Ser Val Thr Lys Arg His Leu Val Glu Thr Glu Ala Ala
                245                 250                 255

Glu Lys Phe Gly Thr Glu Leu His Ser Phe Val Gly Leu Glu Gly
            260                 265                 270

Ser Pro Asp Leu Lys Ala Ala Arg Glu Val Ala Asp Tyr Leu Gly Thr
        275                 280                 285

Ile His His Glu Phe His Phe Thr Val Gln Asp Gly Ile Asp Ala Ile
    290                 295                 300

Glu Glu Val Ile Tyr His Asp Glu Thr Tyr Asp Val Thr Thr Ile Arg
305                 310                 315                 320

Ala Ser Thr Pro Met Phe Leu Met Ala Arg Lys Ile Lys Ser Leu Gly
                325                 330                 335

Val Lys Met Val Leu Ser Gly Glu Gly Ser Asp Glu Leu Leu Gly Gly
            340                 345                 350

Tyr Leu Tyr Phe His Phe Ala Pro Asn Lys Glu Glu Phe His Arg Glu
        355                 360                 365

Thr Cys Arg Lys Val Lys Ala Leu His Gln Tyr Asp Cys Leu Arg Ala
370                 375                 380

Asn Lys Ala Thr Ser Ala Trp Gly Leu Glu Val Arg Val Pro Phe Leu
385                 390                 395                 400

Asp Lys Glu Phe Ile Asn Val Ala Met Gly Met Asp Pro Glu Trp Lys
                405                 410                 415

Met Tyr Asp Lys Asn Leu Gly Arg Ile Glu Lys Trp Val Met Arg Lys
            420                 425                 430

Ala Phe Asp Asp Glu His Pro Tyr Leu Pro Lys His Ile Leu Tyr
        435                 440                 445

Arg Gln Lys Glu Gln Phe Ser Asp Gly Val Gly Tyr Asn Trp Ile Asp
    450                 455                 460

Gly Leu Lys Ser Phe Thr Glu Gln Gln Val Thr Asp Glu Met Met Asn
465                 470                 475                 480

Asn Ala Ala Gln Met Phe Pro Tyr Asn Thr Pro Val Asn Lys Glu Ala
                485                 490                 495

Tyr Tyr Tyr Arg Met Ile Phe Glu Arg Leu Phe Pro Gln Asp Ser Ala
            500                 505                 510
```

Arg Glu Thr Val Pro Trp Gly Pro Ser Ile Ala Cys Ser Thr Pro Ala
            515                 520                 525

Ala Ile Glu Trp Val Glu Gln Trp Lys Ala Ser Asn Asp Pro Ser Gly
        530                 535                 540

Arg Phe Ile Ser Ser His Asp Ser Ala Ala Thr Asp His Thr Gly Gly
545                 550                 555                 560

Lys Pro Ala Val Ala Asn Gly Gly His Gly Ala Ala Asn Gly Thr
                565                 570                 575

Val Asn Gly Lys Asp Val Ala Val Ala Ile Ala Val
            580                 585

<210> SEQ ID NO 7
<211> LENGTH: 1743
<212> TYPE: DNA
<213> ORGANISM: Glycine max

<400> SEQUENCE: 7

| | | | | | |
|---|---|---|---|---|---|
| atgtgtggta | ttcttgctgt | tcttggttgt | tctgatgact | ctcgagccaa | aagggtccgc | 60 |
| gtgcttgagc | tctctcgcag | attgaagcac | cgtggccctg | actggagtgg | gctccatcaa | 120 |
| catggtgact | gcttttttggc | acatcaacgg | ttagccatag | ttgatcctgc | ttctggggat | 180 |
| caacctctct | ttaacgagga | caaatccgtc | attgttacgg | taaatggaga | gatttacaac | 240 |
| catgaagagc | tcaggaaaca | gctgcctaat | cacaacttcc | gaactggaag | tgattgtgat | 300 |
| gttattgcac | acctgtacga | ggaacatgga | gaagactttg | tggacatgct | ggatggtatc | 360 |
| ttctcatttg | ttctactgga | cacccgtgac | aacagtttta | tagtggctcg | ggatgctatt | 420 |
| ggggtcactt | ccttgtacat | tggatggggg | ttagatggct | ctgtttggat | ttcatcagaa | 480 |
| atgaaaggcc | tgaatgatga | ttgtgaacac | tttgagtgtt | tccacctgg | tcacttgtac | 540 |
| tctagcaaag | aaagagggtt | ccgcagatgg | tacaatcctc | cttggttctc | tgaggctatt | 600 |
| ccatctgccc | cttatgatcc | tcttgtttta | agacacgcct | tgagcaggc | agtcataaaa | 660 |
| aggttgatga | ctgatgtgcc | ttttggtgtt | ctactctctg | gaggtttgga | ctcttctttg | 720 |
| gttgcatcca | tcacttctcg | ttacttggcc | aacacaaagg | ctgctgagca | gtggggatca | 780 |
| aagttacatt | cattctgtgt | aggccttgag | ggctcaccag | atttgaaggc | tgcaaaagag | 840 |
| gttgctgact | atctaggcac | tgtccaccat | gagtttacct | tcactgttca | ggatggaata | 900 |
| gatgccattg | aagatgttat | ctaccatatt | gaaacatatg | atgtgactac | aattagagca | 960 |
| agcacaccta | tgtttctcat | gtctcggaag | attaaatcac | ttggtgtcaa | atgggttatc | 1020 |
| tcaggagaag | gatctgatga | gatctttgga | gggtatttgt | acttccacaa | ggcacccaac | 1080 |
| aaggaggagt | tccacagaga | aacatgccgc | aagatcaaag | cacttcacca | atatgattgc | 1140 |
| ttgcgagcca | ataaatcaac | atttgcttgg | ggtctagaag | cccgtgtacc | attttggac | 1200 |
| aaggcgtttta | tcaatgctgc | aatgagtatt | gaccctgagt | ggaagatgat | aaaaagagat | 1260 |
| gaaggacgaa | ttgagaagtg | gattctgagg | agagcctttg | atgatgaaga | gcatccttat | 1320 |
| ctgccaaagc | acatttttata | caggcagaaa | gaacaattca | gtgatggagt | tggctatagt | 1380 |
| tggattgatg | gccttaaggc | ccatgctgca | aacatgtgta | ctgaaaaaat | gatgcttaat | 1440 |
| gctggtaaca | tttacccccca | caacaccccca | aaaaccaagg | aagcatatta | ctacagaatg | 1500 |
| atctttgaga | ggttcttccc | tcagaactca | gctaggctca | ctgttcctgg | aggagcaagt | 1560 |
| gttgcatgta | gcacagccaa | agctgttgag | tgggatgctg | cttggtctaa | caaccttgat | 1620 |
| ccctctggta | gagcagcact | tggagtgcac | atttcagcct | atgaaaaacca | gaacaacaag | 1680 |

```
ggtgtagaaa ttgagaagat aatacctatg gatgctgctc cccttggtgt tgccatccag    1740
ggc                                                                 1743
```

<210> SEQ ID NO 8
<211> LENGTH: 581
<212> TYPE: PRT
<213> ORGANISM: Glycine max

<400> SEQUENCE: 8

```
Met Cys Gly Ile Leu Ala Val Leu Gly Cys Ser Asp Asp Ser Arg Ala
1               5                   10                  15

Lys Arg Val Arg Val Leu Glu Leu Ser Arg Arg Leu Lys His Arg Gly
                20                  25                  30

Pro Asp Trp Ser Gly Leu His Gln His Gly Asp Cys Phe Leu Ala His
            35                  40                  45

Gln Arg Leu Ala Ile Val Asp Pro Ala Ser Gly Asp Gln Pro Leu Phe
        50                  55                  60

Asn Glu Asp Lys Ser Val Ile Val Thr Val Asn Gly Glu Ile Tyr Asn
65                  70                  75                  80

His Glu Glu Leu Arg Lys Gln Leu Pro Asn His Asn Phe Arg Thr Gly
                85                  90                  95

Ser Asp Cys Asp Val Ile Ala His Leu Tyr Glu Glu His Gly Glu Asp
            100                 105                 110

Phe Val Asp Met Leu Asp Gly Ile Phe Ser Phe Val Leu Leu Asp Thr
        115                 120                 125

Arg Asp Asn Ser Phe Ile Val Ala Arg Asp Ala Ile Gly Val Thr Ser
    130                 135                 140

Leu Tyr Ile Gly Trp Gly Leu Asp Gly Ser Val Trp Ile Ser Ser Glu
145                 150                 155                 160

Met Lys Gly Leu Asn Asp Asp Cys Glu His Phe Glu Cys Phe Pro Pro
                165                 170                 175

Gly His Leu Tyr Ser Ser Lys Glu Arg Gly Phe Arg Arg Trp Tyr Asn
            180                 185                 190

Pro Pro Trp Phe Ser Glu Ala Ile Pro Ser Ala Pro Tyr Asp Pro Leu
        195                 200                 205

Val Leu Arg His Ala Phe Glu Gln Ala Val Ile Lys Arg Leu Met Thr
    210                 215                 220

Asp Val Pro Phe Gly Val Leu Leu Ser Gly Gly Leu Asp Ser Ser Leu
225                 230                 235                 240

Val Ala Ser Ile Thr Ser Arg Tyr Leu Ala Asn Thr Lys Ala Ala Glu
                245                 250                 255

Gln Trp Gly Ser Lys Leu His Ser Phe Cys Val Gly Leu Glu Gly Ser
            260                 265                 270

Pro Asp Leu Lys Ala Ala Lys Glu Val Ala Asp Tyr Leu Gly Thr Val
        275                 280                 285

His His Glu Phe Thr Phe Thr Val Gln Asp Gly Ile Asp Ala Ile Glu
    290                 295                 300

Asp Val Ile Tyr His Ile Glu Thr Tyr Asp Val Thr Thr Ile Arg Ala
305                 310                 315                 320

Ser Thr Pro Met Phe Leu Met Ser Arg Lys Ile Lys Ser Leu Gly Val
                325                 330                 335

Lys Trp Val Ile Ser Gly Glu Gly Ser Asp Glu Ile Phe Gly Gly Tyr
            340                 345                 350

Leu Tyr Phe His Lys Ala Pro Asn Lys Glu Glu Phe His Arg Glu Thr
```

```
                355                 360                 365
Cys Arg Lys Ile Lys Ala Leu His Gln Tyr Asp Cys Leu Arg Ala Asn
        370                 375                 380
Lys Ser Thr Phe Ala Trp Gly Leu Glu Ala Arg Val Pro Phe Leu Asp
385                 390                 395                 400
Lys Ala Phe Ile Asn Ala Ala Met Ser Ile Asp Pro Glu Trp Lys Met
                405                 410                 415
Ile Lys Arg Asp Glu Gly Arg Ile Glu Lys Trp Ile Leu Arg Arg Ala
            420                 425                 430
Phe Asp Asp Glu Glu His Pro Tyr Leu Pro Lys His Ile Leu Tyr Arg
        435                 440                 445
Gln Lys Glu Gln Phe Ser Asp Gly Val Gly Tyr Ser Trp Ile Asp Gly
    450                 455                 460
Leu Lys Ala His Ala Ala Lys His Val Thr Glu Lys Met Met Leu Asn
465                 470                 475                 480
Ala Gly Asn Ile Tyr Pro His Asn Thr Pro Lys Thr Lys Glu Ala Tyr
                485                 490                 495
Tyr Tyr Arg Met Ile Phe Glu Arg Phe Phe Pro Gln Asn Ser Ala Arg
            500                 505                 510
Leu Thr Val Pro Gly Gly Ala Ser Val Ala Cys Ser Thr Ala Lys Ala
        515                 520                 525
Val Glu Trp Asp Ala Ala Trp Ser Asn Asn Leu Asp Pro Ser Gly Arg
    530                 535                 540
Ala Ala Leu Gly Val His Ile Ser Ala Tyr Glu Asn Gln Asn Asn Lys
545                 550                 555                 560
Gly Val Glu Ile Glu Lys Ile Ile Pro Met Asp Ala Ala Pro Leu Gly
                565                 570                 575
Val Ala Ile Gln Gly
            580

<210> SEQ ID NO 9
<211> LENGTH: 1785
<212> TYPE: DNA
<213> ORGANISM: Xylella fastidiosa

<400> SEQUENCE: 9
atgatttgtg acaaatgcag cctcgtgcgg agctttttttg taggtagacc gcgggatatc    60
acaagtttgt acaaaaaagc aggctcctgc aggaccatgt gttccatttt tggaatcttc   120
aacctgcaac ccagtgacaa cctacagata ctgcgtcacc aagcattgga gtgctcgcaa   180
cggcaacggc atcgcggacc cgattggagc ggcgtttacg ttgatgtggg tgcgattctg   240
gtgcacgaac gtcttgctat cgttgatcca gctggcggtg cccagccact gctctccgag   300
gatggcaccc tggcgttggc ggtcaacggc gaaatctata ccacgctgt actcaaagga   360
acattgcagc agcctatgc gttccaaact cattctgatt gcaagtgat taatgcgctt   420
taccgcgaag aaactccaac ctcgtttctg aatcgcttaa atgggatttt tgcattcgta   480
ttatgggaca agactaccgg acgtggcctc atcgcacgcg atccaatggg tgtggtgccg   540
ctgtactggg ggcacgatca ggacggtcgc ttacgtgtcg cgtcagagat gaaagcattg   600
gttgagcatt gctccgacgt tgcacaattc ccaccggcc attggtacga caccacaacg   660
ggcacgctgg tgaagtatta cgaacgcccc tggaaaaaact attctgcagt ggaaggagtg   720
caggtctcac tacaggaact gcgtgaagcg ttcgagcggg ccgtccatcg tcaactcatg   780
acagatgttc catacggtgt actgctttct ggtggattgg attcttccct ggtggctgcg   840
```

-continued

```
gtggccgcac gctacgcacg ccatcgcatc gaaaccaatg atcagagcga agcatggtgg    900
ccacgtctgc actcatttgc gattggactg aaagactcgc cagatttgag tgcggcgaac    960
gtggctgctg aggcgttgaa taccgtccac catcgtttcg agtacacctt ccaggagggg   1020
ctggatgttc tacctgaagt gattcgtcac attgaaactt acgatgtcac gacgattcgc   1080
gcatctacac caatgttcct gctggcacgt cgcattaagg cgatgggagt gaagatggtc   1140
ttgtcaggtg aaggtagcga tgaaattttt ggcggttacc tgtacttcca caaagcgccg   1200
aacgcacgcg agttccacga agaattggtc cgtaagctca acgccctgta ttactacgac   1260
tgcttgcgcg ccaacaaagc gatgatggcg tggggtgtcg agccgcgcgt gccgtttttg   1320
gaccgtgaat ttctcgatgt ggctatgcgg atggatgctc agcataagat ggtcgacaag   1380
accagcaacg gcccacaacg gatggagaaa ggcatcctgc gtgcagcgtt tgacggctat   1440
ttgccgccat caatcctgtg gcgacagaag gagcagttca gtgatggtgt tggctacggt   1500
tggatcgacg gactgaaagc acacgctgaa acgcaagtgt ctgaccatgc gctggcaact   1560
gccgagacac gtttccaggt gaatcctccc cagaccaaag aagcctatta ctaccgcagc   1620
atatttgagc gcttcttccc aagcccggcg gcggctgaga cggtaccggg cggtaaatca   1680
attgcctgtt cctcaccggc ggcgattgcc tgggatgcca gcttcgccac aatggctgac   1740
ccatccggtc gtgcagtcag cggggttcat caacaagcac tgctg                   1785
```

<210> SEQ ID NO 10
<211> LENGTH: 1779
<212> TYPE: DNA
<213> ORGANISM: Xanthomonas campestris

<400> SEQUENCE: 10

```
atgatttgtg acaaatgcag cctcgtgcgg agctttttttg taggtagacc gcggaccggt     60
cgcgcctcag cagtcgctgt cgttaccatg tgttccatct tcggtatctt cggcctgcaa    120
cccggcgacg acctgcaggc cctgcgccgg caggccctgg aatgttcgca gcggcaacgc    180
catcgcgggc cggactggag cggcgtgtac gtcgatgccg gtgccatcct ggtgcacgag    240
cgcctggcca tcgtcgaccc ggcgggcggt tcgcagccgc tgttgtcgga ggacggcagc    300
ctggcgttgg cagtcaacgg cgagatctat aaccatcgcg aactcaaggc cgagctactg    360
cagccgtacg cttttcagac cggctcggac tgcgaagtga tcaacgcgct gtaccgcgaa    420
gatgcgccgg cctcctatct caaccgcctc aatggcatct tcgcctttgc gttgtgggac    480
aaggccgcgg ggcgggtgat catcgcgcgc gacccgattg gcgtggtgcc gttgtactgg    540
ggacacgacc gcgaaggccg tctgcgcgtg gcgtccgaac tcaagtcgct ggtggacgat    600
tgcgccgatg ctgcgcagtt tccgcctggt cattggtacg acagcgccac cggcgcattg    660
agccgctact acgagcgctc gtggcgcgaa tacagcgaag tggaaaatgt gcaggtgccg    720
ctgcaggaac tgcgcgaggc gttcgagcgc gcggtgcatc gccagctgat gaccgacgtg    780
ccctacggtg tgctgctgtc cggtggcctg gattcgtcgt tggtggcggc agtggccgcg    840
cgctacgcgc ggcatcgtat cgaagagaac gacaccaccg aagcctggtg gccgcgcctg    900
cattccttcg caatcggcct gaccggctcg ccggatctgg ccgctgccga agtggccgcc    960
gccgcgctcg gtaccgtgca ccacggcttc gaatacagct ttgaagaagg cctggatgca   1020
ttgccggaag tgatccgcca catcgaaacc tacgacgtca ccacgattcg tgcgtccacg   1080
ccgatgttcc tgctggcgcg gcgcatcaag gcgatgggcg tcaagatggt gctgtccggc   1140
```

```
gaaggcagcg acgagatctt cggtggctac ctgtacttcc acaaggcacc gaacgcccgc    1200
gaattccacg aagaactggt gcgcaagctc gatgcgctca acaactacga ttgcctgcgc    1260
gccaacaagt cgatgatggc ctggggcgtg aaccgcgcg tgccgttcct ggatcgcgaa    1320
ttcctggacg tggcgatgcg catggacgcg cgcttcaaga tgatcgacaa gaccagcacc    1380
ggtgccaccc gcatcgagaa gggcatcttg cgcgaggcat tgccggcta tctgccggaa    1440 tcgatcctgt ggcggcagaa ggagcaattc agcgatggcg ttggttatgg ctggatcgac    1500
ggcctcaagg cacatgccgc cgcgcacgtg agcgaccgcg aactcgcagc ggccgaccgg    1560
cgcttcccgg tgaacccgcc gcagaccaag gaagcctatt tctaccgcag tctgttcgag    1620
cagttcttcc ccagccaggc cgctgcggag acggtgccgg gtggtaaatc catcgcgtgt    1680
tcgtcgccga cggccattgc ctgggacgcg agctttgcgg cgatggccga tccgtcgggc    1740
cgtgcgattg ccggcgtgca cgcgcaggcg ttggcgtcc                           1779

<210> SEQ ID NO 11
<211> LENGTH: 1941
<212> TYPE: DNA
<213> ORGANISM: Bacillus halodurans

<400> SEQUENCE: 11
atgatttgtg acaaatgcag cctcgtgcgg agcttttttg taggtagacc gcgggatatc     60
acaagtttgt acaaaaaagc aggctcctgc aggaccatgt gtggaattac aggctgggta    120
gattggcgac gcaacttgca aaatgagacg gaaacgatca acagatggcg gaaacgcaa     180 acacatcgag ggcccgatga tttgaacgtt tggacagaga agcatgctgc cttaggccac    240
tcgcggctca ttgtcgttga tccggaaggc ggttgtcagc cgatgatgag ggagaggaat    300
ggcaaacgct atacgatcgt gtataacggc gaattataca atacagaaga tttacggaaa    360
gagcttatag taaaaggtta ccaatttcaa ggccattcgg atacggaagt attactcgtg    420
tcttatatcg aatggggtta ccaatgtgtg agaagttca atggcatttt tgcgtttgcg    480
atttggaatg ataaagatca gagcttgttt atggcccgcg accgattagg ggtaaagccg    540
ctattttata ctgttcgcca tggattttta cttttttgcaa ctgagataaa agcgctgctt    600
gctcatcctg aaatcgagcc ggttcttacc gaagaagggc tatcggaagt gctcgggctt    660
gggccatcac gttcaccggg taatggcgtt tttgatgata ttcaagagtt gcgaccagct    720
catcttttga catacgatcg caatggggca aaagtgagcc gttattggag attaaaatca    780
atggctcatt ctgaagatgc gatggaaacg gccgcccatc ttcgcgactt attagaagat    840
actgtcgaac gtcagctatt tgcagatgtt ccagttggaa tgtttctttc gggtggagtc    900
gattcgagtg ctttaacggc aattgcggcg ctgattacg agcgagaagg gaagggcctg    960
attcggacgt actcgattga ttatgacgaa aatgataagt attttaaagc gaatgacttt   1020
caaccgaatg ccgatggacc ttgggttgaa aaagtttcaa ctactttcg aacgaaccac   1080 cacaatgctg tcatctcgat cgaggagttg gctaatcaat aaagcgagc ggtagagctt   1140 cgtgacttac ctggaatggc cgatgtagac tcttcattgt attggttttg taagcaaatc   1200
aaaaaagatg ttaccgttgg cttatcgggt gaatgtgctg acgaaatttt tggtgggtat   1260
ccttggttcc ataagccaga ggtcatgaat tttaatgggt ttccttggat gagatcagcg   1320
gatgaacgtc aggagcttct tcatgaacga tggcgccaaa agttaaattt gcccaaatac   1380
gttcatgatc gttataaaga aacgattgcc gaaacgcctc gcttcgaaga ggacacaccg   1440
gaagaagcgc gacgcaggga atttcgtat ttgaacatgg tctggtttat gacaacgctt   1500
```

```
cttgatcgga aggatcgaat gagcatggga gcgagcttag aagtgcgagt tccattttct   1560
gaccaccgaa ttgtagaata cgcttggaac attccgtggg aaattaaaca attcggaggg   1620
agagagaagg gcattttacg aaaagcgttg gaaggcatcc tcccagatga agtgttatac   1680
cggaaaaaaa gtccttatcc gaaaacgcac catccaaaat acacgaaaat ggtccagcaa   1740
gagatggaac gaattctcgg tcaaagcgat agccccctct ttgatgtagt gaaccggaaa   1800
aagttaaaag agttaaccga aactggtggc aaggcattaa cgacaccgtta tttttgggcag 1860 cttatgacag gcccgcagct ccttgcccac ttcatccaaa tggagcattg gcttaagcat   1920
tacaatatca aattaattgg t                                            1941
```

<210> SEQ ID NO 12
<211> LENGTH: 1869
<212> TYPE: DNA
<213> ORGANISM: Oryza sativa

<400> SEQUENCE: 12

```
atgatttgtg acaaatgcag cctcgtgcgg agcttttttg taggtagacc gcgggatatc     60
acaagtttgt acaaaaaagc aggctcctgc aggaccatgt gtggcatcct cgccgtgctc    120
ggcgtcgcag acgtctccct cgtcaagcgc tcccgcatca tcgagctatc ccgccggtta    180
cgtcatagag gccctgattg gagtggtata cactgctatc aggattgcta tcttgcacac    240
cagcggttgg ctattgttga tcccacatcc ggagaccagc cgttgtacaa tgaggacaaa    300
tctgttgttg tgacggtgaa tggagagatc tataaccatg aagaattgaa agctaacctg    360
aaatctcata aattccaaac tgctagcgat tgtgaagtta ttgctcatct gtatgaggaa    420
tatggggagg aatttgtgga tatgttggat gggatgttcg cttttgttct tcttgacaca    480
cgtgataaaa gcttcattgc agcccgtgat gctattggca tttgtccttt atacatgggc    540
tggggtcttg atggttcggt ttggttttcg tcagagatga aggcattaag tgatgattgc    600
gagcgattca tatccttccc ccctgggcac ttgtactcca gcaaaacagg tggcctaagg    660
agatggtaca cccaccatg gttttctgaa agcattccct ccaccccgta caatcctctt    720
cttctccgac agagctttga gaaggctatt attaagaggc taatgacaga tgtgccattt    780
ggtgttctct tgtctggtgg actggactct tctttggttg catctgttgt tcgcggcac     840 ttggcagagg caaaagttgc cgcacagtgg ggaaacaaac tgcatacatt ttgcattggt    900
ttgaaaggtt ctcctgatct tagagctgct aaggaagttg cagactacct tggtactgtt    960
catcacgaac tccacttcac agtgcaggaa ggcattgatg cactggagga agtcatttac   1020
catgttgaga catatgatgt aacgacaatt agagcaagca ccccaatgtt cttgatgtca   1080
cgtaaaatta atctttggg ggtgaagatg gttcttcgg gagaaggttc tgatgaaata    1140
tttggcggtt acctttattt tcacaaggca ccaaacaaga aggaattcca tgaggaaaca   1200
tgtcggaaga taaagcccct tcatttatat gattgcttga gagcgaacaa atcaacttct   1260
gcatggggtg ttgaggcccg tgttccgttc cttgacaaaa acttcatcaa tgtagctatg   1320
gacattgatc ctgaatggaa aatgataaaa cgtgatcttg gccgtattga gaatggggtt   1380
ctccggaatg catttgatga tgaggagaag ccctatttac ctaagcacat tctatacagg   1440
caaaaggagc aattcagtga tggtgttggg tacagttgga ttgatggatt gaaggatcat   1500
gcaaatgaac atgtatcaga ttccatgatg atgaacgcta gctttgttta cccagaaaac   1560
actccagtta caaaagaagc gtactattat aggacaatat tcgagaaatt ctttcccaag   1620
```

| | |
|---|---|
| aatgctgcta ggttgacagt acctggaggt cctagcgtcg cgtgcagcac tgctaaagct | 1680 |
| gttgaatggg acgcagcctg gtccaaaaac cttgatccat ctggtcgtgc tgctcttggt | 1740 |
| gttcatgatg ctgcatatga agatactcta caaaaatctc ctgcctctgc caatcctgtc | 1800 |
| ttggataacg gctttggtcc agcccttggg gaaagcatgg tcaaaaccgt tgcttcagcc | 1860 |
| actgccgtt | 1869 |

<210> SEQ ID NO 13
<211> LENGTH: 1764
<212> TYPE: DNA
<213> ORGANISM: Galdieria sulphuraria

<400> SEQUENCE: 13

| | |
|---|---|
| atgatttgtg acaaatgcag cctcgtgcgg agcttttttg taggtagacc gcggaccggt | 60 |
| cgcgcctcag cagtcgctgt cgttaccatg tgtgggattc ttgcggtgtt gggctcgtcg | 120 |
| ttaccggtcg aagagcttag agagttggtt aaaagctgca ccaaaaaact atatcacaga | 180 |
| ggtccagatg aagaacaata tttcattagt gaagatgggt ggtgtggttt aggctttgcc | 240 |
| aggttgaaga ttgttgatcc tgagcacggt gtccagccta tgttcaacga ccaacggaca | 300 |
| gtttggagtg tcactaatgg cgagcttac aaccatgaag agatccgaaa aacggaattg | 360 |
| aacaatatga cactccattc tcattctgac tgcgaaataa tgataccttt gtatgagaaa | 420 |
| tatgtttcta gtcagcgtta tgatcatgac attcaatatg tttataatct tctccgtgga | 480 |
| gtctttgctt cttgcctggt tgatttgaaa cgtggttttt tcatggctgg aagagatcct | 540 |
| atcggggtcc gagctctttt ttatgggaca agtaaagatg gtgctgtttg gtttgcttca | 600 |
| gaggcaaaag caattgtgga tgtttgtgat tatgtgacag cattcatacc aggtaccttt | 660 |
| gtgaaaggat acagaggccg cgaacaagca tttctcttta cgagatatta cgaaccagtg | 720 |
| tactggcatg atcactggat gccggtttct ccagttgact atcaacttt acatgacacc | 780 |
| tttgtgttgt cttgtaagcg tcgttttaat gtccgacgtgc ctattggagt atttatctct | 840 |
| ggtggtttgg gttcttctct tgtggcctcc gtcgccaaac gcttactgga tcccaactat | 900 |
| gattttcatt cttttgcttg tggtcttgaa ggagcaccag atgttgctgc agcgcaaaga | 960 |
| gttgccgatt tcttaggaac aaagcaccac gtattaacat ttactgtgga ggagggtatc | 1020 |
| caagcactag accaagtaat atatcacttg gaaacgtacg atgttaccac agttagagca | 1080 |
| tcgacgccga tgtatttgtt atcaggtttg tgcaaaaagt atgtcaaagt agtgttatca | 1140 |
| ggtgaaggag cagatgaaat cttcggtgga tatctctatt tccacaatgc accaaatgag | 1200 |
| attgcatttc atcaagaagt tgttcgccga gtgaaacttt tatacacagc cgacgtattg | 1260 |
| cgtggagata gagcaacggc agcacaaagt ttagaacttc gagttccgtt tcttgataga | 1320 |
| gactttctgg atgttgcaat gagtattcat ccgcgtgaaa aggttacttc taagcataga | 1380 |
| atcgagaaat atatcattcg ctatgccttt tccaaggagt tttgtggtga agagtatctt | 1440 |
| cctgacgata ttctttggag acaaaaagaa cagttttcgg atggcgtggg ctatagctgg | 1500 |
| atcgatggtt taaaggcgta ttgtgaaaag gccgtttccg atgcagactt gcaaaatgcc | 1560 |
| gctcagcgtt ttccgcacga tactccaaca accaaagagg catatgttta ccgagctata | 1620 |
| ttcgaaaaac attttgggaa ttgcaaggca gtacaaggtc ttcgtgaatc agttgcaaga | 1680 |
| tgggtaccta tgtggagtga cagcacggat cctagcggtc gtgcacaaaa agttcatgtg | 1740 |
| gctgcatatt caaatggagg agac | 1764 |

<210> SEQ ID NO 14
<211> LENGTH: 1905
<212> TYPE: DNA
<213> ORGANISM: Galdieria sulphuraria

<400> SEQUENCE: 14

| | | | | | |
|---|---|---|---|---|---|
| atgtgttgct | ctccttacct | cctgatggta | tctagtatct | accaactgac | actatattgc | 60 |
| ttctctttac | atacgtatct | tgctcgatgc | cttctcccta | gtgttgacca | gtgttactca | 120 |
| catagtcttt | gctcatttca | ttgtaatgca | gataccaagc | ggggtaccag | atctgagctc | 180 |
| ccgcgggata | tcacaagttt | gtacaaaaaa | gcaggctcct | gcaggaccat | gtgtgggatt | 240 |
| cttgcggtgt | tgggctcgtc | gttaccggtc | gaagagctta | gagagttggt | taaaagctgc | 300 |
| accaaaaaac | tatatcacag | aggtccagat | gaagaacaat | atttcattag | tgaagatggg | 360 |
| tggtgtggtt | taggctttgc | caggttgaag | attgttgatc | ctgagcacgg | tgtccagcct | 420 |
| atgttcaacg | accaacggac | agtttggagt | gtcactaatg | gcgagcttta | caaccatgaa | 480 |
| gagatccgaa | aaacggaatt | gaacaatatg | acactccatt | ctcattctga | ctgcgaaata | 540 |
| atgataccct | tgtatgagaa | atatgtttct | agtcagcgtt | atgatcatga | cattcaatat | 600 |
| gtttataatc | ttctccgtgg | agtctttgct | tcttgcctgg | ttgatttgaa | acgtggtttt | 660 |
| ttcatggctg | gaagagatcc | tatcggggtc | cgagctcttt | tttatgggac | aagtaaagat | 720 |
| ggtgctgttt | ggtttgcttc | agaggcaaaa | gcaattgtgg | atgtttgtga | ttatgtgaca | 780 |
| gcattcatac | caggtacctt | tgtgaaagga | tacagaggcc | gcgaacaagc | attttctttt | 840 |
| acgagatatt | acgaaccagt | gtactggcat | gatcactgga | tgccggtttc | tccagttgac | 900 |
| tatcaacttt | tacatgacac | ctttgtgttg | tcttgtaagc | gtcgtttaat | gtccgacgtg | 960 |
| cctattggag | tatttatctc | tggtggtttg | ggttcttctc | ttgtggcctc | cgtcgccaaa | 1020 |
| cgcttactgg | atcccaacta | tgattttcat | tcttttgctt | gtggtcttga | aggagcacca | 1080 |
| gatgttgctg | cagcgcaaag | agttgccgat | tccttaggaa | caaagcacca | cgtattaaca | 1140 |
| tttactgtgg | aggagggtat | ccaagcacta | gaccaagtaa | tatatcactt | ggaaacgtac | 1200 |
| gatgttacca | cagttagagc | atcgacgccg | atgtatttgt | tatcaggttt | gtgcaaaaag | 1260 |
| tatgtcaaag | tagtgttatc | aggtgaagga | gcagatgaaa | tcttcggtgg | atatctctat | 1320 |
| ttccacaatg | caccaaatga | gattgcattt | catcaagaag | ttgttcgccg | agtgaaactt | 1380 |
| ttatacacag | ccgacgtatt | gcgtggagat | agagcaacgg | cagcacaaag | tttagaactt | 1440 |
| cgagttccgt | ttcttgatag | agactttctg | gatgttgcaa | tgagtattca | tccgcgtgaa | 1500 |
| aaggttactt | ctaagcatag | aatcgagaaa | tatatcattc | gctatgcctt | ttccaaggag | 1560 |
| ttttgtggtg | aagagtatct | tcctgacgat | attctttgga | gacaaaaaga | acagttttcg | 1620 |
| gatggcgtgg | gctatagctg | gatcgatggt | ttaaaggcgt | attgtgaaaa | ggccgtttcc | 1680 |
| gatgcagact | tgcaaaatgc | cgctcagcgt | tttccgcacg | atactccaac | aaccaaagag | 1740 |
| gcatatgttt | accgagctat | attcgaaaaa | cattttggga | attgcaaggc | agtacaaggt | 1800 |
| cttcgtgaat | cagttgcaag | atgggtacct | atgtggagtg | acagcacgga | tcctagcggt | 1860 |
| cgtgcacaaa | aagttcatgt | ggctgcatat | tcaaatggag | gagac | 1905 |

<210> SEQ ID NO 15
<211> LENGTH: 1851
<212> TYPE: DNA
<213> ORGANISM: Galdieria sulphuraria

<400> SEQUENCE: 15

```
atggtatcta gtatctacca actgacacta tattgcttct ctttacatac gtatcttgct    60
cgatgccttc tccctagtgt tgaccagtgt tactcacata gtctttgctc atttcattgt   120
aatgcagata ccaagcggga gctcgacgtc cctcagcagt cgctgtgcga taccatgtgt   180
gggattcttg cggtgttggg ctcgtcgtta ccggtcgaag agcttagaga gttggttaaa   240
agctgcacca aaaaactata tcacagaggt ccagatgaag aacaatattt cattagtgaa   300
gatgggtggt gtggtttagg ctttgccagg ttgaagattg ttgatcctga gcacggtgtc   360
cagcctatgt tcaacgacca acggacagtt tggagtgtca ctaatggcga gctttacaac   420
catgaagaga tccgaaaaac ggaattgaac aatatgacac tccattctca ttctgactgc   480
gaaataatga tacctttgta tgagaaatat gtttctagtc agcgttatga tcatgacatt   540
caatatgttt ataatcttct ccgtggagtc tttgcttctt gcctggttga tttgaaacgt   600
ggttttttca tggctggaag agatcctatc ggggtccgag ctcttttttta tgggacaagt   660 aaagatggtg ctgtttggtt tgcttcagag gcaaaagcaa ttgtggatgt ttgtgattat   720
gtgacagcat tcataccagg tacctttgtg aaaggataca gaggccgcga caagcatttt   780
tcttttacga gatattacga accagtgtac tggcatgatc actggatgcc ggtttctcca   840
gttgactatc aacttttaca tgacaccttt gtgttgtctt gtaagcgtcg tttaatgtcc   900
gacgtgccta ttggagtatt tatctctggt ggtttgggtt cttctcttgt ggcctccgtc   960
gccaaacgct tactggatcc caactatgat tttcattctt ttgcttgtgg tcttgaagga  1020
gcaccagatg ttgctgcagc gcaaagagtt gccgattttct taggaacaaa gcaccacgta  1080
ttaacattta ctgtggagga gggtatccaa gcactagacc aagtaatata tcacttggaa  1140
acgtacgatg ttaccacagt tagagcatcg acgccgatgt atttgttatc aggtttgtgc  1200
aaaaagtatg tcaaagtagt gttatcaggt gaaggagcag atgaaatctt cggtggatat  1260
ctctatttcc acaatgcacc aaatgagatt gcatttcatc aagaagttgt tcgccgagtg  1320 aaactttttat acacagccga cgtattgcgt ggagatagac aacggcagc acaaagttta  1380 gaacttcgag ttccgtttct tgatagagac tttctggatg ttgcaatgag tattcatccg  1440
cgtgaaaagg ttacttctaa gcatagaatc gagaaatata tcattcgcta tgccttttcc  1500
aaggagtttt gtggtgaaga gtatcttcct gacgatattc tttggagaca aaaagaacag  1560
ttttcggatg gcgtgggcta tagctggatc gatggtttaa aggcgtattg tgaaaaggcc  1620
gtttccgatg cagacttgca aaatgccgct cagcgttttc cgcacgatac tccaacaacc  1680
aaagaggcat atgtttaccg agctatattc gaaaaacatt ttgggaattg caaggcagta  1740
caaggtcttc gtgaatcagt tgcaagatgg gtacctatgt ggagtgacag cacggatcct  1800
agcggtcgtg cacaaaaagt tcatgtggct gcatattcaa atggaggaga c            1851
```

<210> SEQ ID NO 16
<211> LENGTH: 1851
<212> TYPE: DNA
<213> ORGANISM: Galdieria sulphuraria

<400> SEQUENCE: 16

```
atggtatcta gtatctacca actgacacta tattgcttct ctttacatac gtatcttgct    60
cgatgccttc tccctagtgt tgaccagtgt tactcacata gtctttgctc atttcattgt   120
aatgcagata ccaagcggga gctcgacgtc cctcagcagt cgctgtgcga taccatgtgt   180
gggattcttg cggtgttggg ctcgtcgtta ccggtcgaag agcttagaga gttggttaaa   240
agctgcacca aaaaactata tcacagaggt ccagatgaag aacaatattt cattagtgaa   300
```

```
gatgggtggt gtggtttagg ctttgccagg ttgaagattg ttgatcctga gcacggtgtc      360
cagcctatgt tcaacgacca acggacagtt tggagtgtca ctaatggcga gctttacaac      420
catgaagaga tccgaaaaac ggaattgaac aatatgacac tccattctca ttctgactgc      480
gaaataatga tacctttgta tgagaaatat gtttctagtc agcgttatga tcatgacatt      540
caatatgttt ataatcttct ccgtggagtc tttgcttctt gcctggttga tttgaaacgt      600
ggttttttca tggctggaag agatcctatc ggggtccgag ctctttttta tgggacaagt      660
aaagatggtg ctgtttggtt tgcttcagag gcaaaagcaa ttgtggatgt ttgtgattat      720
gtgacagcat tcataccagg tacctttgtg aaaggataca gaggccgcga caagcatt      780 tcttttacga gatattacga accagtgtac tggcatgatc actggatgcc ggtttctcca      840
gttgactatc aacttttaca tgacaccttt gtgttgtctt gtaagcgtcg tttaatgtcc      900
gacgtgccta ttggagtatt tatctctggt ggtttgggtt cttctcttgt ggcctccgtc      960
gccaaacgct tactggatcc caactatgat tttcattctt ttgcttgtgg tcttgaagga    1020
gcaccagatg ttgctgcagc gcaaagagtt gccgatttct taggaacaaa gcaccacgta    1080
ttaacattta ctgtggagga gggtatccaa gcactagacc aagtaatata tcacttggaa    1140
acgtacgatg ttaccacagt tagagcatcg acgccgatgt atttgttatc aggtttgtgc    1200
aaaaagtatg tcaaagtagt gttatcaggt gaaggagcag atgaaatctt cggtggatat    1260
ctctatttcc acaatgcacc aaatgagatt gcatttcatc aagaagttgt tcgccgagtg    1320
aaacttttat acacagccga cgtattgcgt ggagatagag caacggcagc acaaagttta    1380
gaacttcgag ttccgtttct tgatagagac tttctggatg ttgcaatgag tattcatccg    1440
cgtgaaaagg ttacttctaa gcatagaatc gagaaatata tcattcgcta tgccttttcc    1500
aaggagtttt gtggtgaaga gtatcttcct gacgatattc tttggagaca aaaagaacag    1560
ttttcggatg gcgtgggcta tagctggatc gatggtttaa aggcgtattg tgaaaaggcc    1620
gtttccgatg cagacttgca aaatgccgct cagcgttttc cgcacgatac tccaacaacc    1680
aaagaggcat atgtttaccg agctatattc gaaaaacatt ttgggaattg caaggcagta    1740
caaggtcttc gtgaatcagt tgcaagatgg gtacctatgt ggagtgacag cacgatcct    1800 agcggtcgtg cacaaaaagt tcatgtggct gcatattcaa atggaggaga c            1851
```

<210> SEQ ID NO 17  
<211> LENGTH: 1803  
<212> TYPE: DNA  
<213> ORGANISM: Saccharomyces cerevisiae

<400> SEQUENCE: 17

```
atgatttgtg acaaatgcag cctcgtgcgg agcttttttg taggtagacc gcggaccggt       60
cgcgcctcag cagtcgctgt cgttaccatg tgtggtatct ttgcagcctt caagcatgaa      120
gatattcaca acttcaaacc aaaagctcta caactatcta aaaaaatcag acaccgtggc      180
ccagattggt caggaaatgc cgttatgaat tccaccattt tcgttcacga gaggttggct      240
attgttggtt tagactccgg tgcccagcca atcacttcag ctgatggcga atatatgctt      300
ggcgttaatg gtgagatcta caaccacatc caactaaggg agatgtgctc tgattacaag      360
tttcaaactt tcagtgactg tgaacccatc ataccgttat atttggaaca tgatatcgat      420
gctccaaaat atctggacgg tatgttcgca ttttgtctgt atgattccaa gaaagaccgt      480
attgtcgctg caagagaccc tatcggtgtt gtcactttat acatggggcg ttcttctcag      540
```

```
tctccagaga ccgtttattt tgcctccgaa ttaaaatgtc taactgacgt tgtgacagt     600 atcatttcgt tccctcctgg tcatgtctac gattctgaaa cggacaagat tactcgttac    660
tttaccccag actggttgga tgaaaagcgt atcccatcca ccccagttga ctaccatgct    720
atcagacaca gtttagaaaa ggccgttaga aagaggctaa tggctgaagt tccatacggt    780
gttcttctat ccggtgggct ggactcttct ttgattgctg cgattgctgc tcgtgaaacg    840
gaaaaagcta atgctgatgc taacgaagac aacaatgttg acgagaagca acttgcaggt    900
atcgatgacc aaggccatct acacacatcc ggttggtctc gtttgcattc gtttgcgatt    960
ggtctaccaa atgcacctga tttacaagcg gctagaaaag tcgccaaatt cattggttct   1020
atccaccatg aacacacttt tacattacaa gaaggtttgg atgctttgga cgacgtgatc   1080
taccatttgg aaacttacga cgttaccact atcagagctt ctacaccaat gttcttacta   1140
tctagaaaga ttaaggccca aggtgtcaaa atggttcttt ctggtgaagg ctcggacgaa   1200
atattcggtg gctatctata tttcgcacaa gcaccttctg ctgcagaatt tcacaccgaa   1260
tctgtgcaac gtgtcaagaa cttgcatttg gcagattgtt tgagagctaa taagtccacg   1320
atggcttggg gtctagaagc tcgtgttccc ttcttagaca agactttttt gcagctatgt   1380
atgaacattg atccaaatga aaagatgatc aagccaaagg aaggacgtat cgaaaaatac   1440
attttaagaa aggcattcga cactacagat gaaccagatg ttaagccata cctacctgaa   1500
gaaatcttat ggagacaaaa ggaacaattt tccgatggtg ttggctactc atggattgac   1560
ggcctaagag acactgctga aagggccatt tctgacgcca tgtttgccaa tccaaaggct   1620
gattggggcg acgatattcc aaccaccaaa gaagcttact ggtacaggct gaagtttgat   1680
gcttggtttc ctcaaaagac tgcggcagac actgtcatga gatggattcc aaaggccgat   1740 tgggggttgtg ccgaagatcc ttcaggtaga tacgccaaaa tacacgaaaa gcacgtcagt   1800
gct                                                                 1803
```

```
<210> SEQ ID NO 18
<211> LENGTH: 21
<212> TYPE: DNA
<213> ORGANISM: Artificial Sequence
<220> FEATURE:
<223> OTHER INFORMATION: synthetic primer sequence

<400> SEQUENCE: 18
gcagucgctg ucgtuaccat g                                               21

<210> SEQ ID NO 19
<211> LENGTH: 20
<212> TYPE: DNA
<213> ORGANISM: Artificial Sequence
<220> FEATURE:
<223> OTHER INFORMATION: synthetic primer sequence

<400> SEQUENCE: 19
gcgaguaccg cugggtucta                                                 20

<210> SEQ ID NO 20
<211> LENGTH: 39
<212> TYPE: DNA
<213> ORGANISM: Artificial Sequence
<220> FEATURE:
<223> OTHER INFORMATION: synthetic primer sequence

<400> SEQUENCE: 20
gctcctgcag gaccatgtgt tccatttttg gaatcttca                            39
```

<210> SEQ ID NO 21
<211> LENGTH: 37
<212> TYPE: DNA
<213> ORGANISM: Artificial Sequence
<220> FEATURE:
<223> OTHER INFORMATION: synthetic primer sequence

<400> SEQUENCE: 21
ctgggtctcg agctacagca gtgcttgttg atgaacc                               37

<210> SEQ ID NO 22
<211> LENGTH: 53
<212> TYPE: DNA
<213> ORGANISM: Artificial Sequence
<220> FEATURE:
<223> OTHER INFORMATION: synthetic primer sequence

<400> SEQUENCE: 22 cccctttat aatgccaact ttgtacaaaa aagcaggctc ctgcaggacc atg            53

<210> SEQ ID NO 23
<211> LENGTH: 48
<212> TYPE: DNA
<213> ORGANISM: Artificial Sequence
<220> FEATURE:
<223> OTHER INFORMATION: synthetic primer sequence

<400> SEQUENCE: 23
ggggtcttat aatgccaact ttgtacaaga aagctgggtc tcgagcta                 48

<210> SEQ ID NO 24
<211> LENGTH: 36
<212> TYPE: DNA
<213> ORGANISM: Artificial Sequence
<220> FEATURE:
<223> OTHER INFORMATION: synthetic primer sequence

<400> SEQUENCE: 24
gctcctgcag gaccatgtgt ggaattacag gctggg                              36

<210> SEQ ID NO 25
<211> LENGTH: 47
<212> TYPE: DNA
<213> ORGANISM: Artificial Sequence
<220> FEATURE:
<223> OTHER INFORMATION: synthetic primer sequence

<400> SEQUENCE: 25
ctgggtctcg agctaaccaa ttaatttgat attgtaatgc ttaagcc                  47

<210> SEQ ID NO 26
<211> LENGTH: 53
<212> TYPE: DNA
<213> ORGANISM: Artificial Sequence
<220> FEATURE:
<223> OTHER INFORMATION: synthetic primer sequence

<400> SEQUENCE: 26 cccctttat aatgccaact ttgtacaaaa aagcaggctc ctgcaggacc atg            53

<210> SEQ ID NO 27
<211> LENGTH: 48
<212> TYPE: DNA
<213> ORGANISM: Artificial Sequence
<220> FEATURE:

<223> OTHER INFORMATION: synthetic primer sequence

<400> SEQUENCE: 27
ggggtcttat aatgccaact ttgtacaaga aagctgggtc tcgagcta        48

<210> SEQ ID NO 28
<211> LENGTH: 31
<212> TYPE: DNA
<213> ORGANISM: Artificial Sequence
<220> FEATURE:
<223> OTHER INFORMATION: synthetic primer sequence

<400> SEQUENCE: 28
gctcctgcag gaccatgtgc ggcatcctcg c        31

<210> SEQ ID NO 29
<211> LENGTH: 36
<212> TYPE: DNA
<213> ORGANISM: Artificial Sequence
<220> FEATURE:
<223> OTHER INFORMATION: synthetic primer sequence

<400> SEQUENCE: 29
ctgggtctcg agctagacag ctgtggctga agcaac        36

<210> SEQ ID NO 30
<211> LENGTH: 53
<212> TYPE: DNA
<213> ORGANISM: Artificial Sequence
<220> FEATURE:
<223> OTHER INFORMATION: synthetic primer sequence

<400> SEQUENCE: 30 cccctttat aatgccaact ttgtacaaaa aagcaggctc tgcaggacc atg        53

<210> SEQ ID NO 31
<211> LENGTH: 48
<212> TYPE: DNA
<213> ORGANISM: Artificial Sequence
<220> FEATURE:
<223> OTHER INFORMATION: synthetic primer sequence

<400> SEQUENCE: 31
ggggtcttat aatgccaact ttgtacaaga aagctgggtc tcgagcta        48

<210> SEQ ID NO 32
<211> LENGTH: 35
<212> TYPE: DNA
<213> ORGANISM: Artificial Sequence
<220> FEATURE:
<223> OTHER INFORMATION: synthetic primer sequence

<400> SEQUENCE: 32
gctcctgcag gaccatgtgc ggcatacttg ctgtg        35

<210> SEQ ID NO 33
<211> LENGTH: 32
<212> TYPE: DNA
<213> ORGANISM: Artificial Sequence
<220> FEATURE:
<223> OTHER INFORMATION: synthetic primer sequence

<400> SEQUENCE: 33
ctgggtctcg agctatccct cgatggcaac gc        32

```
<210> SEQ ID NO 34
<211> LENGTH: 53
<212> TYPE: DNA
<213> ORGANISM: Artificial Sequence
<220> FEATURE:
<223> OTHER INFORMATION: synthetic primer sequence

<400> SEQUENCE: 34 cccctttat aatgccaact ttgtacaaaa aagcaggctc ctgcaggacc atg            53

<210> SEQ ID NO 35
<211> LENGTH: 48
<212> TYPE: DNA
<213> ORGANISM: Artificial Sequence
<220> FEATURE:
<223> OTHER INFORMATION: synthetic primer sequence

<400> SEQUENCE: 35
ggggtcttat aatgccaact ttgtacaaga aagctgggtc tcgagcta                48

<210> SEQ ID NO 36
<211> LENGTH: 34
<212> TYPE: DNA
<213> ORGANISM: Artificial Sequence
<220> FEATURE:
<223> OTHER INFORMATION: synthetic primer sequence

<400> SEQUENCE: 36
gctcctgcag gaccatgtgt ggcatcctcg ccgt                               34

<210> SEQ ID NO 37
<211> LENGTH: 34
<212> TYPE: DNA
<213> ORGANISM: Artificial Sequence
<220> FEATURE:
<223> OTHER INFORMATION: synthetic primer sequence

<400> SEQUENCE: 37
ctgggtctcg agctaaacgg cagtggctga agca                               34

<210> SEQ ID NO 38
<211> LENGTH: 53
<212> TYPE: DNA
<213> ORGANISM: Artificial Sequence
<220> FEATURE:
<223> OTHER INFORMATION: synthetic primer sequence

<400> SEQUENCE: 38 cccctttat aatgccaact ttgtacaaaa aagcaggctc ctgcaggacc atg            53

<210> SEQ ID NO 39
<211> LENGTH: 48
<212> TYPE: DNA
<213> ORGANISM: Artificial Sequence
<220> FEATURE:
<223> OTHER INFORMATION: synthetic primer sequence

<400> SEQUENCE: 39
ggggtcttat aatgccaact ttgtacaaga aagctgggtc tcgagcta                48

<210> SEQ ID NO 40
<211> LENGTH: 40
<212> TYPE: DNA
<213> ORGANISM: Artificial Sequence
<220> FEATURE:
<223> OTHER INFORMATION: synthetic primer sequence
```

```
<400> SEQUENCE: 40
gctcctgcag gaccatgtgt ggtattcttg ctgttcttgg                               40

<210> SEQ ID NO 41
<211> LENGTH: 33
<212> TYPE: DNA
<213> ORGANISM: Artificial Sequence
<220> FEATURE:
<223> OTHER INFORMATION: synthetic primer sequence

<400> SEQUENCE: 41
ctgggtctcg agctagccct ggatggcaac acc                                      33

<210> SEQ ID NO 42
<211> LENGTH: 33
<212> TYPE: DNA
<213> ORGANISM: Artificial Sequence
<220> FEATURE:
<223> OTHER INFORMATION: synthetic primer sequence

<400> SEQUENCE: 42
ctgggtctcg agctagccct ggatggcaac acc                                      33

<210> SEQ ID NO 43
<211> LENGTH: 48
<212> TYPE: DNA
<213> ORGANISM: Artificial Sequence
<220> FEATURE:
<223> OTHER INFORMATION: synthetic primer sequence

<400> SEQUENCE: 43
ggggtcttat aatgccaact ttgtacaaga aagctgggtc tcgagcta                      48

<210> SEQ ID NO 44
<211> LENGTH: 26
<212> TYPE: DNA
<213> ORGANISM: Artificial Sequence
<220> FEATURE:
<223> OTHER INFORMATION: synthetic primer sequence

<400> SEQUENCE: 44
cctctagatg tgcggcatac ttgctg                                              26

<210> SEQ ID NO 45
<211> LENGTH: 25
<212> TYPE: DNA
<213> ORGANISM: Artificial Sequence
<220> FEATURE:
<223> OTHER INFORMATION: synthetic primer sequence

<400> SEQUENCE: 45
cgaattctat ccctcgatgg caacg                                               25

<210> SEQ ID NO 46
<211> LENGTH: 27
<212> TYPE: DNA
<213> ORGANISM: Artificial
<220> FEATURE:
<223> OTHER INFORMATION: Synthetic primer

<400> SEQUENCE: 46
tcctagacat gtccggcata cttgctg                                             27

<210> SEQ ID NO 47
<211> LENGTH: 23
```

```
<212> TYPE: DNA
<213> ORGANISM: Artificial
<220> FEATURE:
<223> OTHER INFORMATION: Synthetic primer

<400> SEQUENCE: 47
tgcagaattc tatccctcga tgg                                            23

<210> SEQ ID NO 48
<211> LENGTH: 37
<212> TYPE: DNA
<213> ORGANISM: Artificial
<220> FEATURE:
<223> OTHER INFORMATION: Synthetic primer

<400> SEQUENCE: 48
gcagtcgctg tcgttacccg gcatcatgtg tggcatc                             37

<210> SEQ ID NO 49
<211> LENGTH: 41
<212> TYPE: DNA
<213> ORGANISM: Artificial
<220> FEATURE:
<223> OTHER INFORMATION: Synthetic primer

<400> SEQUENCE: 49
gcgagtaccg ctgggttcta acgtactctc gtcagaccgc g                        41
```

CORN PLANTS AND SEED ENHANCED FOR ASPARAGINE AND PROTEIN

This application is a continuation of U.S. Ser. No. 12/694,152, filed Jan. 26, 2010, now abandoned, which application is a divisional of U.S. Ser. No. 11/434,566, filed May 15, 2006, now abandoned, which application claims the priority of U.S. Provisional Appl. Ser. No. 60/681,348, filed May 16, 2005, the entire disclosures of which are incorporated herein by reference in their entireties. This application is also a continuation-in-part of U.S. Ser. No. 11/978,677, now abandoned, filed Oct. 30, 2007, which application is a continuation-in-part under 35 U.S.C. §120 of U.S. application Ser. No. 10/425,114, filed on Apr. 28, 2003 (abandoned), which is hereby incorporated by reference in its entirety, including a copy of its Sequence Listing and Table 1. U.S. application Ser. No. 10/425,114, now abandoned, claims priority under 35 U.S.C. §120 as a continuation-in-part of U.S. application Ser. No. 09/826,019, filed Apr. 5, 2001 (abandoned), which is a continuation-in-part of U.S. application Ser. No. 09/773,370, filed Feb. 1, 2001 (abandoned), which claims the benefit under 35 U.S.C. §119 to U.S. Provisional Application Ser. No. 60/179,730, filed Feb. 2, 2000. U.S. application Ser. No. 10/425,114 also claims priority under 35 U.S.C. §120 as a continuation-in-part of U.S. application Ser. No. 10/219,999, filed Aug. 15, 2002 (abandoned), which claims the benefit under 35 U.S.C. §119 to U.S. Provisional Application Ser. No. 60/324,109, filed Sep. 21, 2001, and to U.S. Provisional Application Ser. No. 60/312,544, filed Aug. 15, 2001. U.S. application Ser. No. 10/425,114 also claims priority under 35 U.S.C. §120 as a continuation-in-part of U.S. application Ser. No. 09/666,355, filed Sep. 20, 2000. U.S. application Ser. No. 10/425,114 also claims priority under 35 U.S.C. §120 as a continuation-in-part of U.S. application Ser. No. 09/985,678, filed Nov. 5, 2001 (abandoned), which is a continuation of U.S. application Ser. No. 09/304,517, filed May 6, 1999 (abandoned). U.S. application Ser. No. 10/425,114 also claims priority under 35 U.S.C. §120 as a continuation-in-part of U.S. application Ser. No. 09/849,529, filed May 7, 2001 (abandoned), which claims the benefit under 35 U.S.C. §119 to U.S. Provisional Application Ser. No. 60/196,868, filed May 9, 2000. U.S. application Ser. No. 10/425,114 also claims priority under 35 U.S.C. §120 as a continuation-in-part of U.S. application Ser. No. 09/804,730, filed Mar. 13, 2001 (abandoned), which claims the benefit under 35 U.S.C. §119 to U.S. Provisional Application Ser. No. 60/189,657, filed Mar. 15, 2000. U.S. application Ser. No. 10/425,114 also claims priority under 35 U.S.C. §120 as a continuation-in-part of U.S. application Ser. No. 09/850,147, filed May 8, 2001 (abandoned), which claims the benefit under 35 U.S.C. §119 to U.S. Provisional Application Ser. No. 60/202,213, filed May 8, 2000. All of the foregoing applications are hereby incorporated by reference in their entirety, including their respective sequence listing and tables.

BACKGROUND OF THE INVENTION

1. Field of the Invention

The present invention relates generally to the field of plant biotechnology and more specifically to enhancing asparagine and protein in corn plants and seed.

2. Description of Related Art

Farmers and consumers desire crop plants with improved agronomic traits such as increased yield, increased seed protein production, and improved nutritional composition. Desirable nutritional components of crop plants include, among others, fiber, antioxidants such as Vitamin E, selenium, iron, magnesium, zinc, B vitamins, lignans, phenolic acids, essential amino acids, and phytoestrogens. Although considerable efforts in plant breeding have provided some gains in these desired traits, the ability to introduce specific non-host DNA into a plant genome provides further opportunities for generation of plants with these traits. In particular, while the yield of conventional corn has steadily increased over the years, there has not been a similar increase in the capacity of corn plants to assimilate nitrogen more efficiently or to increase seed protein content.

Availability of nitrogen has a significant positive impact on plant productivity, biomass, and crop yield including the production of seed protein. In plants, inorganic nitrogen is assimilated from the soil, reduced to ammonia, and incorporated into organic nitrogen in the form of the nitrogen-transporting amino acids asparagine, glutamine, aspartic acid and glutamic acid. Asparagine (Asn) is the preferred amide transport molecule because of its high nitrogen to carbon ratio (2N:4C versus 2N:5C) and because it is relatively inert. Asn and other amino acids are also used as building blocks for protein synthesis.

In plants, Asn is synthesized from glutamine, aspartate and ATP, in a reaction catalyzed by the enzyme asparagine synthetase (AsnS). Glutamate, AMP and pyrophosphate are formed as by-products. Two forms of AsnS have been described: a glutamine-dependent form and an ammonia-dependent form. The glutamine-dependent AsnS can catalyze both the glutamine-dependent and ammonia-dependent reactions although glutamine is the preferred nitrogen source.

High concentration of protein is considered an important quality trait for most major crops, including soybean, corn, and wheat. Varieties of high protein corn, wheat, and soybeans, for example, have been identified through traditional breeding. However, most of the high protein lines developed this way have yield drag or other agronomic disadvantages. It would be desirable if the protein content of crops, especially corn, could be increased above the presently available levels, both for human consumption and for use of the product in animal feeds. This would offer the benefit of greatly enhanced nutrient value when the crop is used as food and feed for humans and animals.

SUMMARY OF THE INVENTION

The present invention provides a method and compositions for treatment of crops and other plant products so as to increase the protein and amino acid content in plants. The method and compositions increase the level of free amino acids and protein in corn tissues, particularly in seeds. More specifically, a transgenic corn plant and seed is provided that contains in its genome a heterologous DNA composition that expresses a gene product involved in increased asparagine and increased protein biosynthesis. The expression of the product enhances the nutritional value of food corn and feed corn sources and processed products derived from the transgenic corn seed or parts thereof.

In one aspect, the invention provides methods for increasing protein content in a corn plant. A DNA construct comprising a polynucleotide sequence selected from the group consisting of SEQ ID NOs 1, 3, 5, 7, 9, 10, 11, 12, 13, 14, 15, 16, and 17 wherein the polynucleotide molecule encodes an asparagine synthetase polypeptide or polypeptide having asparagine synthetase activity is also included.

In one embodiment, the present invention comprises a corn plant cell transformed with the heterologous DNA composition encoding an asparagine synthetase identified as SEQ ID NO: 4. More specifically, the expression of the heterologous corn AsnS2 (asparagine synthetase isozyme 2) polynucleotide molecule in the transgenic corn plant results in an elevated level of asparagine and protein in the transgenic plant, for example, in the seeds of the corn plant compared to a corn plant of the same variety not expressing the heterologous corn AsnS2 polynucleotide molecule.

The present invention also relates to animal feed comprising the aforementioned seed with increased protein or amino acid content, or a processed product of such seed, for example, a meal. Accordingly, the present invention also encompasses a corn seed containing an asparagine synthetase enzyme produced by expression of a heterologous DNA construct comprising a DNA molecule encoding a corn asparagine synthetase enzyme. One embodiment of such a seed is harvested grain, the present invention also encompasses meal, gluten and other corn products made from such grain.

The present invention includes isolated nucleic acid primer sequences comprising one or more of SEQ ID NOs 18-45, or the complement thereof. The present invention includes a method to detect or identify, in the genome of a transformed plant or progeny thereof, a heterologous polynucleotide molecule encoding a plant AsnS polypeptide, or a plant polypeptide having AsnS activity of the present invention, comprising a polynucleotide molecule selected from the group consisting of SEQ ID NOs 18-45, wherein said polynucleotide molecule is used as a DNA primer in a DNA amplification method.

BRIEF DESCRIPTION OF THE FIGURES

FIG. 7. Transgene expression in pMON92870 events. Error bars represent 95% confidence interval, with n>3 plants for transgenic events and n=8 plants for inbred control.

DESCRIPTION OF THE NUCLEIC ACID AND POLYPEPTIDE SEQUENCES

Figure 1:
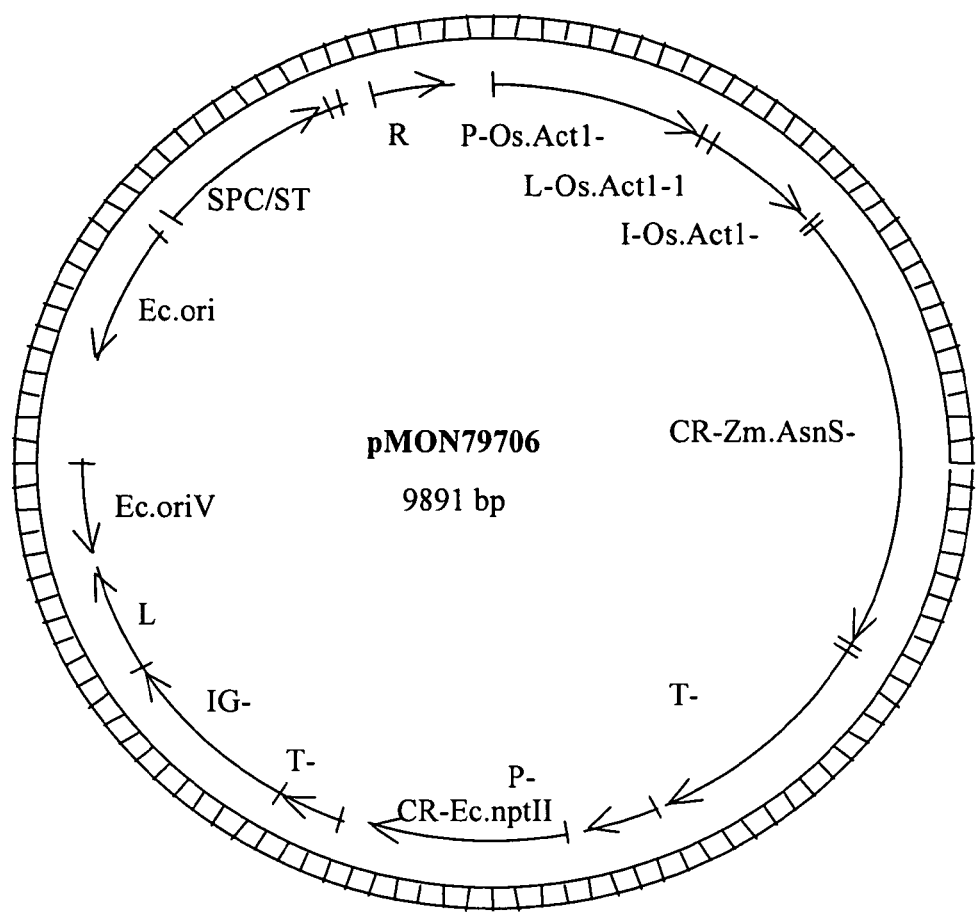
FIG. 1 illustrates the plasmid map of pMON79706.

SEQ ID NO: 1 is a polynucleotide sequence encoding a *Zea mays* AsnS1.
SEQ ID NO: 2 is a *Zea mays* AsnS1 polypeptide.
SEQ ID NO: 3 is a polynucleotide sequence encoding a *Zea mays* AsnS2.
SEQ ID NO: 4 is a *Zea mays* AsnS2 polypeptide.
SEQ ID NO: 5 is a polynucleotide sequence encoding a *Zea mays* AsnS3.
SEQ ID NO: 6 is a *Zea mays* AsnS3 polypeptide.
SEQ ID NO: 7 is a polynucleotide sequence encoding a *Glycine max* AsnS.
SEQ ID NO: 8 is a *Glycine max* AsnS polypeptide.
SEQ ID NO: 9 is a polynucleotide sequence encoding a *Xylella fastidiosa* AsnS.
SEQ ID NO: 10 is a polynucleotide sequence encoding a *Xanthomonas campestris* AsnS.
SEQ ID NO: 11 is a polynucleotide sequence encoding a *Bacillus halodurans* AsnS.
SEQ ID NO: 12 is a polynucleotide sequence encoding an *Oryza sativa* AsnS.
SEQ ID NO: 13 is a polynucleotide sequence encoding a *Galdieria sulphuraria* AsnS.
SEQ ID NO: 14 is a polynucleotide sequence encoding a *Galdieria sulphuraria* AsnS.
SEQ ID NO: 15 is a polynucleotide sequence encoding a *Galdieria sulphuraria* AsnS.
SEQ ID NO: 16 is a polynucleotide sequence encoding a *Galdieria sulphuraria* AsnS.
SEQ ID NO: 17 is a polynucleotide sequence encoding a *Saccharomyces cerevisiae* CGPG3913 AsnS.
SEQ ID NO: 18 is a forward (f) AsnS PCR primer sequence.
SEQ ID NO: 19 is a forward (f) AsnS PCR primer sequence.
SEQ ID NOs 20-43, are primary and secondary forward (f) and reverse (r) AsnS PCR primer sequences used in a Gateway cloning procedure.
SEQ ID NO: 44, a forward (f) AsnS PCR primer sequence.
SEQ ID NO: 45, a forward (f) AsnS PCR primer sequence.
SEQ ID NO:46 ZmASsense primer
SEQ ID NO:47 ZmASantisense primer
SEQ ID NO: 48 corn AsnS3 forward primer
SEQ ID NO: 49 corn AsnS3 reverse primer

DETAILED DESCRIPTION OF THE INVENTION

The following is a detailed description of the invention provided to aid those skilled in the art in practicing the present invention. Unless otherwise defined herein, terms are to be understood according to conventional usage by those of ordinary skill in the relevant art. Definitions of common terms in molecular biology may also be found in Rieger et al., 1991; and Lewin, 1994. The nomenclature for DNA bases as set forth at 37 CFR §1.822 is used. The standard one- and three-letter nomenclature for amino acid residues is used. Modifications and variations in the embodiments described herein may be made by those of ordinary skill in the art without departing from the spirit or scope of the present invention.

The present invention provides a method to increase protein content in a corn plant by introducing into the genome of a corn plant cell a heterologous polynucleotide that expresses an AsnS polypeptide in the transgenic plant cell. The present invention provides DNA constructs that comprise (comprise means "including but not limited to") polynucleotide molecules, or segments of a polynucleotide molecule that encode an AsnS polypeptide, optionally operably linked to a chloroplast transit peptide.

Polynucleotide molecules encoding a AsnS polypeptide or analog or allele thereof, or polynucleotide molecules encoding a transit peptide or marker/reporter gene are "isolated" in that they have been at least partially prepared in vitro, e.g., isolated from its native state, from a cell, purified, and amplified, e.g., they are in combination with genetic elements heterologous to those found normally associated with them in their native state. As used herein, a heterologous DNA construct comprising an AsnS encoding polynucleotide molecule that has been introduced into a host cell, is preferably not identical to any polynucleotide molecule present in the cell in its native, untransformed state and is isolated with respect of other DNA molecules that occur in the genome of the host cell.

As used herein, "altered or increased" levels of asparagine in a transformed plant, plant tissue, or plant cell are levels which are greater than the levels found in the corresponding plant, plant tissue, or plant cells not containing the DNA constructs of the present invention.

The agents of the present invention may also be recombinant. As used herein, the term recombinant means any agent (e.g., DNA, peptide, etc.), that is, or results, however indirectly, from human manipulation of a polynucleotide molecule.

As used herein in a preferred aspect, an increase in the nutritional quality of a seed, for example, increased seed protein content, is determined by the ability of a plant to produce a seed having a higher yield of protein or a nutritional component than a seed without such increase in protein or nutritional quality. In a particularly preferred aspect of the present invention, the increase in nutritional quality is measured relative to a plant with a similar genetic background to the nutritionally enhanced plant except that the plant of the present invention expresses or over expresses a protein or fragment thereof described in the heterologous DNA constructs herein.

Polynucleotide Molecules

The present invention includes and provides transgenic corn plants and seed that comprise in their genome a transgene comprising a heterologous DNA molecule encoding a corn asparagine synthetase (Zm.AsnS2) enzyme, the DNA molecule, for example, comprising SEQ ID NO: 3 and sequences having at least 90%, 95%, or 99% identity to such sequences with functional asparagine synthetase activity.

A further aspect of the invention is a method for increasing protein in a corn plant by introducing into a corn cell a DNA construct that provides a heterologous polynucleotide molecule, for example, SEQ ID NOs 1, 3, 5, 7, 9, 10, 11, 12, 13, 14, 15, 16 and 17 that encode an asparagine synthetase enzyme. The polynucleotide can differ from any of these examples without altering the polypeptide for which it encodes. For example, it is understood that codons capable of coding for such conservative amino acid substitutions are known in the art. Additionally, the invention contemplates that polypeptides in which one or more amino acid have been deleted, substituted, or added without altering the asparagine synthetase function can be used in the invention In one aspect of the present invention the polynucleotide of the present invention are said to be introduced polynucleotide molecules. A polynucleotide molecule is said to be "introduced" if it is inserted into a cell or organism as a result of human manipulation, no matter how indirect. Examples of introduced polynucleotide molecules include, without limitation, polynucleotides that have been introduced into cells via transformation, transfection, injection, and projection, and those that have been introduced into an organism via conjugation, endocytosis, phagocytosis, etc. Preferably, the polynucleotide is inserted into the genome of the cell.

One subset of the polynucleotide molecules of the present invention is fragment polynucleotide molecules. Fragment polynucleotide molecules may consist of significant portion(s) of, or indeed most of, the polynucleotide molecules of the present invention, such as those specifically disclosed. Alternatively, the fragments may comprise smaller oligonucleotides (having from about 15 to about 400 nucleotide residues and more preferably, about 15 to about 30 nucleotide residues, or about 50 to about 100 nucleotide residues, or about 100 to about 200 nucleotide residues, or about 200 to about 400 nucleotide residues, or about 275 to about 350 nucleotide residues). A fragment of one or more of the polynucleotide molecules of the present invention may be a probe and specifically a PCR primer molecule. A PCR primer is a polynucleotide molecule capable of initiating a polymerase activity while in a double-stranded structure with another polynucleotide. Various methods for determining the structure of PCR probes and PCR techniques exist in the art.

As used herein, two polynucleotide molecules are said to be capable of specifically hybridizing to one another if the two molecules are capable of forming an anti-parallel, double-stranded polynucleotide structure.

A polynucleotide molecule is said to be the "complement" of another polynucleotide molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., (2001), and by Haymes et al., (1985). Departures from complete complementarity are therefore permissible, as long as such departures do not completely preclude the capacity of the molecules to form a double-stranded structure. Thus, in order for a polynucleotide molecule to serve as a primer or probe it need only be sufficiently complementary in sequence to be able to form a stable double-stranded structure under the particular solvent and salt concentrations employed.

Appropriate stringency conditions which promote DNA hybridization are, for example, 6.0×sodium chloride/sodium citrate (SSC) at about 45° C., followed by a wash of 2.0×SSC at 20-25° C., are known to those skilled in the art or can be found in Ausubel, et al., eds. (1989), section 6.3.1-6.3.6. For example, the salt concentration in the wash step can be selected from a low stringency of about 2.0×SSC at 50° C. to a high stringency of about 0.2×SSC at 65° C. In addition, the temperature in the wash step can be increased from low stringency conditions at room temperature, about 22° C., to high stringency conditions at about 65° C. Both temperature and salt may be varied, or either the temperature or the salt concentration may be held constant such that a nucleic acid will specifically hybridize to one or more of the polynucleotide molecules provided herein, for example, as set forth in: SEQ ID NOs 1, 3, 5, 7, 9, 10, 11, 12, 13, 14, 15, 16, 17 and 18-45 and complements thereof, under moderately stringent conditions, for example at about 2.0×SSC and about 65° C.

In one embodiment of a method of the present invention, any of the polynucleotide sequences or polypeptide sequences, or fragments of either, of the present invention can be used to search for related sequences. As used herein, "search for related sequences" means any method of determining relatedness between two sequences, including, but not limited to, searches that compare sequence homology: for example, a PBLAST search of a database for relatedness to a single polypeptide sequence. Other searches may be conducted using profile based methods, such as the HMM (Hidden Markov model) META-MEME, which is maintained by South Dakota State University, SD, and PSI-BLAST, which is maintained by the National Center for Biotechnology Information, National Library of Medicine, National Institutes of Health (NCBI).

A polynucleotide molecule can encode for a substantially identical or substantially homologous polypeptide molecule. The degree of identity or homology can be determined by use of computer software such as the WISCONSIN PACKAGE Gap Program. The Gap program in the WISCONSIN PACKAGE version 10.0-UNIX from Genetics Computer Group, Inc. is based on the method of Needleman and Wunsch, 1970. Using the TBLASTN program in the BLAST 2.2.1 software suite (Altschul et al., (1997, or using BLOSUM62 matrix (Henikoff and Henikoff, 1992). A polynucleotide molecule of the present invention can also encode a homolog polypeptide. As used herein, a homolog polypeptide molecule or fragment thereof is a counterpart protein molecule or fragment thereof in a second species (e.g., corn rubisco small subunit is a homolog of *Arabidopsis* rubisco small subunit). A homolog can also be generated by molecular evolution or DNA shuffling techniques, so that the molecule retains at least one functional or structure characteristic of the original polypeptide (see, for example, U.S. Pat. No. 5,811,238).

In a preferred embodiment, any of the polynucleotide molecules of the present invention can be operably linked to a promoter region that functions in a plant cell to cause the production of an mRNA molecule, where the polynucleotide molecule that is linked to the promoter is heterologous with respect to that promoter. As used herein, "heterologous" DNA is any DNA sequence which is not naturally found next to the adjacent DNA. "Native" refers to a naturally occurring nucleic acid sequence. "Heterologous" sequence often originates from a foreign source or species or, if from the same source, is modified from its original form and/or location in the genome.

As used herein, the terms "protein," "peptide molecule," or "polypeptide" includes any molecule that comprises five or more amino acids. It is well known in the art that protein, peptide, or polypeptide molecules may undergo modification, including post-translational modifications, such as, but not limited to, disulfide bond formation, glycosylation, phosphorylation, or oligomerization. Thus, as used herein, the terms "protein," "peptide molecule," or "polypeptide" includes any protein that is modified by any biological or non-biological process. The terms "amino acid" and "amino acids" refer to all naturally occurring L-amino acids. This definition is meant to include norleucine, norvaline, ornithine, homocysteine, and homoserine.

A "protein fragment" is a peptide or polypeptide molecule whose amino acid sequence comprises a subset of the amino acid sequence of that protein. A protein or fragment thereof that comprises one or more additional peptide regions not derived from that protein is a "fusion" protein. Such molecules may be derivatized to contain carbohydrate or other moieties (such as keyhole limpet hemocyanin). Fusion protein or peptide molecules of the present invention are preferably produced via recombinant means.

Plant Constructs and Plant Transformants

One or more of the DNA constructs of the present invention that encode for an asparagine synthetase may be used in plant transformation or transfection. Exogenous genetic material may be transferred into a plant cell and the plant cell regenerated into a whole, fertile, or sterile plant. Exogenous genetic material is any genetic material, whether naturally occurring or otherwise, from any source that is capable of being inserted into any organism.

In a further aspect of the present invention, polynucleotide sequences of the present invention also encode peptides involved in intracellular localization, export, or post-translational modification, for example chloroplast transit peptides.

As used herein, the term "gene" includes a nucleic acid molecule that provides regulation of transcription that includes a promoter that functions in plants, 5' untranslated molecules, e.g., introns and leader sequences, a transcribed nucleic acid molecule and a 3' transcriptional termination molecule.

The polynucleic acid molecules encoding a polypeptide of the present invention may be combined with other non-native, or heterologous sequences in a variety of ways. By "heterologous" sequences it is meant any sequence that is not naturally found joined to the nucleotide sequence encoding polypeptide of the present invention, including, for example, combinations of nucleotide sequences from the same plant that are not naturally found joined together, or the two sequences originate from two different species. The term "operably linked", as used in reference to the physical and function arrangement of regulatory and structural polynucleotide molecules that causes regulated expression of an operably linked structural polynucleotide molecule.

The expression of a DNA construct or transgene means the transcription and stable accumulation of sense or antisense RNA or protein derived from the polynucleotide molecule of the present invention or translation thereof. "Sense" RNA means RNA transcript that includes the mRNA and so can be translated into polypeptide or protein by the cell. "Antisense RNA" means a RNA transcript that is complementary to all or part of a target primary transcript or mRNA and that blocks the expression of a target gene (U.S. Pat. No. 5,107,065, incorporated herein by reference). The complementarity of an antisense RNA may be with any part of the specific gene transcript, i.e., at the 5' non-coding sequence, 3' non-translated sequence, introns, or the coding sequence. "RNA transcript" means the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA.

As used herein, the term plant expression cassette refers to a construct comprising the necessary DNA regulatory molecules operably linked to the target molecule to provide expression in a plant cell.

The DNA construct of the present invention can, in one embodiment, contain a promoter that causes the over expression of the polypeptide of the present invention, where "overexpression" means the expression of a polypeptide either not normally present in the host cell, or present in said host cell at a higher level than that normally expressed from the endogenous gene encoding said polypeptide. Promoters, which can cause the overexpression of the polypeptide of the present invention, are generally known in the art, examples of such that provide constitutive expression pattern include cauliflower mosaic virus 19S promoter and cauliflower mosaic virus 35S promoter (U.S. Pat. No. 5,352,605), figwort mosaic virus 35S promoter (U.S. Pat. No. 6,051,753), sugarcane bacilliform virus promoter (U.S. Pat. No. 5,994,123), commelina yellow mottle virus promoter (Medberry et al., 1992), small subunit of ribulose-1,5-bisphosphate carboxylase promoter, rice cytosolic triosephosphate isomerase promoter, adenine phosphoribosyltransferase promoter, rice actin 1 promoter (U.S. Pat. No. 5,641,876), maize ubiquitin promoter, mannopine synthase promoter and octopine synthase promoter.

Such genetic constructs may be transferred into either monocotyledonous or dicotyledonous plants including, but not limited to alfalfa, apple, *Arabidopsis*, banana, *Brassica campestris*, canola, castor bean, coffee, corn, cotton, cottonseed, chrysanthemum, crambe, cucumber, *Dendrobium* spp., *Dioscorea* spp., eucalyptus, fescue, flax, gladiolus, liliacea, linseed, millet, muskmelon, mustard, oat, oil palms, oilseed rape, peanut, perennial ryegrass, *Phaseolus*, rapeseed, rice, sorghum, soybean, rye, tritordeum, turfgrass, wheat, safflower, sesame, sugarbeet, sugarcane, cranberry, papaya, safflower, and sunflower (Christou, 1996). In a preferred embodiment, the genetic material is transferred into a corn cell.

Transfer of a polynucleotide molecule that encodes a protein can result in expression or overexpression of that polypeptide in a transformed cell or transgenic plant. One or more of the proteins or fragments thereof encoded by polynucleotide molecules of the present invention may be overexpressed in a transformed cell or transformed plant.

In one embodiment, DNA constructs of the present invention comprise a polynucleotide molecule encoding a polypeptide sequence selected from the group consisting of SEQ ID NOs 1, 3, 5, 7, 9, 10, 11, 12, 13, 14, 15, 16 and 17. The invention provides transformed corn cells wherein, relative to an untransformed corn plant without such a DNA construct, the cell has an enhanced asparagine level.

In another embodiment, DNA constructs of the present invention comprise a heterologous DNA molecule operably linked to a corn asparagine synthetase coding sequence, for example, SEQ ID NOs 1, 3, or 5, and the DNA construct is transformed corn cell In a preferred embodiment, DNA constructs of the present invention comprising SEQ ID NO: 3 are provided in a transformed corn cell, and expression of the DNA construct provides a corn plant tissue with increased asparagine or a corn plant seed with increased protein relative to a corn plant not transformed with the DNA construct.

In some embodiments, the levels of one or more products of the AsnS may be increased throughout a plant or localized in one or more specific organs or tissues of the plant. Without limiting the scope of the present invention, several promoter sequences are useful for expressing the gene of the above enzyme. For example, maize C4 type PPDK promoter (Glackin et al., 1990), maize C4 type PEPC promoter (Hudspeth and Grula, 1989), rice Rubisco small subunit promoter (Kyozuka et al., 1993), and light-harvesting chlorophyll a/b binding protein promoter (Sakamoto et al., 1991), the P-FDA promoter (US20040216189A1, the polynucleotide sequence of which is herein incorporated by reference) and P-RTBV promoter (U.S. Pat. No. 5,824,857, the polynucleotide sequence of which is herein incorporated by reference). For example the levels of asparagine or protein may be increased in one or more of the tissues and organs of a plant including without limitation: roots, tubers, stems, leaves, stalks, fruit, berries, nuts, bark, pods, seeds, and flowers. A preferred organ is a seed.

For the purpose of expression in source tissues of the plant, such as the leaf, seed, root, or stem, it is preferred that the promoters utilized have relatively high expression in these specific tissues. Tissue-specific expression of a protein of the present invention is a particularly preferred embodiment.

DNA constructs or vectors may also include, with the coding region of interest, a polynucleotide sequence that acts, in whole or in part, to terminate transcription of that region. A number of such sequences have been isolated, including the T-NOS 3' region (Ingelbrecht et al., 1989; Bevan et al., 1983). Regulatory transcript termination regions can be provided in plant expression constructs of this present invention as well. Transcript termination regions can be provided by the DNA sequence encoding the gene of interest or a convenient transcription termination region derived from a different gene source, for example, the transcript termination region that is naturally associated with the transcript initiation region. The skilled artisan will recognize that any convenient transcript termination region that is capable of terminating transcription in a plant cell can be employed in the constructs of the present invention.

A vector or construct may also include regulatory elements, such as introns. Examples of such include, the Adh intron 1 (Callis et al., 1987), the sucrose synthase intron (Vasil et al., 1989), hsp70 intron (U.S. Pat. No. 5,859,347), and the TMV omega element (Gallie et al., 1989). These and other regulatory elements may be included when appropriate.

A vector or construct may also include a selectable marker. Selectable markers may also be used to select for plants or plant cells that contain the exogenous genetic material. Examples of such include, but are not limited to: a neo gene (Potrykus et al., 1985), which codes for kanamycin resistance and can be selected for using kanamycin, nptII, G418, hpt, etc.; a bar gene, which codes for bialaphos resistance; a mutant EPSP synthase gene (Hinchee et al., 1988; Reynaerts et al., 1988; Jones et al., 1987), which encodes glyphosate resistance; a nitrilase gene which confers resistance to bromoxynil (Stalker et al., 1988); a mutant acetolactate synthase gene (ALS) which confers imidazolinone or sulphonylurea resistance (U.S. Pat. No. 4,761,373); D'Halluin et al., 1992); and a methotrexate resistant DHFR gene (Thillet et al., 1988).

Plant Transformation

The most commonly used methods for transformation of plant cells are the *Agrobacterium*-mediated DNA transfer process and the biolistics or microprojectile bombardment mediated process (i.e., the gene gun). Typically, nuclear transformation is desired but if it is desirable to specifically transform plastids, such as chloroplasts or amyloplasts, plant plastids may be transformed utilizing a microprojectile-mediated delivery of the desired polynucleotide.

The methods for introducing transgenes into plants by *Agrobacterium*-mediated transformation utilize a T-DNA (transfer DNA) that incorporates the genetic elements of the transgene and transfers those genetic elements into the genome of a plant. Generally, the transgene(s) bordered by a right border DNA molecule (RB) and a left border DNA molecule (LB) is (are) transferred into the plant genome at a single locus. The "T-DNA molecule" refers to a DNA molecule that integrates into a plant genome via an *Agrobacterium* mediated transformation method. The ends of the T-DNA molecule are defined in the present invention as being flanked by the border regions of the T-DNA from *Agrobacterium* Ti plasmids. These border regions are generally referred to as the Right border (RB) and Left border (LB) regions and exist as variations in nucleotide sequence and length depending on whether they are derived from nopaline or octopine producing strains of *Agrobacterium*. The border regions commonly used in DNA constructs designed for transferring transgenes into plants are often several hundred polynucleotides in length and comprise a nick site where an endonuclease digests the DNA to provide a site for insertion into the genome of a plant. T-DNA molecules generally contain one or more plant expression cassettes.

With respect to microprojectile bombardment (U.S. Pat. Nos. 5,550,318; 5,538,880; and 5,610,042; each of which is specifically incorporated herein by reference in its entirety), particles are coated with polynucleotides and delivered into cells by a propelling force. Exemplary particles include those comprised of tungsten, platinum, and preferably, gold. A useful method for delivering DNA into plant cells by particle acceleration is the Biolistics Particle Delivery System (Bio-Rad, Hercules, Calif.), which can be used to propel particles coated with DNA or cells through a screen, such as a stainless steel or Nytex screen, onto a filter surface covered with monocot plant cells cultured in suspension. Microprojectile bombardment techniques are widely applicable, and may be used to transform virtually any plant species. Examples of species that have been transformed by microprojectile bombardment include monocot species such as corn (PCT Publication WO 95/06128), barley, wheat (U.S. Pat. No. 5,563,055, incorporated herein by reference in its entirety), rice, oat, rye, sugarcane, and sorghum; as well as a number of dicots including tobacco, soybean (U.S. Pat. No. 5,322,783, incorporated herein by reference in its entirety), sunflower, peanut, cotton, tomato, and legumes in general (U.S. Pat. No. 5,563,055, incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker would include but are not limited to GUS, green fluorescent protein (GFP), luciferase (LUX), and antibiotic or herbicide tolerance genes. Examples of antibiotic resistance genes include those conferring resistance to kanamycin (and neomycin, G418), and bleomycin.

The regeneration, development, and cultivation of plants from various transformed explants are well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. Developing plantlets are transferred to soil-less plant growth mix, and hardened off, prior to transfer to a greenhouse or growth chamber for maturation.

The present invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

Any suitable plant culture medium can be used. Examples of suitable media would include but are not limited to MS-based media (Murashige and Skoog, 1962) or N6-based media (Chu et al., 18:659, 1975) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Those of skill in the art are aware that media and media supplements such as nutrients and growth regulators for use in transformation and regeneration and other culture conditions such as light intensity during incubation, pH, and incubation temperatures that can be optimized for the particular variety of interest.

Any of the polynucleotide molecules of the present invention may be introduced into a plant cell in a permanent or transient manner in combination with other genetic elements such as vectors, promoters, enhancers, etc. Further, any of the polynucleotide molecules of the present invention may be introduced into a plant cell in a manner that allows for expression or overexpression of the protein or fragment thereof encoded by the polynucleotide molecule.

The present invention also provides for parts of the plants, particularly reproductive or storage parts, of the present invention. Plant parts, without limitation, include seed, endosperm, ovule, pollen, or tubers. In a particularly preferred embodiment of the present invention, the plant part is a corn seed. In one embodiment the corn seed (or grain) is a constituent of animal feed.

In a preferred embodiment the corn feed or corn meal or protein from the corn seed is designed for livestock animals or humans, or both. Methods to produce feed, meal, and protein, are known in the art. See, for example, U.S. Pat. Nos. 4,957, 748; 5,100,679; 5,219,596; 5,936,069; 6,005,076; 6,146,669; and 6,156,227. In a preferred embodiment, the protein preparation is a high protein preparation. Such a high protein preparation preferably has a protein content of greater than about 5% (w/v), more preferably 10% (w/v), and even more preferably 15% (w/v).

Descriptions of breeding methods that are commonly used for different traits and crops can be found in one of several reference books (e.g., Hayward, 1993; Richards, 1997; Allard, 1999).

Other Organisms

A polynucleotide of the present invention may be introduced into any cell or organism such as a mammalian cell, mammal, fish cell, fish, bird cell, bird, algae cell, algae, fungal cell, fungi, or bacterial cell. A protein of the present invention may be produced in an appropriate cell or organism. Preferred host and transformants include: fungal cells such as *Aspergillus*, yeasts, mammals, particularly bovine and porcine, insects, bacteria, and algae. Particularly preferred bacteria are *Agrobacterium tumefaciens* and *E. coli*.

In an aspect of the present invention, one or more of the nucleic acid molecules of the present invention are used to determine the level of expression (i.e., the concentration of mRNA in a sample, etc.) in a plant (preferably canola, corn, *Brassica campestris*, oilseed rape, rapeseed, soybean, crambe, mustard, castor bean, peanut, sesame, cottonseed, linseed, safflower, oil palm, flax or sunflower) or pattern (i.e., the kinetics of expression, rate of decomposition, stability profile, etc.) of the expression of a protein encoded in part or whole by one or more of the polynucleotide molecule of the present invention. A number of methods can be used to compare the expression between two or more samples of cells or tissue. These methods include hybridization assays, such as northerns, RNAase protection assays, and in situ hybridization. Alternatively, the methods include PCR-type assays. In a preferred method, expression is assessed by hybridizing polynucleotides from the two or more samples to an array of polynucleotides. The array contains a plurality of suspected sequences known or suspected of being present in the cells or tissue of the samples.

The following examples are included to demonstrate aspects of the invention, those of skill in the art should, in light of the present disclosure, appreciate that many changes can be made in the specific aspects which are disclosed and still obtain a like or similar result without departing from the spirit and scope of the invention.

EXAMPLES

Those of skill in the art will appreciate the many advantages of the methods and compositions provided by the present invention. The following examples are included to demonstrate the preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention. All references cited herein are incorporated herein by reference to the extent that they supplement, explain, provide a background for, or teach methodology, techniques, or compositions employed herein.

Example 1

Construction of Corn and Soy Plant cDNA and Genomic Libraries

This example describes the production of cDNA libraries made from corn and soy plant tissues from which the corn AsnS and soy polynucleotide sequences of the present invention were isolated. cDNA Libraries were generated from *Zea mays* and *Glycine max* tissue using techniques known in the art, for example, Alba, 2004. Corn cDNA libraries were made from two different tissues. A library was made from incipient kernels harvested at the dilatory phase from inbred line 90DDD5. A second corn cDNA library was made from silk tissue at the silking growth stage from corn inbred line H99 and germinating pollen from corn inbred line MO17. For construction of a cDNA library from soybean (*Glycine max*), meristematic tissue and part of the hypocotyl were excised from rehydrated dry soybean seeds of variety A3237 (Asgrow). Explants were prepared by first germinating surface sterilized seeds on solid tissue culture media for 6 days at 28° C. at 18 hours of light/day, and then transferring germinated seeds to 4° C. for at least 24 hours. For the tissue used in library preparation the cotyledons were removed to enrich for the specific tissue of interest. 0.5 to 2 grams of tissue were used for preparation of total RNA and poly A+ RNA. For all cDNA libraries, plant tissues were harvested and immediately frozen in liquid nitrogen. The harvested tissue was stored at −80° C. until preparation of total RNA. The total RNA was purified using Trizol reagent from Invitrogen Corporation (Invitrogen Corporation, Carlsbad, Calif., U.S.A.), essentially as recommended by the manufacturer. Poly A+ RNA (mRNA) was purified using magnetic oligo dT beads essentially as recommended by the manufacturer (Dynabeads, Dynal Biotech, Oslo, Norway).

Construction of plant cDNA libraries is well known in the art and a number of cloning strategies exist. A number of cDNA library construction kits are commercially available. cDNA libraries were prepared using the Superscript™ Plasmid System for cDNA synthesis and Plasmid Cloning (Invitrogen Corporation), as described in the Superscript II cDNA library synthesis protocol. The cDNA libraries were checked to confirm an appropriate insert:vector ratio.

A genomic DNA library was constructed using genomic DNA isolated from *Zea mays* using a modified genomic DNA isolation protocol described below (Dellaporta et al., 1983). Corn seedlings were grown in soil or in Petri plates, were harvested, and kept frozen in liquid nitrogen until extraction. The tissue was ground to a fine powder using a mortar and pestle while keeping the tissue frozen with liquid nitrogen. The powdered tissue was transferred to a Waring blender containing 200 mL of cold (0° C.) DNA extraction buffer (350 mM sorbitol; 100 mM Tris; 5 mM EDTA; pH to 7.5 with HCl; sodium bisulfite, 3.8 mg/mL) that was added just before use, and homogenized at high speed for 30-60 seconds. The homogenate was filtered through a layer of cheesecloth and collected in a centrifuge bottle. The samples were then centrifuged at 2500×g for 20 minutes, and the supernatant and any loose green material were discarded. The pellet was then resuspended in 1.25 mL of DNA extraction buffer and transferred to a 50 mL polypropylene tube. Nuclei lysis buffer (1.75 mL containing 200 mM Tris; 50 mM EDTA; 2 M NaCl; 2.0% (w/v) CTAB; pH adjusted to 7.5 with HCl) was then added, followed by addition of 0.6 mL of 5% (w/v) sarkosyl. The tubes were mixed gently, and the samples were incubated at 65° C. for 20 minutes. An equal volume of chloroform: isoamyl alcohol (24:1) was added and the tubes were again mixed gently. The tubes were then centrifuged at 2500×g for 15 minutes, and the resulting supernatant was transferred to a clean tube. An equal volume of ice-cold isopropanol was poured onto the sample, and the sample was inverted several times until a precipitate formed. The precipitate was removed from the solution using a glass pipette and residual alcohol removed by allowing the precipitate to air dry for 2-5 minutes. The precipitate was resuspended in 400 μL TE buffer (10 mM Tris-HCl, 1 mM EDTA, pH adjusted to 8.0).

Example 2

Isolation of AsnS Polynucleotide Sequences by Ligation Independent and Gateway Cloning Methods and Corn Transformation This example illustrates the isolation of polynucleotide molecules encoding AsnS using ligation independent and Gateway® cloning methods and the construction of DNA constructs of the present invention that comprise the polynucleotide molecules that encode AsnS polypeptides isolated from various plant and microorganisms sources as described in Table 1. The promoter molecules used to drive the expression of the linked AsnS-encoding polynucleotide molecules are the rice actin 1 promoter, P-Os.Act1 (U.S. Pat. No. 5,641,876, herein incorporated by reference); the *Zea mays* PPDK (Matsuoka et al., 1993), P-RTBV-1 (U.S. Pat. No. 5,824,857, herein incorporated by reference), and the P-Zm. NAS (promoter molecule of the genomic region coding for a nicotianamine synthase 2 polypeptide from corn).

TABLE 1

AsnS coding sequence source, promoter and DNA constructs

| SEQ ID NO: | Coding sequence source | Promoter | Exemplary DNA construct |
|---|---|---|---|
| 3 | *Zea mays* AsnS2 | P-Os.Act1 | pMON79706 |
| 5 | *Zea mays* AsnS3 | P-Os.Act1 | pMON92870 |
| 7 | *Glycine max* | P-Os.Act1 | pMON79700 |
| 17 | *Saccharomyces cerevisiae* | P-Os.Act1 | PMON79653 |

Ligation independent cloning was developed to clone PCR products and is based on the annealing of non-palindromic single-stranded ends. LIC is an efficient cloning method, which is not limited by restriction sites or the need for restriction enzyme digestion or ligation reactions and leaves seamless junctions (Aslanidis and de Jong, 1990).

Terminal, single-stranded DNA segments are produced in the vector through the use of a "nicking endonuclease" and restriction endonuclease. A nicking endonuclease is an endonuclease that nicks one strand of the polynucleotide duplex to create single stranded tails on the cloning vector. The vector is first linearized with a standard restriction endonuclease. This is then followed by digestion with a nicking endonuclease. After heat treatment, terminal, single-stranded DNA segments are produced in the vector. A GC content of roughly 55% is recommended for downstream PCR amplification and efficient annealing. The promoter, tag, or other sequence element can be added to the 5' and 3' ends of the PCR-amplified product to create a linear construct that can be used in downstream applications.

The DNA construct pMON92870 was assembled from the base vector, pMON82060, and a corn AsnS3 polynucleotide molecule encoding an AsnS polypeptide provided as SEQ ID NO 5. The plasmid backbone pMON82060 was linearized using the restriction endonuclease, HpaI. The plasmid backbone was then treated with the nicking endonuclease, N.BbvC IA (New England Biolabs, Beverly, Mass.). After digestion, the reaction was heated to 65° C. This causes the nicked strands of DNA to disassociate from their complementary DNA strands. The resulting linearized plasmid backbone was left with two terminal, single-stranded DNA segments available for assembly.

The polymerase chain reaction was employed to produce the terminal single-stranded DNA segments in the DNA molecule encoding AsnS. The corn AsnS3 polynucleotide sequence (SEQ ID NO: 5) encoding the AsnS polypeptide was used for the design of the forward PCR primer (SEQ ID NO: 48) and the reverse PCR primer (SEQ ID NO: 49):

```
SEQ ID NO: 48:
GCAGTCGCTGTCGTTACCCGGCATCATGTGGCATC

SEQ ID NO: 49:
GCGAGTACCGCTGGGTTCTAACGTACTCTCGTCAGACCGCG
```

Polymerase chain reaction amplification was performed using the high fidelity thermal polymerase, KOD hot start DNA polymerase (Novagen, Madison, Wis.). The polymerase chain reaction was performed in a 25 µL volume containing, 1×KOD hot start DNA polymerase buffer, 1M betaine (Sigma, St. Louis, Mo.), 1 mM MgSO4, 250 µM dNTPs, 5 pmols of each primer and 1 unit of KOD hot start DNA polymerase. The polymerase chain reaction was performed in a PTC-225 DNA Engine Tetrad™ thermal cycler (MJ Research Inc., Waltham, Mass.) using the following cycler parameters:
1. 94° C. for 2 minutes
2. 94° C. for 15 seconds
3. 70° C. for 30 seconds (−1° C. per cycle)
4. 72° C. for 5 minutes
5. Go to step 2, 9 times
6. 94° C. for 15 seconds
7. 60° C. for 30 seconds
8. 72° C. for 5 minutes
9. Go to step 6, 24 times
10. 72° C. for 10 minutes
11. 10° C. hold
12. end A second round of polymerase chain reaction was performed to introduce uridine residues in the region in which the terminal, single-stranded DNA segments were produced. Many DNA polymerases are unable to read uridine residues in the template strand of DNA or are unable to polymerize strands using uridine residues. Polymerase chain reaction was therefore performed using an enzyme capable of incorporating and reading uridines (Expand High Fidelity™ plus PCR System; Roche, Indianapolis, Ind.). Modification of this method and use of other methods that provide the expected result are known by those skilled in the art.

The assembled DNA construct was transformed into ElectroMAX™ DH10B *E. coli* competent cells (Invitrogen, Carlsbad, Calif.). A 0.54 (microliter) aliquot from the assembly reaction was mixed with 20 µL of ElectroMAX™ DH10B competent cells on ice and loaded into a MicroPulser 0.2 mm electroporation cuvette (Bio-Rad Laboratories Inc., Hercules Calif.) for electroporation. Cells were subjected to electroporation at 1.8 kV using a 165-2100 MicroPulser Electroporator (Bio-Rad Laboratories Inc.). Electroporated cells were incubated in 180 µL of SOC medium (Invitrogen Inc.) at 37° C. for 1 hour. Cells were then plated onto LB agar plates containing spectinomycin (75 mg/L) and grown overnight at 37° C. Colonies were selected and grown in LB media overnight at 37° C. The plasmid DNA construct was isolated using the QIAprep® Spin Miniprep Kit (QIAgen Sciences, Valencia, Calif.). DNA sequencing was performed on an ABI 3730×1 DNA Analyzer, using BigDye® terminator (Applied Biosystems, Foster City, Calif.).

The cloning of corn AsnS2, soy AsnS, and yeast AsnS1 AsnS-encoding polynucleotide sequences was accomplished using the "Gateway® cloning method" as described by the manufacturer (Invitrogen Corp.). The goal of the Gateway® cloning method is to make an expression clone. This two-step process involves first, the cloning of the gene of interest into an entry vector, followed by subcloning of the gene of interest from the entry vector into a destination vector to produce an expression vector. The cloning technology is based on the site-specific recombination system used by phage lambda to integrate its DNA into the *E. coli* chromosome.

DNA constructs for use in subsequent recombination cloning, two attB or attR recombination sequences were cloned into a recombinant vector flanking a Spectinomycin/Streptomycin resistance gene (SPC/STR) and an AsnS-encoding polynucleotide sequence. The AsnS-encoding polynucleotide sequences were isolated from cDNA or genomic libraries made from their respective species using the primary and secondary primer sequences (SEQ ID NOs 20-43). The contiguous attB1/R1, SPC/STR gene, AsnS gene, and attB2/R2 sequences were moved as a single polynucleotide molecule into a recombinant construct for expression in plant cells, the double-stranded DNA plasmids designated pMON79706 (*Zea mays* AsnS2), pMON79700 (*Glycine max* AsnS) or pMON79653 (*Saccharomyces cerevisiae* AsnS). These DNA constructs comprise the *Agrobacterium* right border (O-OTH.-RB) regions and left border (LB) regions, and others disclosed by Herrera-Estrella et al., 1983; Bevan, 1984; Klee et al., 1985, the e35S promoter (P-CAMV. 35S, tandemly duplicated enhancer U.S. Pat. No. 5,322,938), the attB1/R1 genetic element (O-Lam. attB1/R1), the SPC/STR gene, the respective AsnS-coding region (CR), the attB2/R2 genetic element (O-Lam.attB2/R2), the potato protease inhibitor II terminator (St.Pis), the *Agrobacterium* NOS promoter (P-AGRtu..nos, Fraley et al., 1983), the *Agrobacterium* left border (O-OTH.-LB), the kanamycin resistance gene (CR-OTH.-Kan, U.S. Pat. No. 6,255,560), and the *E. coli* origin of replication (Ec.ori.ColE).

The DNA constructs were amplified in Library Efficiency® DB3.1™ cells (Invitrogen Corporation) under chloramphenicol selection (25 µg/mL) and kanamycin selection (50 µg/mL) for pMON79706, pMON79700 or pMON79653. Vector DNA was purified from bacterial cultures using a QIAGEN Plasmid Kit (QIAGEN Inc.).

DNA for pMON79700, pMON79706, and pMON79653 was introduced into the corn embryos as described in U.S. Pat. No. 5,015,580, using the electric discharge particle acceleration gene delivery device. For microprojectile bombardment of LH59 pre-cultured immature embryos, 35% to 45% of maximum voltage was preferably used. Following microprojectile bombardment, the corn tissue was cultured in the dark at 27° C. Transformation methods and materials for making transgenic plants of this invention, for example, various media and recipient target cells, transformation of immature embryos and subsequent regeneration of fertile transgenic plants are disclosed in U.S. Pat. Nos. 6,194,636 and 6,232,526 and U.S. Patent Application Publication 20040216189, which are incorporated herein by reference.

Fertile transgenic corn plants were produced from transformed corn cells by growing transformed callus on the appropriate regeneration media to initiate shoot development and plantlet formation. Plantlets were transferred to soil when they were about 3 inches tall and possessed roots (about four to 6 weeks after transfer to medium). Plants were maintained for two weeks in a growth chamber at 26° C., followed by two weeks on a mist bench in a greenhouse. The plants were subsequently transplanted into 5-gallon pots and grown to maturity in the greenhouse. Reciprocal pollinations were made with the corn LH59 inbred line. Seed was collected from corn plants and used for analysis of protein and further breeding activities.

Example 3

Vector Construction and Transformation of Corn with AsnS Polynucleotide Sequences The corn AsnS2 (SEQ ID NO: 3, pMON79706, FIG. 1) was amplified by use of PCR (polymerase chain reaction). The reaction conditions for the PCR reaction followed the manufacturer's protocol (PE Applied Biosystems, Foster City, Calif.). Approximately 100 ng of corn DNA, prepared as described above, was amplified using 30 nmole each of forward (f) primer (SEQ ID NO: 32) and reverse (r) primer (SEQ ID NO: 33) and 10 micromoles each of dATP, dCTP, dGTP and TTP, 2.5 units of TaKaRaLA Taq in 1× LA PCR Buffer II (Takara Bio INC, Shiga, Japan). After initial incubation at 94° C. for 1 minute, 35 cycles of PCR were performed at 94° C. for 45 seconds, followed by annealing at 60° C. for 45 seconds, 72° C. for 1 minute 15 seconds, followed, by 1 cycle of 72° C. for 7 minutes.

Figure 3:
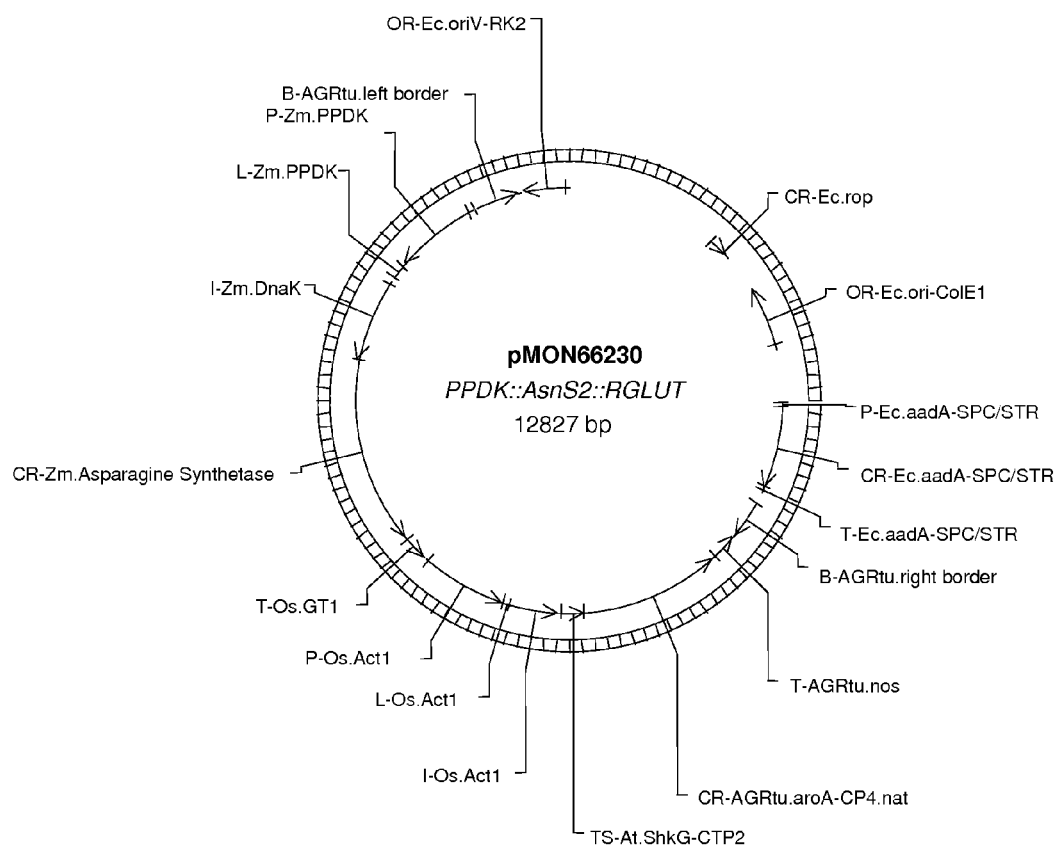
FIG. 3 illustrates the plasmid map of pMON66230.

Five AsnS2 DNA constructs were made. The first corn AsnS2 construct was made by isolating an 1821 base pair AsnS2 fragment from pMON79706 by PCR, as described above, followed by restriction digestion with XbaI and EcoRI restriction enzymes. The resulting AsnS2 gene was ligated into pMON61560, which had also been digested with XbaI and EcoRI. The resulting shuttle vector (pMON66246) was digested with NotI and the insert containing the AsnS2 gene, in operable linkage with the PPDK promoter and RGLUT1 terminator, was ligated into pMON30167, which had also been digested with NotI. The pMON30167 plasmid, which contains the EPSPS gene, provides for selection with glyphosate. The resulting final plasmid was designated pMON66230 (FIG. 3).

Figure 2:
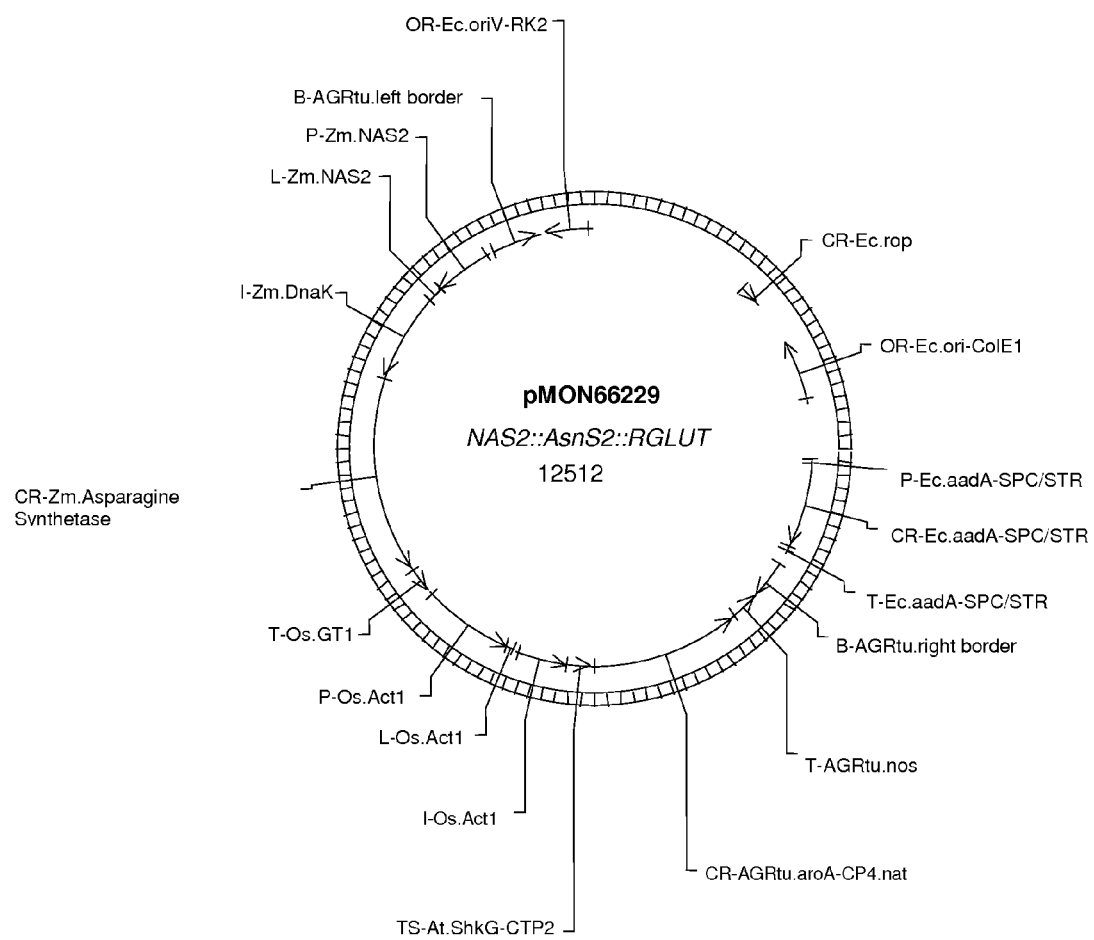
FIG. 2 illustrates the plasmid map of pMON66229.

A second AsnS2 construct was made using the aforementioned AsnS2 (pMON79706) gene. The construct was made by insertion of the XbaI/EcoRI digested AsnS2 gene into pMON61562, which had also been digested with XbaI and EcoRI, resulting in the AsnS2 gene being in operable linkage with the NAS promoter and RGLUT1 terminator. The resulting plasmid was digested with NotI and ligated into the NotI digested pMON30167. The resulting plasmid was designated pMON66229 (FIG. 2).

Figure 4:
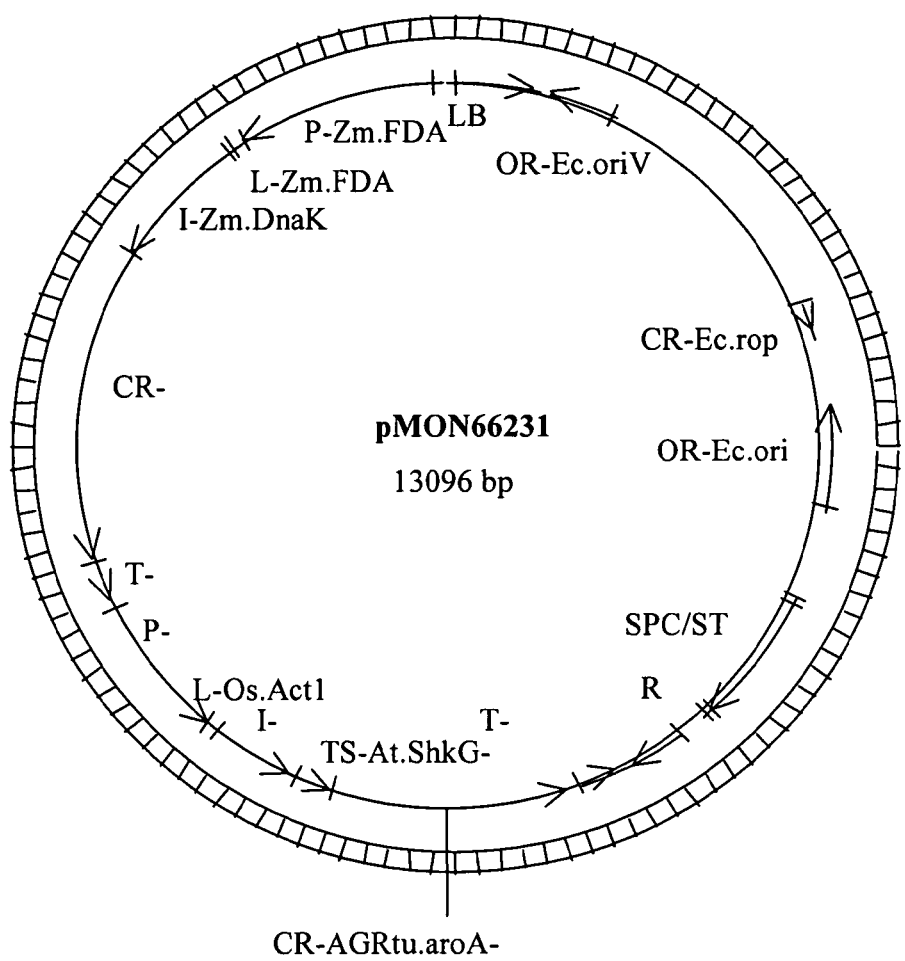
FIG. 4 illustrates the plasmid map of pMON66231.

A third AsnS2 construct was made using the aforementioned AsnS2 gene (pMON79706). The P-FDA promoter used in this construct was isolated from pMON78810 by digestion with NotI and XbaI restriction enzymes. The P-FDA promoter was then ligated into pMON66246, which was previously digested with NotI and XbaI to remove its PPDK promoter. The resulting plasmid was digested with NotI and ligated into the NotI digested pMON30167. The resulting plasmid was designated pMON66231 (FIG. 4).

Figure 5:
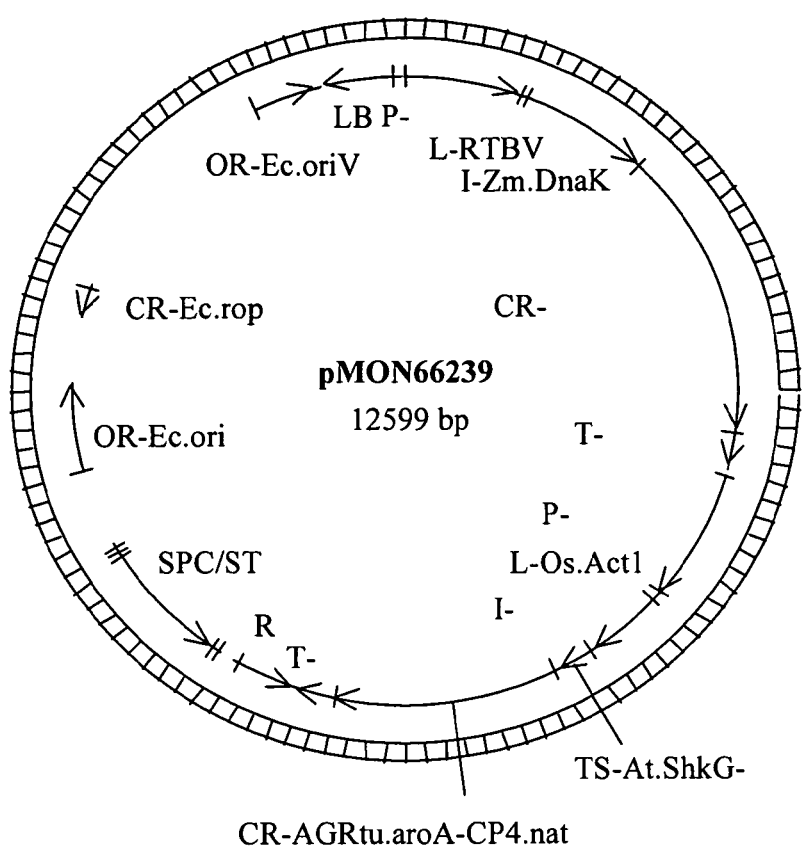
FIG. 5 illustrates the plasmid map of pMON66239.

A fourth AsnS2 construct was made using the aforementioned AsnS2 gene (pMON79706). The P-RTBV promoter to be used in this construct was generated by PCR from pMON74576. The 721 by fragment was digested with NotI and XbaI and ligated into pMON66246, which was previously digested with NotI and XbaI. The resulting plasmid, containing the AsnS2 gene in operable linkage with the P-RTBV promoter and RGLUT1 terminator was digested with NotI and ligated into the NotI digested pMON30167. The resulting plasmid was designated pMON66239 (FIG. 5).

A fifth AsnS2 construct was made using the aforementioned AsnS2 gene (pMON79706). A primer pair of ZmASsense,

5'TCCTAGACATGTCCGGCATACTTGCTG3' (SEQ ID NO:46), and ZmASantisense,

5'TGCAGAATTCTATCCCTCGATGG; (SEQ ID NO:47), was used to amplify corn AsnS2 from pMON66240. PCR set up was as follows: in a total volume of 50 ul PCR reaction, 1 µl of 10 mM each primer of ZmASsense and ZmASantisense, 0.2 to 0.5 µg (1 µl) of plasmid DNA of pMON66240, 5 µl of 10× AccuPrime™ Pfx Reaction Mix, 1 µl of ACCuPrime™ Pfx DNA Polymerase (Invitrogen), and 41 µl of distilled water. The PCR reaction was carried out with the following cycle parameters: 94° C. for 1 min., followed by 30 cycles of 94° C. for 15 seconds for denaturing; 58° C. for 15 sec of annealing, and 68° C. for 4 min.; followed by 10 min. of extension at 68° C. The PCR product was purified using a PCR purification kit from QIAGEN (QIAGEN Inc.). An aliquot of the PCR corn AsnS2 product was digested with NcoI and EcoRI restriction enzyme and another aliquot of the PCR product was digested with AflIII and NcoI. The NcoI and EcoRI fragment was then cloned into NcoI and EcoRI sites of pMON94901. The AflIII and NcoI 5' end fragment of corn AsnS2 was cloned into the NcoI and EcoRI of the corn AsnS2 fragment at NcoI site. The resulting plasmid (pMON74940), containing corn AsnS2 in operable linkage with the e35S promoter and the Hsp17 terminator, was digested with NotI and ligated into NotI digested pMON53616 to construct pMON74946.

Each construct described above contained an expression cassette for expression of a glyphosate insensitive Type II EPSPS as a means for selecting transgenic events (U.S. Pat. No. 5,633,435). The nucleic acid sequence of each construct was determined using standard methodology as set forth by PE Applied Biosystems BigDye terminator v.3.0 (PE Applied Biosystems, Foster City, Calif.) and the integrity of the cloning junctions confirmed. The pMON66229, pMON66230, pMON66231, pMON66239, and pMON74946 vectors were used in the subsequent transformation of corn cells and regeneration of these cells into intact corn plants. Constructs of interest were introduced to immature embryos from corn line LH244 by an *Agrobacterium*-mediated transformation method, for instance as described in U.S. Published Patent Application 20050048624.

Example 4

Protein and Amino Acid Analysis of Corn Seed Samples

This example sets forth a method of protein and amino acid analysis to select seed of the present invention with increased asparagine and protein using HPLC and near infrared measurements. For seed protein analysis, small bulk samples consisting of 50-100 seeds for each treatment were measured using near infrared transmittance spectroscopy (Infratec model 1221, Tecator, Hoganas Sweden). This procedure was based upon the observation that a linear relation exists between the absorption of near infrared radiation and the quantity of chemical constituents comprised in a typical seed sample. Prior to analyzing unknown samples, spectral data was collected with calibration samples that were subsequently analyzed using a primary analysis technique. The primary technique used was nitrogen combustion (Murray and Williams, 1987). A multivariate model was developed using the spectral data from the spectrometer and the primary data. In the present case, a PLS-1 (Partial Least Squares Regression Type I) multivariate model was constructed using 152 calibration samples. Each unknown sample was scanned on the spectrometer at least five times and its protein content predicted with each scan. Each time the sample was scanned, it was added back to the sample cuvette to provide an accurate representation of the sample tested. The predicted protein values were averaged for the multiple scans and then reported for each sample.

Free amino acid analysis was performed on corn tissues by HPLC. For each sample, 20-50 mg lyophilized tissue were extracted with 1.5 mL of 10% trichloroacetic acid in 2-mL microfuge tubes. Samples were extracted at room temperature overnight with gentle shaking. Extracted samples were cleared by centrifugation and the supernatant was removed for further analysis. Free amino acid analysis was performed by HPLC on an Agilent Series 1100 HPLC with a fluorescence detector and 96-well plate autosampler equipped with a Zorbax Eclipse AAA C18 column (4.6×75 mm, 3.5 micron, Agilent Technologies, Palo Alto, Calif.) and Zorbax Eclipse AAA analytical guard column (4.6×12.5 mm, 5 micron). Samples were pre-derivatized with o-pthalaldehyde immediately prior to separation. Free amino acids were resolved with a 40 mM phosphate buffer, pH 7.6/Methanol/Acetonitrile gradient followed by fluorescence detection at 340 nm/450 nm (excitation/emission). Free amino acids were quantified based on external amino acid standards and peaks were integrated with ChemStation software (Agilent). Relative standard deviations were typically less than 8%.

Example 5

Field Evaluation of Asparagine Levels and Grain Protein Content in Transgenic Corn Plants This example sets forth the results of a field evaluation of the effects of the corn AsnS constructs (pMON79706 and pMON92870) on asparagine and protein levels in transformed corn plants and seed; and the effects of the corn AsnS constructs (pMON79700 and pMON79653) on grain protein content. The relative concentration of free asparagine in corn tissues was obtained from inbred lines derived from $R_0$ corn plants transformed with pMON79706 or pMON92870. For pMON79706, $R_0$ transformants were backcrossed to the parent inbred, LH59, to create $BC_1$ seed. The $BC_1$ seed, which segregates with the transgene, was planted in a field nursery and individual plants were scored for the presence of the NPTII marker gene. Leaf tissue was collected for free amino acid analysis from transgene-positive and transgene-negative plants for each transgenic event for free amino acid analysis. Leaf free amino acids of pMON79706 transgenic plants were compared to negative isoline plants within each event and analyzed statistically by Student's T test with JMP 5.1 software (SAS Institute, Cary, N.C.). For pMON92870, $R_0$ transformants were backcrossed to the parent inbred, LH244, to create $BC_1$ seed. The BC1 seed was planted in a field nursery and self-pollinated to create the $BC_1S_1$ seed, which subsequently was planted in a second inbred nursery. Transgene-positive plants were identified for each transgenic event following scoring for the presence of the NPTII marker gene. Leaf tissue was collected from transgene-positive $BC_1S_1$ plants and parental inbred plots planted at regular intervals in the nursery. Leaf free amino acids for pMON92870 were analyzed statistically by performing analysis of variance and comparing transgenic entries to the parental control by conducting Student's T test using SAS 9.1 software. For free amino acid analyses for both constructs, leaf tissue was collected by removal of an upper fully expanded leaf at anthesis followed by freezing on dry ice. Leaf samples were ground frozen, lyophilized, and measured for free amino acid content by HPLC.

Multiple transgenic events of pMON79706 and pMON92870 were observed to show substantial increases in leaf asparagine content (Table 2). Four of seven events of pMON79706 tested showed significant increases in the concentration of leaf asparagine, as indicated by a p value of 0.05 or less. In transgenic events of pMON92870, expressing a second maize asparagine synthetase gene, four of five events showed significant increases in leaf asparagine levels (Table 2). These data show that transgenic expression of maize AsnS2 and maize AsnS3 under the rice actin promoter in pMON79706 and pMON92870, respectively, can result in a specific increase in free asparagine, which is consistent with the overexpression of active asparagine synthetase.

The relative concentration of protein in corn seed was obtained from inbred lines derived from $R_0$ corn plants transformed with pMON79706 or pMON92870. $BC_1$ transgenic plants of pMON79706 (described above) were self-pollinated and the resulting $BC_1S_1$ grain was grown to maturity and measured for protein content by single ears. Protein was measured as a percentage of dry weight at 0% moisture. Grain protein for pMON79706 transgenic plants were compared to negative isoline plants within each event and analyzed statistically by Student's T test with SAS 9.1 software. For pMON98270, $BC_1S_1$ plants were self-pollinated and grown to maturity and measured for protein content by single ears. Grain protein for pMON92870 was analyzed statistically with a custom developed spatial method by conducting a by-location analysis. The by-location analysis is a two-step process. The first step in the analysis involved estimating the spatial autocorrelation in the field by fitting an anisotropic spherical semi-variogram model using all spatial check plots that were placed systematically in the field (every 6th plot). The second stage of analysis involved adjusting the values of the transgenic entries for the spatial variability using the spatial autocorrelation structure estimated in the first stage of the analysis. Following the adjustment for spatial autocorrelation, mean comparison was carried out where the mean value of a transgenic entry was compared to the parental control to test the statistical significance of the difference between a transgene and the control mean.

Multiple events of both pMON79706 and pMON92870 showed significant increases in inbred grain protein content (Table 3). Three of five events of pMON79706 that were analyzed statistically showed significant increases in grain protein content (p<0.05) and two other events showed trends toward significant increases (p<0.15). Two events did not return sufficient numbers of ears for a statistical analysis. Three of four transgenic events of pMON92870 showed significant increases in grain protein content (p<0.1), with one event untested due to insufficient numbers of ears for analysis. These data confirm that pMON79706 and pMON92870 produce transgenic events that increase grain protein content in maize in addition to increasing leaf asparagine content.

free asparagine. Relative free asparagine levels in V8 leaf tissue were increased up to 13.9% as compared to 3.4% in the LH59 variety control, and stem asparagine was increased up to 39% as compared to 9.6 in the control (Table 4). For grain

TABLE 2

Relative leaf asparagine concentrations in inbred maize transformed with corn AsnS2 gene (pMON79706) or corn AsnS3 gene (pMON92870).

| Construct[a] | Event | Generation | Mean of Transgene-positive Plants[b] | Mean of Transgene-negative Plants | Diffe ence | p value |
|---|---|---|---|---|---|---|
| pMON79706 | ZM__M50965 | $BC_1$ | 16.3 | 10.7 | 5.6 | 0.319 |
| | ZM__M50973 | $BC_1$ | 32.0 | 7.3 | 24.3 | 0.025 |
| | ZM__M50974 | $BC_1$ | 25.0 | 5.3 | 19.8 | 0.014 |
| | ZM__M50980 | $BC_1$ | 18.0 | 5.3 | 12.5 | 0.001 |
| | ZM__M50984 | $BC_1$ | 29.3 | 10.3 | 19.1 | 0.002 |
| | ZM__M50985 | $BC_1$ | 15.7 | 6.3 | 9.5 | 0.278 |
| | ZM__M51011 | $BC_1$ | 15.0 | 7.3 | 7.7 | 0.191 |
| pMON92870 | ZM__M102252 | $BC_1S_1$ | 22.5 | 0.0 | 22.5 | <0.001 |
| | ZM__M103304 | $BC_1S_1$ | 18.8 | 0.0 | 18.8 | <0.001 |
| | ZM__M103315 | $BC_1S_1$ | 30.6 | 0.0 | 30.6 | <0.001 |
| | ZM__M103316 | $BC_1S_1$ | 2.6 | 0.0 | 2.6 | 0.55 |
| | ZM__M103320 | $BC_1S_1$ | 30.0 | 0.0 | 30.0 | <0.001 |

[a]Leaf asparagine was determined in two separate experiments for pMON79706 and pMON92870.
[b]Relative free asparagine measured as a percentage of total free amino acids in leaf tissue

TABLE 3

Grain protein content in inbred maize transformed with maize AsnS2 gene (pMON79706) or maize AsnS3 gene (pMON92870).

| Construct[a] | Event | Generation | Mean of Transgene-positive Plants[a] | Mean of Transgene-negative Plants | Difference | p value |
|---|---|---|---|---|---|---|
| pMON79706 | ZM__M50965 | $BC_1$ | nd[c] | nd | nd | nd |
| | ZM__M50973 | $BC_1$ | 15.1 | 11.6 | 3.5 | 0.024 |
| | ZM__M50974 | $BC_1$ | nd | nd | nd | nd |
| | ZM__M50980 | $BC_1$ | 13.8 | 12.0 | 1.8 | 0.118 |
| | ZM__M50984 | $BC_1$ | 15.1 | 11.4 | 3.7 | 0.002 |
| | ZM__M50985 | $BC_1$ | 13.9 | 10.8 | 3.1 | 0.003 |
| | ZM__M51011 | $BC_1$ | 13.5 | 11.4 | 2.2 | 0.08 |
| pMON92870 | ZM__M102252 | $BC_1S_1$ | 13.3 | 11.9 | 1.4 | 0.096 |
| | ZM__M103304 | $BC_1S_1$ | 13.7 | 11.9 | 1.8 | 0.042 |
| | ZM__M103315 | $BC_1S_1$ | nd | 11.9 | nd | nd |
| | ZM__M103316 | $BC_1S_1$ | 11.2 | 11.9 | -0.7 | 0.373 |
| | ZM__M103320 | $BC_1S_1$ | 14.2 | 11.9 | 2.3 | 0.003 |

[a]Grain protein was determined in two separate experiments for pMON79706 and pMON92870.
[b]Grain protein measured as a percentage of total grain composition on a 0% moisture basis.
[c]nd; not determined.

The high asparagine and grain protein phenotype pMON79706 was confirmed in multiple tissues in a second trial. After the $BC_1$ generation, five events of pMON79706 were self-pollinated in two following nurseries to generate $BC_1S_3$ seed that was homozygous for the transgene. The relative concentration of asparagine resulting from expression of the pMON79706 construct was determined in a study at the corn V8 growth stage by comparing homozygous $BC_1S_3$ plants and a LH59 corn variety control (Table 4). Transgenic entries and controls were planted in a randomized complete block design with 5 replicated blocks in a field plot. The upper fully expanded leaves and stem sections of two plants were sampled and pooled, placed on dry ice, ground, lyophilized, and measured for free amino acid content by HPLC. Values followed by "*" indicate a significant difference from the LH59 control (Dunnett's one-tail test; (SAS 9.1, Cary, N.C.). Asparagine measurements taken at both the V8 growth stage and the $R_1$ generation showed that plants from five pMON79706 events had significant increases in protein analysis, 10 ears were sampled per plot, shelled, and analyzed for grain protein concentration. Grain protein was also increased significantly in the five events of pMON79706 (Table 4). The results show that, as a general trend, events producing a significant increase in asparagine also produced as significant increase in kernel protein (Tables 2-4).

TABLE 4

Relative asparagine concentrations at V8 growth stage and grain protein concentration at maturity in $BC_1S_3$ corn plants transformed with the corn AsnS2 gene (pMON79706).

| | Leaf | | Stem | | Grain |
|---|---|---|---|---|---|
| Event | Asn % Mean | Asn (ppm) Mean | Asn % Mean | Asn (ppm) Mean | Protein % Mean |
| LH59 control | 3.54 | 389 | 9.6 | 2254 | 12.3 |
| ZM__M50974 | 12.31* | 1312* | 32.20* | 9179* | 14.8* |
| ZM__M50980 | 10.20* | 1058* | 38.68* | 12844* | 15.2* |

TABLE 4-continued

Relative asparagine concentrations at V8 growth stage and grain protein concentration at maturity in $BC_1S_3$ corn plants transformed with the corn AsnS2 gene (pMON79706).

| Event | Leaf | | Stem | | Grain |
|---|---|---|---|---|---|
| | Asn % Mean | Asn (ppm) Mean | Asn % Mean | Asn (ppm) Mean | Protein % Mean |
| ZM_M50984 | 9.18* | 997* | 28.20* | 8062* | 14.4* |
| ZM_M50985 | 5.86* | 697 | 15.12* | 3404 | 14.5* |
| ZM_M51011 | 13.89* | 1740* | 37.05* | 11820* | 15.0* |

*Significant at p < 0.05

Significant increases in hybrid grain protein were observed for three different constructs expressing asparagine synthetase genes under the rice actin promoter. Homozygous inbred corn lines were produced from $R_0$ transgenic events of pMON79706 (corn AsnS2), pMON79700 (soy AsnS), and pMON79653 (yeast AsnS1) by first backcrossing $R_0$ events to the recurrent parent, LH59, followed by self-pollinations of transgene-positive selections in two subsequent inbred nurseries using the NPTII selectable marker to score for zygosity. The homozygous events for each construct were then used as a male pollen donor in a cross with a female inbred line to create the $F_1$ hybrid. The $F_1$ hybrid seed was planted in a multiple-location trial and transgenic events for each construct were analyzed for final grain protein and compared to the recurrent parent hybrid control following a spatial correction analysis based on grain protein in control hybrids that were planted at regular intervals throughout the field. Grain was harvested from each plot, shelled, and analyzed for protein content. Data were analyzed using a custom developed spatial method by conducting a by-location and an across location analysis. The by-location analysis is a two-step process. The first step in the analysis involved estimating the spatial autocorrelation in the field by fitting an anisotropic spherical semi-variogram model using all spatial check plots that were placed systematically in the field (every 3rd plot). The second stage of analysis involved adjusting the values of the transgenic entries for the spatial variability using the spatial autocorrelation structure estimated in the first stage of the analysis. Following the adjustment for spatial autocorrelation in each location separately, an across-location analysis was conducted where the mean value of a transgenic entry was compared to the parental control to test the statistical significance (P=0.20) of the difference between a transgene and the control mean. All five events of pMON79706 showed significant increases in grain protein in the hybrid trial, consistent with the observation that grain protein was increased in the inbred lines of transgenic events of this construct (Table 5). Two other asparagine synthetase constructs, pMON79700 (soy AsnS) and pMON79653 (yeast AsnS), also showed significant increases in grain protein levels in two of five events and two of two events, respectively.

TABLE 5

Grain protein content in hybrid maize transformed with genes for asparagine synthetase from maize (*Zea mays*), soy (*Glycine max*), and yeast (*Saccharomyces cerevisiae*)[a].

| Construct | Gene | Event | Protein Transgenic Mean | Protein Control Mean | Protein Delta | p value |
|---|---|---|---|---|---|---|
| pMON79706 | Maize AsnS2 | ZM_M50974 | 11.12 | 8.65 | 2.48 | 0.000 |
| | | ZM_M50980 | 9.17 | 8.65 | 0.53 | 0.003 |
| | | ZM_M50984 | 9.56 | 8.65 | 0.91 | 0.000 |

TABLE 5-continued

Grain protein content in hybrid maize transformed with genes for asparagine synthetase from maize (*Zea mays*), soy (*Glycine max*), and yeast (*Saccharomyces cerevisiae*)[a].

| Construct | Gene | Event | Protein Transgenic Mean | Protein Control Mean | Protein Delta | p value |
|---|---|---|---|---|---|---|
| | | ZM_M50985 | 9.71 | 8.65 | 1.07 | 0.000 |
| | | ZM_M51011 | 9.45 | 8.65 | 0.81 | 0.000 |
| pMON79700 | Soy AsnS | ZM_M49436 | 8.52 | 8.65 | −0.13 | 0.469 |
| | | ZM_M61615 | 11.25 | 8.65 | 2.61 | 0.000 |
| | | ZM_M62422 | 13.30 | 8.65 | 4.65 | 0.000 |
| | | ZM_M62428 | 8.61 | 8.65 | −0.04 | 0.826 |
| | | ZM_M64520 | 8.76 | 8.65 | 0.11 | 0.570 |
| pMON79653 | Yeast AsnS1 | ZM_M49883 | 9.12 | 8.65 | 0.48 | 0.007 |
| | | ZM_M65281 | 9.43 | 8.65 | 0.79 | 0.000 |

[a]Grain protein measured as a percentage of total grain composition on a 0% moisture basis.

Example 6

Field Evaluation of the Transgene Expression and Asparagine Synthetase Enzyme Activity Due to pMON79706 and pMON92870

Figure 6:
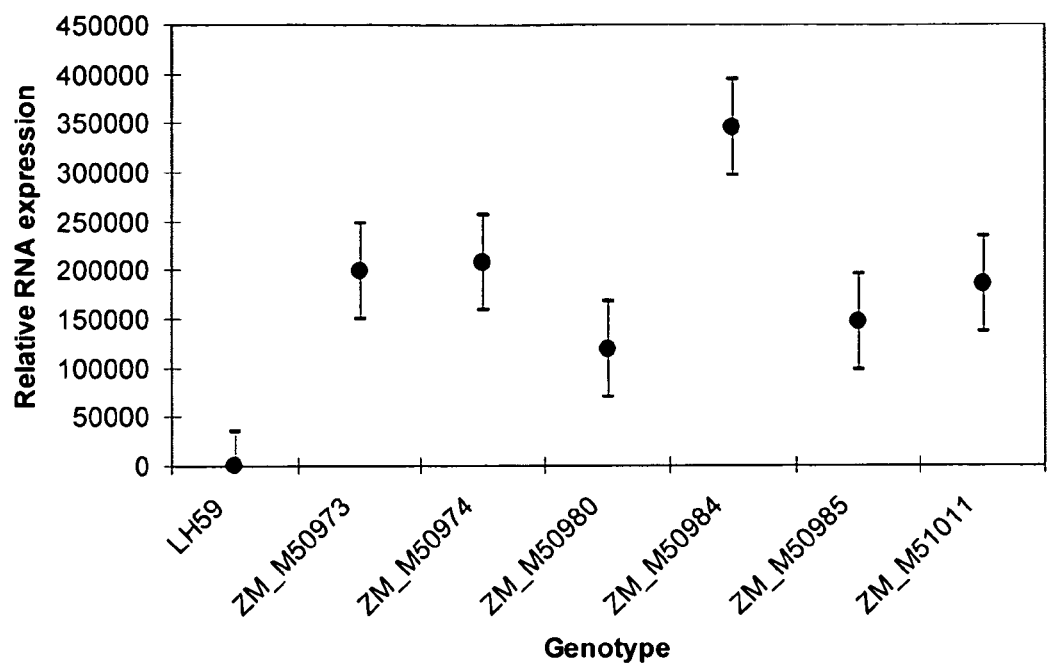
FIG. 6 Transgene expression in pMON79706 events. Error bars represent 95% confidence interval, with n=5 for transgenic events and n=10 for inbred control.

Transgene expression was confirmed in transgenic events of pMON79706 and pMON92870. For pMON79706, tissue used for the determination of leaf asparagine content in the field trial with $BC_1S_3$ homozygous inbred lines was also used for determination of transgene expression based on measurement of the expression from the 3'-terminator sequence (St.Pis4) from pMON79706 at anthesis. Two leaf samples were harvested and pooled from each of 5 replicate plots (10 for inbred control) and frozen on dry ice. Leaf samples were then ground frozen for expression analysis. For RNA extraction, 50 mg of frozen tissue were aliquoted into 96-well plates. Each sample was extracted with 500 μl of lysis buffer containing a 1:1 solution of ABI nucleic acid lysis solution (Applied Biosystems, Foster City, Calif.) to 1×PBS ph7.4 (without MgCl or CaCl). RNA was extracted from fresh-frozen tissue samples using filter-plates to capture nucleic acids from crude lysates, and 50 μl of ABI elution buffer was used to elute bound RNA. Quantitative PCR was performed using a 5 μl RNA template with 5 μl ABI one-step RT-PCR reagent. The reactions were carried out for 40 PCR cycles on an ABI Taqman 7900 PCR instrument, with cycling parameters of 48° C. for 30 min., 95° C. for 10 min., 95° C. for 10 sec., 60° C. for 1 min. Fluorescent measurements were taken from each well at each of the 40 cycles for both the terminator sequence derived from the potato protease inhibitor II (St.Pis4) and the endogenous control (ubiquitin). A subset of samples was run without reverse transcriptase to monitor DNA contamination. Samples were scored for relative expression by subtracting the cycle threshold values for St.Pis4 from the cycle threshold value of the endogenous control. The cycle threshold (Ct) was determined, and the delta Ct was calculated from the St.Pis4 minus endogenous control value. An in situ wild-type was created by calculating the average endogenous control signals and setting the St.Pis4 signal value at 40. The delta Ct of the unknown samples was subtracted from the delta Ct of the in situ wild-type. Final data was reported as pinII (St.Pis4) expression relative to wild type. Quantitative RT-PCR analysis confirmed overexpression of the transgene from six of six events of pMON79706 (FIG. 6).

Transgene expression was also confirmed in inbred events comprising pMON92870. RNA expression was determined from leaf tissue at anthesis of inbred plants grown in a field nursery by first harvesting an upper expanded leaf from each plant (4-8 plants per event) and freezing on dry ice. Transgene-positive plants were previously identified based on presence of the NPTII marker gene. Leaf tissue was ground while frozen, and analyzed for expression from the 3'-terminator sequence (St.Pis4) of pMON92870. Quantitative RT-PCR analysis showed that five of six events comprising pMON92870 showed increased transgene expression as compared to an inbred control (FIG. 7). The low RNA expression in pMON92870 event ZM_M103316 is consistent with the low leaf asparagine content and grain protein content in this event.

The effect of expression of asparagine synthetase genes on asparagine synthetase activity was measured in transgenic events of pMON79706 and pMON92870. Frozen, ground leaf tissue was aliquoted (200-400 mg) into wells from a precooled 96 deep-well plate. Protein was extracted in Buffer A (100 mM Hepes-OH, pH 8.0, 0.1 mM EDTA, 10 mM $MgCl_2$, 2 mM aspartate, 0.5 mM DTT, 67 mM mercaptoethanol, 20% (v/v) glycerol, 0.1 mM ATP, 1% (v/v) P9599 (Sigma Company), 25 mM KCl). A small amount of sand was added to each well. Buffer A was then added to the leaf tissue in the wells at a ratio of 4:1 (buffer:tissue). The plates were then agitated in a paint shaker for 2 min. to mix the sample and then centrifuged at 5000×g for 10 minutes. The supernatant (100-200 μL) was desalted in a 96-well macro spin plate (SNS S025L, The Nest Group Inc., Southboro, Mass.) equilibrated in buffer A. The supernatant was then either assayed immediately or frozen in liquid nitrogen and maintained at −80° C. until used. To assay asparagine synthetase activity, desalted protein extracts (10-50 μL) were added to wells containing 100 μL assay solution (100 mM Hepes, pH 8.0, 10 mM $MgCl_2$, 2 mM aspartate, 5 mM DTT, 10 mM ATP, 1 mM amino(oxy)acetic acid (aspartate amino transferase inhibitor), 1 mM aspartic semialdehyde (asparaginase inhibitor). To start the reaction, glutamine (final concentration of 2 mM for standard assay) was added to the solution, which was then mixed. The assay mixture was then incubated for 1 to 2 hours. The reaction was then stopped by the addition of an equal volume of 20% (w/v) trichloroacetic acid. The mixture was then filtered to remove precipitate and asparagine was measured by HPLC. Sample size was increased from 0.5 μL to 2.5 μL for HPLC, excitation wavelength was reduced from 340 nm to 235 nm, and fluorimeter gain was increased from 10 to 13. This results in a sensitivity of detection of 0.5 to 100 μM asparagine and allows the measurement of levels of activity in the 100s of microunits.

For pMON79706, tissue used for the determination of leaf asparagine synthetase enzyme activity was from a field trial with $BC_1S_3$ homozygous inbred lines harvested at the V7 growth stage. Events of pMON79706 were shown to display increased leaf asparagine synthetase activity (Table 6). Asparagine synthetase activity was increased up to 5-fold over the inbred variety control. Asparagine synthetase enzyme activity was also determined for transgenic events of pMON92870 in an inbred field nursery at the time of anthesis. Four of five pMON92870 events also showed increased enzyme activity (Table 6). The increased asparagine synthetase enzyme activity in corn plants expressing the corn AsnS2 (pMON79706) or corn AsnS3 (pMON92870) under the rice actin promoter is consistent with the increase in gene expression and leaf asparagine increases observed with these constructs.

TABLE 6

Asparagine synthetase activity in inbred lines of transgenic events of pMON79706 and pMON92870[a].

| Construct | Event | AsnS Activity (μunits/mg protein) |
|---|---|---|
| Control | LH59 | 276 |
| pMON79706 | ZM_M50973 | 519 |
| | ZM_M50974 | 1179 |
| | ZM_M50984 | 1592 |
| | ZM_M50985 | 450 |
| | ZM_M51011 | 1031 |
| Control | LH244 | 98 |
| pMON92870 | ZM_M102252 | 160 |
| | ZM_M103304 | 209 |
| | ZM_M103315 | 243 |
| | ZM_M103316 | 11 |
| | ZM_M103319 | 192 |
| | ZM_M103320 | 240 |

[a]Enzyme activities for pMON79706 and pMON92870 were determined from two different field experiments.

Example 7

Field Evaluation of the Effects of pMON66231, pMON66239, and pMON74946 on Asparagine and Grain Protein Content The relative content of free asparagine in corn tissues was obtained from hybrid lines derived from $R_0$ corn plants (LH244 background) transformed with pMON66231 (FIG. 4), where corn AsnS2 is under the control of the corn FDA promoter. Hybrids were made by crossing the $R_0$ plants to the male inbred line LH59, which creates a segregating (1:1) $F_1$ population. The resulting $F_1$ seed was planted in three midwest location with two replications at each location. Plots were sprayed with glyphosate at V3 growth stage to eliminate null segregants. A hybrid control was planted in the perimeter and comparisons were made to the hybrid control. Upper leaves were collected and pooled from three plants within each plot at the time of anthesis, two hours after sunset, at all three locations. Leaves were placed immediately on dry ice and then stored at −80° C. until processing. Leaves were ground frozen, and a portion was lyophilized for free amino acid analysis by HPLC. Data were first screened for outliers with the two-pass method for deleted studentized residuals using Bonferroni-adjusted p-values. Outliers were identified and removed from the data set before analysis of variance calculations were initiated. The data were analyzed according to an across-locations randomized complete block design. Construct-event combinations were modeled with fixed effects, and locations and reps within locations were modeled with random effects. Treatment comparisons were made by performing contrasts of the least-squares means of the construct-event combinations. Relative leaf asparagine was increased significantly in 11 of 12 events of pMON66231, with asparagine levels as high as 16% as compared to 3% in the control (Table 7). Mature grain protein was also measured following harvest of 10 ears per plot followed by shelling and pooling of seed for each plot, which was then measured for grain protein content. Nine of 12 events were found to significantly increase protein content in the mature grain over the LH244/LH59 hybrid control.

TABLE 7

Relative leaf asparagine and mature grain protein content in pMON66231 transgenic events.

| Event | Leaf Asn %[a] Mean | p value[b] | Grain Protein % Mean | p value[b] |
|---|---|---|---|---|
| LH244/LH59 | 2.73 | | 8.68 | |
| ZM_S120303 | 11.41 | <.001 | 8.57 | 0.774 |
| ZM_S120316 | 8.92 | 0.007 | 9.90 | 0.002 |
| ZM_S122246 | 8.69 | 0.01 | 10.22 | <.001 |
| ZM_S122249 | 9.85 | 0.002 | 10.83 | <.001 |
| ZM_S122257 | 9.57 | 0.003 | 12.48 | <.001 |
| ZM_S122262 | 10.10 | 0.001 | 9.70 | 0.011 |
| ZM_S122267 | 9.33 | 0.004 | 9.23 | 0.162 |
| ZM_S122279 | 12.67 | <.001 | 11.13 | <.001 |
| ZM_S122280 | 12.54 | <.001 | 10.90 | <.001 |
| ZM_S122281 | 9.47 | 0.003 | 10.53 | <.001 |
| ZM_S122291 | 16.25 | <.001 | 9.83 | 0.004 |
| ZM_S122303 | 6.44 | 0.126 | 8.53 | 0.71 |

[a]Relative free asparagine measured as a percentage of total free amino acids in leaf tissue
[b]Compared to hybrid control.

The relative content of free asparagine in corn tissues was obtained from hybrid lines derived from $R_0$ corn plants (LH244 background) transformed with pMON66239 and pMON74946, where corn AsnS2 is under the control of the RTBV or e35S promoter, respectively. Hybrids were made by crossing the $R_0$ plants to the male inbred line, LH59, which creates a segregating (1:1) $F_1$ population. The resulting $F_1$ seed was planted in one location in Hawaii with three replications for each transgenic event. Plots were sprayed with glyphosate at V3 growth stage to eliminate null segregants. A hybrid control lacking the corn AsnS2 gene was included for comparison. Upper leaves were collected and pooled from three plants within each plot at the time of anthesis, two hours after sunset. Leaves were placed immediately on dry ice and then stored at −80° C. until processing. Leaves were ground frozen, and a portion was lyophilized for free amino acid analysis by HPLC. Data were first screened for outliers with the two-pass method for deleted studentized residuals using Bonferroni-adjusted p-values. Outliers were identified and removed from the data set before analysis of variance calculations were initiated. The data were analyzed according to a randomized complete block design. Construct-event combinations were modeled with fixed effects, and reps were modeled with random effects. Treatment comparisons were made by performing contrasts of the least-squares means of the construct-event combinations. Relative leaf asparagine was increased significantly in 10 of 13 events of pMON74946, with asparagine levels as high as 16% as compared to 2% in the control (Table 8). Mature grain protein was also measured following harvest of all ears per plot followed by shelling and pooling of seed for each plot, which was then measured for grain protein content and analyzed statistically as for the leaf asparagine trait. Ten of thirteen events were found to possess significantly increased protein content in the mature grain as compared to the hybrid control, and the same 10 events with increased leaf asparagine also showed increased protein in the hybrid trial. For transgenic events of pMON66239, 11 of 15 events showed increases in leaf asparagine content, and 3 of 15 events showed significant increases in grain protein at the 0.05 alpha level, although an additional five transgenic events showed increased protein at p<0.15, indicating that expression of corn AsnS2 under the RTBV promoter (pMON66239) can increase leaf asparagine content and kernel protein content, but to a lesser extent than under the e35s promoter (pMON74946) (Table 8).

TABLE 8

Relative leaf asparagine and mature grain protein content in pMON74946 and pMON66239 transgenic events.

| Construct | Event | Leaf Asn %[a] Mean | p value[b] | Grain Protein % Mean | p value[b] |
|---|---|---|---|---|---|
| Control | Hybrid control | 1.47 | | 7.98 | |
| pMON74946 | ZM_S156600 | 10.37 | <.0001 | 8.67 | 0.0398 |
| | ZM_S156602 | 1.23 | 0.7315 | 8.43 | 0.1728 |
| | ZM_S156606 | 0.39 | 0.1214 | 7.43 | 0.0995 |
| | ZM_S156613 | 0.71 | 0.2786 | 7.70 | 0.3959 |
| | ZM_S156634 | 14.79 | <.0001 | 9.37 | <.0001 |
| | ZM_S156636 | 12.28 | <.0001 | 9.23 | 0.0002 |
| | ZM_S160005 | 15.57 | <.0001 | 9.50 | <.0001 |
| | ZM_S160015 | 15.85 | <.0001 | 13.10 | <.0001 |
| | ZM_S160025 | 13.41 | <.0001 | 9.13 | 0.0007 |
| | ZM_S160026 | 11.94 | <.0001 | 9.17 | 0.0005 |
| | ZM_S160034 | 11.00 | <.0001 | 9.60 | <.0001 |
| | ZM_S160037 | 15.79 | <.0001 | 9.10 | 0.001 |
| | ZM_S160042 | 14.73 | <.0001 | 9.17 | 0.0005 |
| pMON66239 | ZM_S140597 | 8.84 | <.0001 | 11.03 | <.0001 |
| | ZM_S140601 | 2.14 | 0.3419 | 8.20 | 0.5078 |
| | ZM_S140609 | 10.08 | <.0001 | 8.50 | 0.1182 |
| | ZM_S140613 | 2.67 | 0.0881 | 8.50 | 0.1182 |
| | ZM_S140615 | 1.23 | 0.7333 | 8.20 | 0.5078 |
| | ZM_S140617 | 6.68 | <.0001 | 8.50 | 0.1182 |
| | ZM_S140618 | 3.93 | 0.0005 | 8.73 | 0.0244 |
| | ZM_S140633 | 5.96 | <.0001 | 8.63 | 0.0503 |
| | ZM_S140635 | 3.69 | 0.0017 | 8.37 | 0.2445 |
| | ZM_S140645 | 5.88 | <.0001 | 8.37 | 0.2445 |
| | ZM_S140647 | 3.66 | 0.0019 | 8.30 | 0.3353 |
| | ZM_S140651 | 4.66 | <.0001 | 8.57 | 0.0784 |
| | ZM_S140661 | 4.13 | 0.0002 | 8.03 | 0.8741 |
| | ZM_S140663 | 2.07 | 0.61 | 9.03 | 0.0018 |
| | ZM_S140665 | 7.33 | <.0001 | 8.27 | 0.388 |

[a]Relative free asparagine measured as a percentage of total free amino acids in leaf tissue
[b]Compared to hybrid control.

All publications, patents and patent applications are herein incorporated by reference to the same extent as if each individual publication or patent application was specifically and individually indicated to be incorporated by reference.

The function of polypeptides of the present invention is determined by comparison of the amino acid sequence of the novel polypeptides to amino acid sequences of known polypeptides. A variety of homology based search algorithms are available to compare a query sequence to a protein database, including for example, BLAST, FASTA, and Smith-Waterman. In the present application, BLASTX and BLASTP algorithms are used to provide protein function information. A number of values are examined in order to assess the confidence of the function assignment. Useful measurements include "E-value" (also shown as "hit_p"), "percent identity", "percent query coverage", and "percent hit coverage".

In BLAST, E-value, or expectation value, represents the number of different alignments with scores equivalent to or better than the raw alignment score, S, that are expected to occur in a database search by chance. The lower the E value, the more significant the match. Because database size is an element in E-value calculations, E-values obtained by BLASTing against public databases, such as GenBank, have generally increased over time for any given query/entry match. In setting criteria for confidence of polypeptide function prediction, a "high" BLAST match is considered herein as having an E-value for the top BLAST hit provided in Table 9 of less than 1E-30; a medium BLASTX E-value is 1E-30 to 1E-8; and a low BLASTX E-value is greater than 1E-8. The top BLAST hit and corresponding E values are provided in columns six and seven of Table 9.

Percent identity refers to the percentage of identically matched amino acid residues that exist along the length of that portion of the sequences which is aligned by the BLAST algorithm. In setting criteria for confidence of polypeptide function prediction, a "high" BLAST match is considered herein as having percent identity for the top BLAST hit provided in Table 9 of at least 70%; a medium percent identity value is 35% to 70%; and a low percent identity is less than 35%.

Of particular interest in protein function assignment in the present invention is the use of combinations of E-values, percent identity, query coverage and hit coverage. Query coverage refers to the percent of the query sequence that is represented in the BLAST alignment. Hit coverage refers to the percent of the database entry that is represented in the BLAST alignment. In the present invention, function of a query polypeptide is inferred from function of a protein homolog where either (1) hit_p<1e-30 or % identity>35% AND query_coverage>50% AND hit_coverage>50%, or (2) hit_p<1e-8 AND query_coverage>70% AND hit_coverage>70%.

The open reading frame in each polynucleotide sequence is identified by a combination of predictive and homology based methods. The longest open reading frame (ORF) is determined, and the top BLAST match is identified by BLASTX against NCBI. The top BLAST hit is then compared to the predicted ORF, with the BLAST hit given precedence in the case of discrepancies.

Functions of polypeptides encoded by the polynucleotide sequences of the present invention are determined using a hierarchical classification tool, termed FunCAT, for Functional Categories Annotation Tool. Most categories collected in FunCAT are classified by function, to although other criteria are used, for example, cellular localization or temporal process. The assignment of a functional category to a query sequence is based on BLASTX sequence search results, which compare two protein sequences. FunCAT assigns categories by iteratively scanning through all blast hits, starting with the most significant match, and reporting the first category assignment for each FunCAT source classification scheme. In the present invention, function of a query polypeptide is inferred from the function of a protein homolog where either (1) hit_p<1e-30 or % identity >35% AND query_coverage >50% AND hit_coverage >50%, or (2) hit_p<1e-8 AND query_coverage >70% AND hit_coverage>70%.

Functional assignments from five public classification schemes, GO_BP, GO_CC, GO_MF, KEGG, and EC, and one internal Monsanto classification scheme, POT, are provided in Table 9. The column under the heading "CAT_TYPE" indicates the source of the classification. GO_BP=Gene Ontology Consortium—biological process; GO_CC=Gene Ontology Consortium—cellular component; GO_MF=Gene Ontology Consortium—molecular function; KEGG=KEGG functional hierarchy; EC=Enzyme Classification from ENZYME data bank release 25.0; POI=Pathways of Interest. The column under the heading "CAT_DESC" provides the name of the subcategory into which the query sequence was classified. The column under the heading "PRODUCT_HIT_DESC" provides a description of the BLAST hit to the query sequences that led to the specific classification. The column under the heading "HIT_E" provides the e-value for the BLAST hit. It is noted that the c-value in the HIT_E column may differ from the e-value based on the top BLAST hit provided in the E-VALUE column since these calculations were done on different days, and database size is an element in E-value calculations. E-values obtained by BLASTing against public databases, such as GenBank, will generally increase over time for any given query/entry match.

Table 9 Column Descriptions:

SEQ_NUM provides the SEQ ID NO for the listed polynucleotide sequences.

CONTIG_ID provides an arbitrary sequence name taken from the name of the clone from which the cDNA sequence was obtained.

PROTEIN_NUM provides the SEQ ID NO for the translated polypeptide sequence

NCBI_GI provides the GenBank ID number for the top BLAST hit for the sequence. The top BLAST hit is indicated by the National Center for Biotechnology Information GenBank Identifier number.

NCBI_GI_DESCRIPTION refers to the description of the GenBank top BLAST hit for the sequence.

E_VALUE provides the expectation value for the top BLAST match.

MATCH_LENGTH provides the length of the sequence which is aligned in the top BLAST match TOP_HIT_PCT_IDENT refers to the percentage of identically matched nucleotides (or residues) that exist along the length of that portion of the sequences which is aligned in the top BLAST match.

CAT_TYPE indicates the classification scheme used to classify the sequence. GO_BP=Gene Ontology Consortium—biological process; GO_CC=Gene Ontology Consortium—cellular cellular component; GO_MF=Gene Ontology Consortium—molecular function; KEGG=KEGG functional hierarchy (KEGG=Kyoto Encyclopedia of Genes and Genomes); EC=Enzyme Classification from ENZYME data bank release 25.0; POI=Pathways of Interest.

CAT_DESC provides the classification scheme subcategory to which the query sequence was assigned.

PRODUCT_CAT_DESC provides the FunCAT annotation category to which the query sequence was assigned.

PRODUCT_HIT_DESC provides the description of the BLAST hit which resulted in assignment of the sequence to the function category provided in the cat_desc column.

HIT_E provides the E value for the BLAST hit in the hit_desc column.

PCT_IDENT refers to the percentage of identically matched nucleotides (or residues) that exist along the length of that portion of the sequences which is aligned in the BLAST match provided in hit_desc.

QRY_RANGE lists the range of the query sequence aligned with the hit.

HIT_RANGE lists the range of the hit sequence aligned with the query.

QRY_CVRG provides the percent of query sequence length that matches to the hit (NCBI) sequence in the BLAST match (% qry cvrg=(match length/query total length)×100).

HIT_CVRG provides the percent of hit sequence length that matches to the query sequence in the match generated using BLAST (% hit cvrg=(match length/hit total length)×100).

TABLE 9

| Seq_Num | Seq_ID | PROTEIN_NUM | CDNA_Coord Prt_Num | Blast_Hit_ID |
|---|---|---|---|---|
| 1. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 2. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 3. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 4. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 5. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 6. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 7. | 13515 | JC-ZMXLIB3526P040 AA08_FLI | JC-ZMXLIB3526P040 AA08__FLI.pep | 3-1811 | gi|1351989|sp|P49094|ASNS_MAIZE |
| 8. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 9. | 13515 | JC-ZMXLIB3526P040 AA08FLI | JC-ZMXLIB3526P040 AA08_FLI.pep | 3-1811 | gi|1351989|sp|P49094|ASNS_MAIZE |
| 10. | 13515 | JC-ZMXLIB3526P040 AA08__FLI | JC-ZMXLIB3526P040 AA08_FLI.pep | 3-1811 | gi|1351989|sp|P49094|ASNS_MAIZE |
| 11. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 12. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 13. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 14. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 15. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 16. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 17. | 13515 | JC-ZMXLIB3526P040 AA08_FLI | JC-ZMXLIB3526P040 AA08FLI.pep | 3-1811 | gi|1351989|sp|P49094|ASNS_MAIZE |
| 18. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 19. | 13515 | JC-ZMXLIB3526P040 AA08_FLI | JC-ZMXLIB3526P040 AA08FLI.pep | 3-1811 | gi|1351989|sp|P49094|ASNS_MAIZE |
| 20. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 21. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 22. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 23. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 24. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 25. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 26. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 27. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 28. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 29. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 30. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 31. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 32. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 33. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 34. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 35. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 36. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 37. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 38. | 13515 | JC-ZMXLIB3526P040 AA08_FLI | JC-ZMXLIB3526P040 AA08_FLI.pep | 3-1811 | gi|1351989|sp|P49094|ASNS_MAIZE |
| 39. | 13515 | JC-ZMXLIB3526P040 AA08_FLI | JC-ZMXLIB3526P040 AA08_FLI.pep | 3-1811 | gi|1351989|sp|P49094|ASNS_MAIZE |

TABLE 9-continued

| | Seq_Num | Seq_ID | PROTEIN_NUM | CDNA_Coord | Prt_Num | Blast_Hit_ID |
|---|---|---|---|---|---|---|
| 40. | 13515 | JC-ZMXLIB3526P040 AA08_FLI | JC-ZMXLIB3526P040 AA08_FLI.pep | 3-1811 | | gi|1351989|sp|P49094|ASNS_MAIZE |
| 41. | 13515 | JC-ZMXLIB3526P040 AA08_FLI | JC-ZMXLIB3526P040 AA08_,FLI.pep | 3-1811 | | gi|1351989|sp|P49094|ASNS_MAIZE |
| 42. | 13515 | JC-ZMXLIB3526P040 AA08_FLI | JC-ZMXLIB3526P040 AA08_FLI.pep | 3-1811 | | gi|1351989|sp|P49094|ASNS_MAIZE |
| 43. | 13515 | JC-ZMXLIB3526P040 AA08_FLI | JC-ZMXLIB3526P040 AA08_FLI.pep | 3-1811 | | gi|1351989|sp|P49094|ASNS_MAIZE |
| 44. | 13515 | JC-ZMXLIB3526P040 AA08_FLI | JC-ZMXLIB3526P040 AA08_FLI.pep | 3-1811 | | gi|1351989|sp|P49094|ASNS_MAIZE |
| 45. | 13515 | JC-ZMXLIB3526P040 AA08_FLI | JC-ZMXLIB3526P040 AA08_FLI.pep | 3-1811 | | gi|1351989|sp|P49094|ASNS_MAIZE |
| 46. | 13515 | JC-ZMXLIB3526P040 AA08_FLI | JC-ZMXLIB3526P040 AA08_FLI.pep | 3-1811 | | gi|1351989|sp|P49094|ASNS_MAIZE |
| 47. | 13515 | JC-ZMXLIB3526P040 AA08_FLI | JC-ZMXLIB3526P040 AA08_FLI.pep | 3-1811 | | gi|1351989|sp|P49094|ASNS_MAIZE |
| 48. | 13515 | JC-ZMXLIB3526P040 AA08_FLI | JC-ZMXLIB3526P040 AA08_FLI.pep | 3-1811 | | gi|1351989|sp|P49094|ASNS_MAIZE |
| 49. | 13515 | JC-ZMXLIB3526P040 AA08_FLI | JC-ZMXLIB3526P040 AA08_FLI.pep | 3-1811 | | gi|1351989|sp|P49094|ASNS_MAIZE |
| 50. | 13515 | JC-ZMXLIB3526P040 AA08_FLI | JC-ZMXLIB3526P040 AA08_FLI.pep | 3-1811 | | gi|1351989|sp|P49094|ASNS_MAIZE |
| 51. | 13515 | JC-ZMXLIB3526P040 AA08_FLI | JC-ZMXLIB3526P040 AA08_FLI.pep | 3-1811 | | gi|1351989|sp|P49094|ASNS_MAIZE |
| 52. | 13515 | JC-ZMXLIB3526P040 AA08_FLI | JC-ZMXLIB3526P040 AA08_FLI.pep | 3-1811 | | gi|1351989|sp|P49094|ASNS_MAIZE |
| 53. | 13515 | JC-ZMXLIB3526P040 AA08_FLI | JC-ZMXLIB3526P040 AA08_FLI.pep | 3-1811 | | gi|1351989|sp|P49094|ASNS_MAIZE |
| 54. | 13515 | JC-ZMXLIB3526P040 AA08_FLI | JC-ZMXLIB3526P040 AA08_FLI.pep | 3-1811 | | gi|1351989|sp|P49094|ASNS_MAIZE |

| | Blast_EValue | Blast_FR_ID | Blast_Des | Species | Cat_Type | Cat_Desc |
|---|---|---|---|---|---|---|
| 1. | 0.00 | 0.79 | Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] | Zea mays | POI | 5.1.3.4.16.7.17.87 |
| 2. | 0.00 | 0.79 | Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] | Zea mays | POI | 5.1.21.7.17.97 |
| 3. | 0.00 | 0.79 | Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] | Zea mays | POI | 5.1.7.17.97 |
| 4. | 0.00 | 0.79 | Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] | Zea mays | POI | 5.1.11.13.4.15.7.17.97 |
| 5. | 0.00 | 0.79 | Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] | Zea mays | POI | 5.1.11.13.4.16.7.17.97 |

-continued

| | Blast_EValue | Blast_FR_ID | Blast_Des | Species | Cat_Type | Cat_Desc |
|---|---|---|---|---|---|---|
| 6. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.11.13.4.7.17.97 |
| 7. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.2.3.11.13.4.15.7.17.97 |
| 8. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.2.3.11.13.4.16.7.17.97 |
| 9. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.2.3.11.13.4.7.17.97 |
| 10. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.2.3.4.16.7.17.97 |
| 11. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.2.4.15.7.17.97 |
| 12. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.7.17.87 |
| 13. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.2.4.7.17.97 |
| 14. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.4.7.17.87 |
| 15. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC | Zea mays | POI | 5.1.3.11.13.4.15.7.17.97 |

| | Blast_EValue | Blast_FR_ID | Blast_Des | Species | Cat_Type | Cat_Desc |
|---|---|---|---|---|---|---|
| 16. | 0.00 | 0.79 | 6.3.5.4) - maize gi\|984262\|emb\|CAA58052.1\| asparragine synthetase [Zea mays] Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.3.11.13.4.16.7.17.97 |
| 17. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.3.11.13.4.7.17.97 |
| 18. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.3.4.15.7.17.97 |
| 19. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.3.4.16.7.17.97 |
| 20. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.3.4.7.17.97 |
| 21. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.4.15.7.17.97 |
| 22. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.4.16.7.17.97 |
| 23. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.4.7.17.97 |
| 24. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.2.4.16.7.17.97 |
| 25. | 0.00 | 0.79 | Asparagine synthetase [glutamine-hydrolyzing] (Glutamine-dependent | Zea mays | POI | 5.1.2.4.15.7.17.87 |

-continued

| | Blast_EValue | Blast_FR_ID | Blast_Des | Species | Cat_Type | Cat_Desc |
|---|---|---|---|---|---|---|
| | | | asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | | | |
| 26. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.4.15.7.17.87 |
| 27. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | EC | 6.3.5.4 |
| 28. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.11.13.4.15.7.17.87 |
| 29. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.11.13.4.16.7.17.87 |
| 30. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.11.13.4.7.17.87 |
| 31. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.2.3.11.13.4.15.7.17.87 |
| 32. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.2.3.11.13.4.16.7.17.87 |
| 33. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.2.3.11.13.4.7.17.87 |
| 34. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC | Zea mays | POI | 5.1.2.3.4.15.7.17.87 |

| | Blast_EValue | Blast_FR_ID | Blast_Des | Species | Cat_Type | Cat_Desc |
|---|---|---|---|---|---|---|
| 35. | 0.00 | 0.79 | 6.3.5.4) - maize gi\|984262\|emb\|CAA58052.1\| asparragine synthetase [Zea mays] Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 3.7.110.579 |
| 36. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.2.3.4.7.17.87 |
| 37. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.2.3.4.7.17.97 |
| 38. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.2.4.16.7.17.87 |
| 39. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.2.4.7.17.87 |
| 40. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.21.7.17.87 |
| 41. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.3.11.13.4.15.7.17.87 |
| 42. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.3.11.13.4.16.7.17.87 |
| 43. | 0.00 | 0.79 | Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | POI | 5.1.3.11.13.4.7.17.87 |
| 44. | 0.00 | 0.79 | Asparagine synthetase [glutamine-hydrolyzing] (Glutamine-dependent | Zea mays | POI | 5.1.3.4.15.7.17.87 |

-continued

| | Blast_EValue | Blast_FR_ID | Blast_Des | Species | Cat_Type | Cat_Desc |
|---|---|---|---|---|---|---|
| | | | asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] | | | |
| 45. | 0.00 | 0.79 | Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] | Zea mays | POI | 5.1.3.4.7.17.87 |
| 46. | 0.00 | 0.79 | Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] | Zea mays | POI | 5.1.4.16.7.17.87 |
| 47. | 0.00 | 0.79 | Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] | Zea mays | POI | 5.1.2.3.4.16.7.17.87 |
| 48. | 0.00 | 0.79 | Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] | Zea mays | POI | 5.1.2.3.4.15.7.17.97 |
| 49. | 0.00 | 0.79 | Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] | Zea mays | KEGG | 2.5 |
| 50. | 0.00 | 0.79 | Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] | Zea mays | MIPS EC | 3.2.1.3 |
| 51. | 0.00 | 0.79 | Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] | Zea mays | KEGG | 7.1 |
| 52. | 0.00 | 0.79 | Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] | Zea mays | MIPS_EC | 6.3.5.4 |
| 53. | 0.00 | 0.79 | Asparagine synthetase [glutamine-hydrolyzing] (Glutamine-dependent asparagine synthetase) gi|7438077|pir||T02978 asparagine synthase (glutamine-hydrolysing) (EC | Zea mays | KEGG | 5.2 |

| | Blast_EValue | Blast_FR_ID | Blast_Des | Species | Cat_Type | Cat_Desc |
|---|---|---|---|---|---|---|
| 54. | 0.00 | 0.79 | 6.3.5.4) - maize gi\|984262\|emb\|CAA58052.1\| asparragine synthetase [Zea mays] Asparagine synthetase [glutamine-hydrolyzing] (Glutamine-dependent asparagine synthetase) gi\|7438077\|pir\|\|T02978 asparagine synthase (glutamine-hydrolysing) (EC 6.3.5.4) - maize gi\|984262\|emb\|CAA58052.1\| asparragine synthetase [Zea mays] | Zea mays | EC | 3.2.1.3 |

| | Prod_Cat_Desc |
|---|---|
| 1. | |
| 2. | |
| 3. | |
| 4. | |
| 5. | |
| 6. | |
| 7. | |
| 8. | |
| 9. | |
| 10. | |
| 11. | |
| 12. | |
| 13. | |
| 14. | |
| 15. | |
| 16. | |
| 17. | |
| 18. | |
| 19. | |
| 20. | |
| 21. | |
| 22. | |
| 23. | |
| 24. | |
| 25. | |
| 26. | |
| 27. | Ligases\Forming carbon-nitrogen bonds\Carbon--nitrogen ligases with glutamine as amido-N-donor\Asparagine synthase (glutamine-hydrolysing) |
| 28. | |
| 29. | |
| 30. | |
| 31. | |
| 32. | |
| 33. | |
| 34. | |
| 35. | Monsanto Patent Pathways\Yield\Glutamate and Glutamine Family Synthesis/Degradation\Asparagine synthase |
| 36. | |
| 37. | |
| 38. | |
| 39. | |
| 40. | |
| 41. | |
| 42. | |
| 43. | |
| 44. | |
| 45. | |
| 46. | |
| 47. | |
| 48. | |
| 49. | Energy Metabolism\Nitrogen metabolism [MAP:00910] |
| 50. | Hydrolases. 3.-.-.- Hydrolases.\Glycosidases. 3.2.-.- Glycosidases.\ Hydrolysing O-glycosyl compounds. 3.2.1.- Hydrolysing O-glycosyl compounds.\Glucan 1,4-alpha-glucosidase.3.2.1.3 Glucan 1,4-alpha-glucosidase. |
| 51. | Metabolism of Complex Carbohydrates\Starch and sucrose metabolism [MAP:00500] |
| 52. | Ligases. 6.-.-.- Ligases.\Forming carbon-nitrogen bonds. 6.3.-.- Forming carbon-nitrogen bonds.\Carbon--nitrogen ligases with glutamine as amido-N-donor. 6.3.5.- Carbon--nitrogen ligases with glutamine as amido-N-donor.\Asparagine synthase (glutamine-hydrolysing).6.3.5.4 Asparagine synthase (glutamine-hydrolysing). |
| 53. | Amino Acid Metabolism\Alanine and aspartate metabolism [MAP:00252] |
| 54. | Hydrolases\Glycosylases\Glycosidases - hydrolysing O-glycosyl compounds\Glucan 1,4-alpha-glucosidase |

| | FunCat_S_Beg | FunCat_S_End | FunCat_Strand | FunCat_E-Value | FunCat_Hit_ID |
|---|---|---|---|---|---|
| 1. | 1.00 | 586.00 | + | 0.00 | g1351989 |
| 2. | 1.00 | 544.00 | + | 0.00 | g3821280 |
| 3. | 1.00 | 544.00 | + | 0.00 | g3821280 |
| 4. | 1.00 | 544.00 | + | 0.00 | g3821280 |
| 5. | 1.00 | 544.00 | + | 0.00 | g3821280 |
| 6. | 1.00 | 544.00 | + | 0.00 | g3821280 |
| 7. | 1.00 | 544.00 | + | 0.00 | g3821280 |
| 8. | 1.00 | 544.00 | + | 0.00 | g3821280 |
| 9. | 1.00 | 544.00 | + | 0.00 | g3821280 |
| 10. | 1.00 | 544.00 | + | 0.00 | g3821280 |
| 11. | 1.00 | 544.00 | + | 0.00 | g3821280 |
| 12. | 1.00 | 586.00 | + | 0.00 | g1351989 |
| 13. | 1.00 | 544.00 | + | 0.00 | g3821280 |
| 14. | 1.00 | 586.00 | + | 0.00 | g1351989 |
| 15. | 1.00 | 544.00 | + | 0.00 | g3821280 |
| 16. | 1.00 | 544.00 | + | 0.00 | g3821280 |
| 17. | 1.00 | 544.00 | + | 0.00 | g3821280 |
| 18. | 1.00 | 544.00 | + | 0.00 | g3821280 |
| 19. | 1.00 | 544.00 | + | 0.00 | g3821280 |
| 20. | 1.00 | 544.00 | + | 0.00 | g3821280 |

-continued

| | FunCat_S_Beg | FunCat_S_End | FunCat_Strand | FunCat_E-Value | FunCat_Hit_ID |
|---|---|---|---|---|---|
| 21. | 1.00 | 544.00 | + | 0.00 | g3821280 |
| 22. | 1.00 | 544.00 | + | 0.00 | g3821280 |
| 23. | 1.00 | 544.00 | + | 0.00 | g3821280 |
| 24. | 1.00 | 544.00 | + | 0.00 | g3821280 |
| 25. | 1.00 | 586.00 | + | 0.00 | g1351989 |
| 26. | 1.00 | 586.00 | + | 0.00 | g1351989 |
| 27. | 1.00 | 586.00 | + | 0.00 | g1351989 |
| 28. | 1.00 | 586.00 | + | 0.00 | g1351989 |
| 29. | 1.00 | 586.00 | + | 0.00 | g1351989 |
| 30. | 1.00 | 586.00 | + | 0.00 | g1351989 |
| 31. | 1.00 | 586.00 | + | 0.00 | g1351989 |
| 32. | 1.00 | 586.00 | + | 0.00 | g1351989 |
| 33. | 1.00 | 586.00 | + | 0.00 | g1351989 |
| 34. | 1.00 | 586.00 | + | 0.00 | g1351989 |
| 35. | 1.00 | 553.00 | + | 0.00 | g399064 |
| 36. | 1.00 | 586.00 | + | 0.00 | g1351989 |
| 37. | 1.00 | 544.00 | + | 0.00 | g3821280 |
| 38. | 1.00 | 586.00 | + | 0.00 | g1351989 |
| 39. | 1.00 | 586.00 | + | 0.00 | g1351989 |
| 40. | 1.00 | 586.00 | + | 0.00 | g1351989 |
| 41. | 1.00 | 586.00 | + | 0.00 | g1351989 |
| 42. | 1.00 | 586.00 | + | 0.00 | g1351989 |
| 43. | 1.00 | 586.00 | + | 0.00 | g1351989 |
| 44. | 1.00 | 586.00 | + | 0.00 | g1351989 |
| 45. | 1.00 | 586.00 | + | 0.00 | g1351989 |
| 46. | 1.00 | 586.00 | + | 0.00 | g1351989 |
| 47. | 1.00 | 586.00 | + | 0.00 | g1351989 |
| 48. | 1.00 | 544.00 | + | 0.00 | g3821280 |
| 49. | 1.00 | 568.00 | + | 1.0e−149 | g6325403 |
| 50. | 201.00 | 1226.00 | + | 3.0e−28 | g6322209 |
| 51. | 201.00 | 1226.00 | + | 3.0e−28 | g6322209 |
| 52. | 1.00 | 568.00 | + | 1.0e−149 | g6325403 |
| 53. | 1.00 | 568.00 | + | 1.0e−149 | g6325403 |
| 54. | 201.00 | 1226.00 | + | 3.0e−28 | g6322209 |

FunCat Hit_Desc

1. Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays]
2. asparagine synthetase type II [Phaseolus vulgaris]
3. asparagine synthetase type II [Phaseolus vulgaris]
4. asparagine synthetase type II [Phaseolus vulgaris]
5. asparagine synthetase type II [Phaseolus vulgaris]
6. asparagine synthetase type II [Phaseolus vulgaris]
7. asparagine synthetase type II [Phaseolus vulgaris]
8. asparagine synthetase type II [Phaseolus vulgaris]
9. asparagine synthetase type II [Phaseolus vulgaris]
10. asparagine synthetase type II [Phaseolus vulgaris]
11. asparagine synthetase type II [Phaseolus vulgaris]
12. Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays]
13. asparagine synthetase type II [Phaseolus vulgaris]
14. Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays]
15. asparagine synthetase type II [Phaseolus vulgaris]
16. asparagine synthetase type II [Phaseolus vulgaris]
17. asparagine synthetase type II [Phaseolus vulgaris]
18. asparagine synthetase type II [Phaseolus vulgaris]
19. asparagine synthetase type II [Phaseolus vulgaris]
20. asparagine synthetase type II [Phaseolus vulgaris]
21. asparagine synthetase type II [Phaseolus vulgaris]
22. asparagine synthetase type II [Phaseolus vulgaris]
23. asparagine synthetase type II [Phaseolus vulgaris]
24. asparagine synthetase type II [Phaseolus vulgaris]
25. Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays]
26. Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays]
27. Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays]
28. Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays]
29. Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays]
30. Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays]
31. Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays]
32. Asparagine synthetase [glutamine-hydrolyzing] (Glutamine-dependent asparagine synthetase) gi|7438077|pir||T02978

| | FunCat Hit_Desc |
|---|---|
| | asparagine synthase (glutamine-hydrolysing) (EC 6.3.5.4) - maize gi|984262|emb|CAA58058.1| asparragine synthetase [Zea mays] |
| 33. | Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] |
| 34. | Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] |
| 35. | Asparagine synthase [glutamine-hydrolyzing] (AS) gi|100980|pir||S25165 asparagine synthase (glutamine-hydrolysing) (EC 6.3.5.4) - garden asparagus gi|16076|emb|CAA48141.1|asparagine synthase (glutamine-hydrolysing) [Asparagus officinalis] |
| 36. | Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] |
| 37. | asparagine synthetase type II [Phaseolus vulgaris] |
| 38. | Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] |
| 39. | Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] |
| 40. | Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] |
| 41. | Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] |
| 42. | Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] |
| 43. | Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] |
| 44. | Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] |
| 45. | Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] |
| 46. | Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] |
| 47. | Asparagine synthetase [glutamine-hydrolyzing] (Glutamine-dependent asparagine synthetase) gi|7438077|pir||T02978 asparagine synthase (glutamine-hydrolysing) (EC 6.3.5.4) - maize gi|984262|emb|CAA58052.1| asparragine synthetase [Zea mays] |
| 48. | asparagine synthetase type II [Phaseolus vulgaris] |
| 49. | Asn1p and Asn2p are isozymes; Asn1p [Saccharomyces cerevisiae] gi|1351984|sp|P49089|ASN1_YEAST Asparagine synthetase [glutamine-hydrolyzing] 1 (Glutamine-dependent asparagine synthetase 1) gi|1077018|pir||S52694 asparagine synthase (glutamine-hydrolysing) (EC 6.3.5.4) - yeast (Saccharomyces cerevisiae) gi|747902|emb|CAA88594.1| asparagine synthetase [Saccharomyces cerevisiae] gi|1066479|gb|AAB68284.1| Asn1p: Asparagine synthetase [Saccharomyces cerevisiae] |
| 50. | Required for invasion and pseudohyphae formation in response to nitrogen starvation; Muc1p [Saccharomyces cerevisiae] gi|728850|sp|P08640|AMYH_YEAST Glucoamylase S1/S2 precursor (Glucan 1,4-alpha-glucosidase) (1,4-alpha-D-glucan glucohydrolase) gi|626156|pir||S48478 glucan 1,4-alpha-glucosidase (EC 3.2.1.3) - yeast (Saccharomyces cerevisiae) gi|557822|emb|CAA86176.1| mal5, sta1, len: 1367, CAI: 0.3, AMYH_YEAST P08640 GLUCOAMYLASE S1 (EC 3.2.1.3) [Saccharomyces cerevisiae] gi|1304387|gb|AAC49609.1| glucoamylase [Saccharomyces cerevisiae var. diastaticus] |
| 51. | Required for invasion and pseudohyphae formation in response to nitrogen starvation; Muc1p [Saccharomyces cerevisiae] gi|728850|sp|P08640|AMYH_YEAST Glucoamylase S1/S2 precursor (Glucan 1,4-alpha-glucosidase) (1,4-alpha-D-glucan glucohydrolase) gi|626156|pir||S48478 glucan 1,4-alpha-glucosidase (EC 3.2.1.3) - yeast (Saccharomyces cerevisiae) gi|557822|emb|CAA86176.1| mal5, sta1, len: 1367, CAI: 0.3, AMYH_YEAST P08640 GLUCOAMYLASE S1 (EC 3.2.1.3) [Saccharomyces cerevisiae] gi|1304387|gb|AAC49609.1| glucoamylase [Saccharomyces cerevisiae var. diastaticus] |
| 52. | Asn1p and Asn2p are isozymes; Asn1p [Saccharomyces cerevisiae] gi|1351984|sp|P49089|ASN1_YEAST Asparagine synthetase [glutamine-hydrolyzing] 1 (Glutamine-dependent asparagine synthetase 1) gi|1077018|pir||S52694 asparagine synthase (glutamine-hydrolysing) (EC 6.3.5.4) - yeast (Saccharomyces cerevisiae) gi|747902|emb|CAA88594.1| asparagine synthetase [Saccharomyces cerevisiae] gi|1066479|gb|AAB68284.1| Asn1p: Asparagine synthetase [Saccharomyces cerevisiae] |
| 53. | Asn1p and Asn2p are isozymes; Asn1p [Saccharomyces cerevisiae] gi|1351984|sp|P49089|ASN1_YEAST Asparagine synthetase [glutamine-hydrolyzing] 1 (Glutamine-dependent asparagine synthetase 1) gi|1077018|pir||S52694 asparagine synthase (glutamine-hydrolysing) (EC 6.3.5.4) - yeast (Saccharomyces cerevisiae) gi|747902|emb|CAA88594.1| asparagine synthetase [Saccharomyces cerevisiae] gi|1066479|gb|AAB68284.1| Asn1p: Asparagine synthetase [Saccharomyces cerevisiae] |
| 54. | Required for invasion and pseudohyphae formation in response to nitrogen starvation; Muc1p [Saccharomyces cerevisiae] gi|728850|sp|P08640|AMYH_YEAST Glucoamylase S1/S2 precursor (Glucan 1,4-alpha-glucosidase) (1,4-alpha-D-glucan glucohydrolase) gi|626156|pir||S48478 glucan 1,4-alpha-glucosidase (EC 3.2.1.3) - yeast (Saccharomyces cerevisiae) gi|557822|emb|CAA86176.1| mal5, sta1, len: 1367, CAI: 0.3, AMYH_YEAST P08640 GLUCOAMYLASE S1 (EC 3.2.1.3) [Saccharomyces cerevisiae] gi|1304387|gb|AAC49609.1| glucoamylase [Saccharomyces cerevisiae var. diastaticus] |

| | FunCat_Evalue | FunCat_Hit_No | FunCat_Pct_Iden | FunCat_Q_range | FunCat_Q_Coverage | FunCat_Hit_Coverage |
|---|---|---|---|---|---|---|
| 1. | 0.00 | 1.00 | 78.00 | 6.00 | 85.00 | 100.00 |
| 2. | 0.00 | 6.00 | 75.00 | 6.00 | 79.00 | 93.00 |
| 3. | 0.00 | 6.00 | 75.00 | 6.00 | 79.00 | 93.00 |
| 4. | 0.00 | 6.00 | 75.00 | 6.00 | 79.00 | 93.00 |
| 5. | 0.00 | 6.00 | 75.00 | 6.00 | 79.00 | 93.00 |
| 6. | 0.00 | 6.00 | 75.00 | 6.00 | 79.00 | 93.00 |
| 7. | 0.00 | 6.00 | 75.00 | 6.00 | 79.00 | 93.00 |
| 8. | 0.00 | 6.00 | 75.00 | 6.00 | 79.00 | 93.00 |
| 9. | 0.00 | 6.00 | 75.00 | 6.00 | 79.00 | 93.00 |
| 10. | 0.00 | 6.00 | 75.00 | 6.00 | 79.00 | 93.00 |
| 11. | 0.00 | 6.00 | 75.00 | 6.00 | 79.00 | 93.00 |
| 12. | 0.00 | 1.00 | 78.00 | 6.00 | 85.00 | 100.00 |
| 13. | 0.00 | 6.00 | 75.00 | 6.00 | 79.00 | 93.00 |
| 14. | 0.00 | 1.00 | 78.00 | 6.00 | 85.00 | 100.00 |
| 15. | 0.00 | 6.00 | 75.00 | 6.00 | 79.00 | 93.00 |

-continued

| | FunCat_Evalue | FunCat_Hit_No | FunCat_Pet_Iden | FunCat_Q_range | FunCat_Q_Coverage | FunCat_Hit_Coverage |
|---|---|---|---|---|---|---|
| 16. | 0.00 | 6.00 | 75.00 | 6.00 | 79.00 | 93.00 |
| 17. | 0.00 | 6.00 | 75.00 | 6.00 | 79.00 | 93.00 |
| 18. | 0.00 | 6.00 | 75.00 | 6.00 | 79.00 | 93.00 |
| 19. | 0.00 | 6.00 | 75.00 | 6.00 | 79.00 | 93.00 |
| 20. | 0.00 | 6.00 | 75.00 | 6.00 | 79.00 | 93.00 |
| 21. | 0.00 | 6.00 | 75.00 | 6.00 | 79.00 | 93.00 |
| 22. | 0.00 | 6.00 | 75.00 | 6.00 | 79.00 | 93.00 |
| 23. | 0.00 | 6.00 | 75.00 | 6.00 | 79.00 | 93.00 |
| 24. | 0.00 | 6.00 | 75.00 | 6.00 | 79.00 | 93.00 |
| 25. | 0.00 | 1.00 | 78.00 | 6.00 | 85.00 | 100.00 |
| 26. | 0.00 | 1.00 | 78.00 | 6.00 | 85.00 | 100.00 |
| 27. | 0.00 | 1.00 | 78.00 | 6.00 | 85.00 | 100.00 |
| 28. | 0.00 | 1.00 | 78.00 | 6.00 | 85.00 | 100.00 |
| 29. | 0.00 | 1.00 | 78.00 | 6.00 | 85.00 | 100.00 |
| 30. | 0.00 | 1.00 | 78.00 | 6.00 | 85.00 | 100.00 |
| 31. | 0.00 | 1.00 | 78.00 | 6.00 | 85.00 | 100.00 |
| 32. | 0.00 | 1.00 | 78.00 | 6.00 | 85.00 | 100.00 |
| 33. | 0.00 | 1.00 | 78.00 | 6.00 | 85.00 | 100.00 |
| 34. | 0.00 | 1.00 | 78.00 | 6.00 | 85.00 | 100.00 |
| 35. | 0.00 | 3.00 | 74.00 | 6.00 | 80.00 | 94.00 |
| 36. | 0.00 | 1.00 | 78.00 | 6.00 | 85.00 | 100.00 |
| 37. | 0.00 | 6.00 | 75.00 | 6.00 | 79.00 | 93.00 |
| 38. | 0.00 | 1.00 | 78.00 | 6.00 | 85.00 | 100.00 |
| 39. | 0.00 | 1.00 | 78.00 | 6.00 | 85.00 | 100.00 |
| 40. | 0.00 | 1.00 | 78.00 | 6.00 | 85.00 | 100.00 |
| 41. | 0.00 | 1.00 | 78.00 | 6.00 | 85.00 | 100.00 |
| 42. | 0.00 | 1.00 | 78.00 | 6.00 | 85.00 | 100.00 |
| 43. | 0.00 | 1.00 | 78.00 | 6.00 | 85.00 | 100.00 |
| 44. | 0.00 | 1.00 | 78.00 | 6.00 | 85.00 | 100.00 |
| 45. | 0.00 | 1.00 | 78.00 | 6.00 | 85.00 | 100.00 |
| 46. | 0.00 | 1.00 | 78.00 | 6.00 | 85.00 | 100.00 |
| 47. | 0.00 | 1.00 | 78.00 | 6.00 | 85.00 | 100.00 |
| 48. | 0.00 | 6.00 | 75.00 | 6.00 | 79.00 | 93.00 |
| 49. | 1.0e−149 | 64.00 | 48.00 | 6.00 | 79.00 | 99.00 |
| 50. | 3.0e−28 | 148.00 | 25.00 | 6.00 | 91.00 | 75.00 |
| 51. | 3.0e−28 | 148.00 | 25.00 | 6.00 | 91.00 | 75.00 |
| 52. | 1.0e−149 | 64.00 | 48.00 | 6.00 | 79.00 | 99.00 |
| 53. | 1.0e−149 | 64.00 | 48.00 | 6.00 | 79.00 | 99.00 |
| 54. | 3.0e−28 | 148.00 | 25.00 | 6.00 | 91.00 | 75.00 |

REFERENCES

The following references, to the extent that they provide exemplary procedural or other details supplementary to those set forth herein, are specifically incorporated herein by reference:

U.S. Pat. No. 4,761,373
U.S. Pat. No. 4,957,748
U.S. Pat. No. 5,100,679
U.S. Pat. No. 5,219,596
U.S. Pat. No. 5,322,783
U.S. Pat. No. 5,322,938
U.S. Pat. No. 5,538,880
U.S. Pat. No. 5,550,318
U.S. Pat. No. 5,563,055
U.S. Pat. No. 5,610,042
U.S. Pat. No. 5,633,435
U.S. Pat. No. 5,936,069
U.S. Pat. No. 6,005,076
U.S. Pat. No. 6,146,669
U.S. Pat. No. 6,156,227
U.S. Pat. No. 6,194,636
U.S. Pat. No. 6,232,526
U.S. Patent Application Publication 20040216189A1
U.S. Patent Application Publication 20050048624A1
Alba, *Plant J.*, 39(5): 681-808, 2004.
Allard, In: *Principles of Plant Breeding*, $2^{nd}$ Ed., John Wiley & Sons, ISBN: 0471023094, 1999.
Altschul et al., *Nucleic Acids Res.*, 25:3389-3402, 1997,
Aslanidis and de Jong, *Nucleic Acids Res.*, 18(20):6069-6074, 1990.
Ausubel et al., eds. *Current Protocols in Molecular Biology*, John Wiley & Sons, New York, 1989.
Bevan, *Nucleic Acids Res.*, 12:8711-8721, 1984.
Chu et al., *Scientia Sinica*, 18:659, 1975.
Dellaporta et al., *Plant Molecular Biology Reporter*, 1:19-21, 1983.
D'Halluin et al., *Bio/Technology*, 10:309-314, 1992.
Fraley et al., *Proc. Natl. Acad. Sci. USA*, 80:4803-4807, 1983.
Haymes et al., *Nucleic Acid Hybridization, A Practical Approach*, IRL Press, Washington, D.C., 1985.
Hayward, In: *Plant Breeding: Principles and Prospects*, Vol. 1, Chapman & Hall, ISBN: 0412433907, 1993.
Henikoff and Henikoff, *Proc. Natl. Acad. Sci. USA*, 89:10915-10919, 1992.
Herrera-Estrella et al., *Nature*, 303:209, 1983.
Hinchee et al., *Bio/Technology*, 6:915-922, 1988
Jones and Shenk, *Cell*, 13:181-188, 1978.
Jones et al., *Mol. Gen. Genet.*, 210(1):1-4, 1987.
Klee et al., *Bio-Technology*, 3(7):637-642, 1985.
Lewin, In: *Genes V*, Oxford University Press, NY, 1994.
Matsuoka et al., *Proc. Natl. Acad. Sci. USA*, 90:9586-9590, 1993.
Murashige and Skoog, *Physiol. Plant*, 15:473-497, 1962.
Murray and Williams, In: *Chemical Principles of Near-Infrared Technology*, Near-Infrared Technology in the Agricultural and Food Industries, Williams and K. Norris (Eds.,), 1987.
PCT Appln. WO 95/06128
Reynaerts et al., In: *Selectable and Screenable Markers*, Gelvin and Schilperoort (Eds.), Plant Molecular Biology Manual, Kluwer, Dordrecht, 1988.
Richards, In: *Plant Breeding Systems*, Stanley Thornes Pub Ltd; $2^{nd}$ Ed., ISBN: 0412574500, 1997.
Rieger et al., *Glossary of Genetics: Classical and Molecular*, 5th edition, Springer-Verlag: New York, 1991.
Sambrook et al., *Molecular Cloning, A Laboratory Manual*, 2nd Ed., Cold Spring Harbor Press, Cold Spring Harbor, N.Y., 2001
Stalker et al., *J. Biol. Chem.*, 263:6310-6314, 1988.
Thillet et al., *J. Biol. Chem.*, 263:12500-12508, 1988.

What is claimed is:

1. A transgenic corn seed comprising in its genome a heterologous DNA construct comprising a promoter operably linked to a polynucleotide, the polynucleotide comprising:
    (a) a nucleic acid sequence comprising the sequence of SEQ ID NO:5;
    (b) a nucleic acid sequence encoding the polypeptide of SEQ ID NO:6; or
    (c) a nucleic acid sequence with at least 95% sequence identity to SEQ ID NO:5 that encodes an asparagine synthetase.

2. The transgenic corn seed of claim 1, wherein said polynucleotide encodes SEQ ID NO:6.

3. The transgenic corn seed of claim 1, wherein said polynucleotide comprises the nucleic acid sequence of SEQ ID NO:5.

4. The transgenic corn seed of claim 1, wherein said promoter is a rice actin 1 promoter.

5. A transgenic corn plant comprising in its genome a heterologous DNA construct comprising a promoter operably linked to a polynucleotide, the polynucleotide comprising:
    (a) a nucleic acid sequence comprising the sequence of SEQ ID NO:5;
    (b) a nucleic acid sequence encoding the polypeptide of SEQ ID NO:6; or
    (c) a nucleic acid sequence with at least 95% sequence identity to SEQ ID NO:5 that encodes an asparagine synthetase.

6. The transgenic corn plant of claim 5, wherein said polynucleotide encodes SEQ ID NO:6.

7. The transgenic corn plant of claim 5, wherein said polynucleotide comprises the sequence of SEQ ID NO:5.

8. The transgenic corn plant of claim 5, wherein said promoter is a rice actin 1 promoter.

* * * * *